US010632181B2

(12) United States Patent
Um et al.

(10) Patent No.: US 10,632,181 B2
(45) Date of Patent: Apr. 28, 2020

(54) COMPOSITION, CONTAINING RGD MOTIF-CONTAINING PEPTIDE OR FRAGMENT THEREOF, FOR TREATING BURNS AND GLAUCOMA, ALLEVIATING SKIN WRINKLES, AND PROMOTING HAIR GROWTH

(71) Applicant: HUONS CO., LTD., Gyeonggi-do (KR)

(72) Inventors: Key-An Um, Gyeonggi-do (KR); Yeong-Mok Kim, Seoul (KR); Jong Hwan Lim, Gyeonggi-do (KR)

(73) Assignee: HUONS CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/574,442

(22) Filed: Sep. 18, 2019

(65) Prior Publication Data

US 2020/0000891 A1    Jan. 2, 2020

Related U.S. Application Data

(62) Division of application No. 15/540,896, filed as application No. PCT/KR2015/014580 on Dec. 31, 2015, now Pat. No. 10,463,720.

(30) Foreign Application Priority Data

Dec. 31, 2014   (KR) .................. 10-2014-0195008

(51) Int. Cl.
| | |
|---|---|
| *A61K 38/48* | (2006.01) |
| *A61K 38/17* | (2006.01) |
| *A61K 38/16* | (2006.01) |
| *A61P 27/06* | (2006.01) |
| *A61P 17/14* | (2006.01) |
| *A61P 17/02* | (2006.01) |
| *A61K 8/66* | (2006.01) |
| *A61Q 7/00* | (2006.01) |
| *A61Q 19/00* | (2006.01) |
| *A61Q 19/08* | (2006.01) |

(52) U.S. Cl.
CPC ............ *A61K 38/4886* (2013.01); *A61K 8/66* (2013.01); *A61K 38/16* (2013.01); *A61K 38/17* (2013.01); *A61P 17/02* (2018.01); *A61P 17/14* (2018.01); *A61P 27/06* (2018.01); *A61Q 7/00* (2013.01); *A61Q 19/00* (2013.01); *A61Q 19/08* (2013.01); *C12Y 304/24* (2013.01); *A61K 2800/74* (2013.01)

(58) Field of Classification Search
None
See application file for complete search history.

(56) References Cited

U.S. PATENT DOCUMENTS

| | | |
|---|---|---|
| 9,101,581 B2 | 8/2015 | Kim et al. |
| 2007/0065415 A1 | 3/2007 | Kleinsek et al. |
| 2007/0167369 A1 | 7/2007 | Nam et al. |
| 2008/0188413 A1 | 8/2008 | Chuang et al. |
| 2009/0220463 A1 | 9/2009 | Kim et al. |
| 2010/0297100 A1 | 11/2010 | Jang et al. |
| 2011/0014307 A1 | 1/2011 | Ota et al. |
| 2011/0152192 A1 | 6/2011 | Chuang et al. |
| 2014/0105868 A1 | 4/2014 | Kim et al. |

FOREIGN PATENT DOCUMENTS

| | | |
|---|---|---|
| JP | 10-017488 A | 1/1998 |
| JP | 3579063 B2 | 10/2004 |
| KR | 10-2010-0075471 | 7/2010 |
| KR | 10-2011-0073569 | 6/2011 |
| KR | 10-2012-0130752 A | 3/2012 |
| WO | WO-2007/083949 A1 | 7/2007 |
| WO | WO-2009/123211 A1 | 10/2009 |
| WO | WO-2013/137606 A1 | 9/2013 |

OTHER PUBLICATIONS

Lowe, Brit. J. Ophthal. (1965) 49 p. 460-465.*
Genbank; AAH 14566.1, (ADAM Metallopeptidase Domain 15, Sep. 11, 2007.
Mas-Moruno, Carlos et al, "Cilengitide: the first anti-angiogenic small molecule drug candidate. Design, synthesis and clinical evalulation." Anti-Canc. Agents Med. Chem. (2010) 10(10) p. 753-768.
ISR dated Apr. 19, 2016 in PCT/KR2015/014580, published as WO 2016/108669.
White, Judith M.; "adams: modulators of cell-cell and cell-matrix interaction"; Current Opinion in Cell Biology, 2003, 15, pp. 598-606.
Blobel, Carl P., et al.; "Proteolytic Processing of a Protein Involved in Sperm-Egg Fusion Correlates with Acquisition of Fertilization Competence", The Journal of Cell Biology, vol. 111, Jul. 1990, pp. 69-78.
Aitken, John.; "A Family of Fusion Proteins", Nature, Mar. 19, 1992, 356, 6366, proquest Central Korea, p. 196.
Blobel, Carl P., et al.; "A Potential Fusion Peptide and an Integrin Ligand Domain in a Protein Active in Sperm-Egg Fusion", Nature; Mar. 19, 1992; 356, 6366; proquest Central Korea, p. 248.
Office Action (Final) from corresponding U.S. Appl. No. 15/540,896, dated Nov. 30, 2018.
Office Action (Non-final) from corresponding U.S. Appl. No. 15/540,896, dated Jul. 16, 2018.

(Continued)

*Primary Examiner* — Fred H Reynolds
(74) *Attorney, Agent, or Firm* — Harness, Dickey & Pierce, P.L.C.

(57) ABSTRACT

The present invention relates to an RGD motif-containing peptide or a fragment thereof, which is used to effectively treat burns and glaucoma, obtain an excellent effect of alleviating skin wrinkles, and is effective in the promotion of hair restoration and hair growth as well as the prevention of hair loss. Therefore, the motif-containing peptide or the fragment thereof can be utilized for a cosmetic composition and a pharmaceutical composition.

7 Claims, 37 Drawing Sheets

Specification includes a Sequence Listing.

(56) References Cited

OTHER PUBLICATIONS

"The revolution in anti-wrinkle ingredients of the cosmetic polypeptide- cyclic pentapeptide for cosmetics", Bai Rujiang, China Cosmetics, No. 9, pp. 65-69, Dec. 31, 2012.
"Novel function of human ADAM15 disintegrin-like domain and its derivatives in platelet aggregation", Ok-Hee Jeon et al, Thrombosis Research (2007) 119, pp. 609-619, Dec. 31, 2007.

* cited by examiner

COMPOSITION, CONTAINING RGD MOTIF-CONTAINING PEPTIDE OR FRAGMENT THEREOF, FOR TREATING BURNS AND GLAUCOMA, ALLEVIATING SKIN WRINKLES, AND PROMOTING HAIR GROWTH

CROSS-REFERENCE TO RELATED APPLICATIONS

This application is a divisional application of U.S. application Ser. No. 15/540,896, filed on 29 Jun. 2017, which is a national phase application of PCT Application No. PCT/KR2015/014580, filed on Dec. 31, 2015, which claims the benefit and priority to Korean Patent Application No. 10-2014-0195008, filed on Dec. 31, 2014. The entire disclosures of the applications identified in this paragraph are incorporated herein by references.

FIELD

The present disclosure relates to a peptide or its fragment having skin wrinkle reduction, burn and glaucoma treatment, and hair growth promotion effects, and a pharmaceutical composition and a cosmetic composition comprising the same.

BACKGROUND

A disintegrin and metalloproteinase (hereinafter referred to as "ADAM") is a disintegrin and metalloproteinase domain-containing multifunctional protein, and is known for having both adhesive and proteolytic properties in cell-cell and cell-matrix interactions. ADAM15 is a unique protein having an Arg-Gly-Asp (RGD) motif in its disintegrin-like domain. ADAM15 is expressed in smooth muscle cells, mesangial cells and endothelial cells. ADAM family involves in various biological processes such as fertilization, muscle development, nerve growth, and cytokine secretion (Blobel C P, et al.; Nature 1992. 356: 248-252.; Aitken, J. Nature 1992; 356: 196-197; Blobel C P, et al. J. Cell Biol. 1990; 111: 69-78.; White J M. Curr. Opin. Cell. Biol. 2003; 15: 598-606). It is known that the disintegrin-like domain known as EGF (Epidermal growth factor)-like domain of ADAM15, especially, specifically binds integrin beta chain (integrin beta 3) and binds Src family protein tyrosine kinase, and functions in the signal transmission and adhesion between cells. ADAM 15 protein is known for being associated with inflammatory diseases such as rheumatism and various diseases including breast cancer and prostate cancer, and further study is needed.

On the other hand, human skin is composed of the epidermis including the stratum corneum and dermis, and the connective tissue, and the stratum corneum is composed of layers of dead cells formed through a differentiation process of keratinocytes, basal cells in the epidermis, and plays a role in protecting the human body from the influence of outdoor environment. Furthermore, the dermis layer that is located in the skin is composed of fibrous proteins, collagen and elastin, and provides elasticity to the skin and serves to stay the skin tight, and the dermis layer has blood vessels and nerves and also contain mast cells that involve in allergic reactions, and natural moisturizing factors such as Na-PCA or hyaluronic acid.

The cause of skin wrinkle generation is largely classified into two: one is "intrinsic aging" comprising age-related changes in function of cells, namely, the unit that makes up the skin, and the other is "extrinsic aging" or aging related to outdoor environment, i.e., ultraviolet (UV) rays, air pollution, and stress. Photoaging, the prolonged exposure to UV, is the greatest cause of skin aging, and causes acute and chronic skin wound including skin cancer and wrinkle. This is classified into three: UVA (320-400 nm), UVB (290-320 nm) and UVC (200-290 nm), according to the wavelength ranges in solar light, and UVC is almost completely absorbed by the ozone layer, whereas UVA and UVB reach the Earth's surface and act as a fatal factor causing skin damage. It is known that UVB having shorter wavelengths, but higher intensity, than UVA penetrates the epidermis that rests on the dermis and damages keratinocytes and collagen fibers, consequently causing wrinkle generation, skin discoloration or skin cancer. Furthermore, recently it was discovered that interactions between cellular and extracellular matrix proteins (collagen, fibrillin, fibronectin) play an important role in the survival and growth of skin cell and reconstruction of tissue.

Burns are primarily caused by accidents, and can be classified into heat burns, electrical burns, chemical burns, radiation burns according to the cause. The severity of a burn is divided into first-, second-, third- and fourth-degree burns according to the burned width and depth, the contact time with the temperature of objects causing burns, and skin conditions. In second or higher degree burns, scar may be left behind and treatment in hospital is required.

First-degree burns cause skin redness and itching pain. They cause damage to the epidermis, the outermost layer of the skin layer, and swelling accompanied by pain and redness. The symptoms disappear in a few days, but superficial exfoliation and pigmentation may be left behind. After recovery, cicatrix (scar) does not remain. Sunburn is the most common example of first-degree burn.

Second-degree burns affect the epidermis and dermis, and cause redness, pain, swelling, and blisters in 24 hours after accidents. Second-degree burns may affect the sweat glands or pores. Severe burning sensation and pain occurs. Rupture of blisters leaves eroded areas and releases the secretion in large amounts. When the burned area is about 15% or more of the body surface area, special attention should be given. Second-degree burns are cured in a few weeks, but in many cases, pigmentation or depigmentation is left behind. When secondary infections occur, partial symptoms become severer and it takes longer to heal.

Third-degree burns affect the epidermis, dermis, and even subcutaneous fat, and the skin becomes darker or lighter in color, and blood vessels immediately beneath the skin surface are coagulated. Burned regions may be benumbed, but patients feel extremely severe pain and there is the death of skin tissue and structure, requiring a lot of time to treat, with scars left behind. In 2 weeks after accidents, scabs peel away and reveal ulcerated surface. Large quantities of fluids are secreted and bleeding is likely to occur, but third-degree burns are healed when new tissues gradually form, leading to regeneration of epidermis, with cicatrix left behind. When deep skin necrosis develops, or when secondary infections occur, healing is delayed and uneven cicatrix surface is created, resulting in keloid formation or deformation or movement disorders. When the burned area is 10% or more of the body surface area, special attention is required.

Fourth-degree burns involve carbonized and darkened tissues of burned regions, and extend through the skin layer to injure fatty layer, ligaments, fasciae, muscles, and even bone tissues. Fourth-degree burns primarily include high voltage electrical burns, and in some cases, deep dermal 2-3 degree burns may develop to fourth-degree burns when viral infection occurs. When the burned area ranges 20% or more, responses may occur all over the body; hypotension, shock, acute kidney dysfunction may occur due to excessive loss of body fluids, and wound infection or pneumonia, sepsis, and multiple organ dysfunction syndrome may occur later.

Burns treatment focus on the regeneration of skin and skin appendages, but currently developed technology does not provide a perfect treatment.

Glaucoma collectively means diseases that is caused in optic nerve including retinal plexus cells and have a form of optic nerve atrophy. Untreated glaucoma may eternally affect vision. In the past, glaucoma was defined as a disease that causes optic nerve damage and consequential visual impairment due to higher intraocular pressure than normal, but recently, it is reported that optic nerve damage of glaucoma is caused by many factors other than high intraocular pressure, and thus, glaucoma is defined as a progressive optic nerve syndrome causing characteristic changes of optic nerve and consequential visual impairment.

Glaucoma may be classified into open angle glaucoma, closed angle glaucoma, congenital glaucoma, secondary glaucoma, phacolytic glaucoma, pseudoexfoliation glaucoma, phacomorphic glaucoma, neovascular glaucoma, and steroid glaucoma, according to causes or syndromes.

In glaucoma patients, in the event that the intraocular pressure is not adjusted by drug treatment and laser treatment, or despite adequate drug treatment, visual impairment is found in vision examination and worsening sign of optic nerve changes of glaucoma is found in funduscopic examination, or when the use of drugs is disallowed due to adverse effects, surgical treatment is considered. Trabeculectomy is one of commonly used surgery methods. Trabeculectomy allows artificial drainage of aqueous humor through filtering blebs to reduce the intraocular pressure. The wound healing process and scar formation in the filtering blebs formed by surgery causes blockage of aqueous humor drainage pathway and gradually degrades the function of filtering blebs, resulting in surgery failure. Currently, to increase the long-term surgery success rate of trabeculectomy, antimetabolite, 5-fluorouracil (5-FU) or mitomycin C (MMC), is used as adjuvant treatment, and it resulted in a higher success rate of trabeculectomy but increased late complications, for example, low intraocular pressure, filtering bleb leaks, and filtering bleb-related infection. More recently, there is a report that OculusGen™ (OculusGen Biomedical Inc., Taipei, Taiwan) is used to provide a scaffold for growth of fibroblast in ' discretionally organized' way, and allow 'discretionally arranged fibroblasts' to produce and arrange collagen in many directions around cells so that structure similar to the collagen structure found in normal tissue is formed, not collagen structure found in scar tissue, for use in trabeculectomy. However, there is a need for alternative solutions to treat glaucoma other than trabeculectomy.

Generally, the hair growth cycle has three stages: anagen, catagen, and telogen. Anagen is the active growth phase of hair and occupies the most of the hair growth life cycle. Catagen is characterized by apoptosis, and in this phase, hair is ready to fall off, and telogen is the resting or quiescent phase of hair follicles during which hair begins to fall, causing a noticeable loss of hair.

Alopecia or hair loss occurs when hair roots become weak and hair is thinned in repetitions of anagen-catagen-telogen, and eventually, hair becomes soft, fine and short. It is known that the cause of hair loss includes inherited factors, over-secretion of sexual hormone testosterone, reduced blood flow to follicles, over-secretion of sebum, stress, irregular food timings, air pollution, and excessive exposure to UV, and in most cases, many causes act in combination.

Alopecia is greatly classified into androgenetic alopecia, female pattern hair loss, alopecia areata, and hair loss caused by other causes. Androgenetic alopecia is a phenomenon appearing due to a male hormone, called testosterone, playing a role in promoting male sexual characteristics and causing muscles to grow and male organs to mature during adolescence, and when testosterone is converted to a more potent hormone dihydrotestosterone (DHT) by 5 α-reductase enzyme, the hormone acts on follicle dermal papilla cells to induce anagen-to-catagen transition in follicles, resulting in hair loss. Female pattern hair loss is usually due to low estosterone levels after menopause. Female pattern hair loss does not emerge on the frontal scalp and mainly proceeds over the mid scalp, dissimilar to androgenetic alopecia. Hair loss in women is less associated with 5 α-reductase than men. Thus, drugs which inhibit 5 α-reductase do not work for women experiencing hair loss after menopause. Alopecia areata is caused by autoimmune diseases, mental stress, or inherited factors. Alopecia areata represents round or oval patches of hair loss, and is characterized by tinea capitis or trichotillomania. The cause of alopecia areata is fundamentally different from androgenetic alopecia, and different treatment methods are used, for example, drugs to control adrenal cortex hormones are used, or minoxidil is applied to affected parts.

To solve the hair loss problem, various active ingredients having hair loss prevention and treatment effects and compositions including the same have been studied. The main or intended effect of this study includes an effect in maintaining hair thickness or thickening hair, an effect for induced early onset or prolonged anagen, an effect for delayed or shortened telogen release, an inhibitory effect of 5α-reductase activity, an effect on the promotion of blood circulation to hair follicles, a moisturizing effect, an anti-oxidation effect, a dandruff prevention effect, a sterilization effect, and an Extra-Cellular matrix (ECM) expression promotion effect.

The approved medication being used now is Minoxidil. Minoxidil was originally produced as an antihypertensive drug that helps the widening of smooth muscle blood vessels, but was developed as a drug to promote hair growth after discovery of its adverse effects, hair growth everywhere on the body (U.S. Pat. Nos. 4,596,812 and 4,139,619). Although its detailed scientific mechanism of action is not known, it is regarded that Minoxidil promotes hair growth through combination action of providing more blood flow to follicles. Based on this effect, Minoxidil was approved as over-the-counter medication by FDA, but adverse effects such as skin irritation, itching, redness, hair growth in unwanted part, and worsening of hair loss were reported, and also it should be continuously administered to maintain efficacy.

DISCLOSURE

Technical Problem

To solve the aforementioned problems, the present disclosure is directed to providing a peptide having a particular sequence and structure, and a pharmaceutical composition and a cosmetic composition having excellent effect on the improvement or treatment in skin wrinkle, burn, glaucoma and hair loss.

Technical Solution

To achieve the object, the present disclosure provides a composition comprising a peptide consisting of an amino acid sequence of SEQ ID NO: 1 comprising an RGD motif (Arg-Gly-Asp motif) or its fragment as an active ingredient, and having at least one of the following effects:
  burn treatment;
  glaucoma treatment;
  skin wrinkle reduction; or
  hair loss prevention, scalp health improvement, or hair growth and hair restoration promotion.

Preferably, the peptide fragment may be at least one selected from the followings:

1) a fragment consisting of 5-45 amino acids comprising the RGD motif of SEQ ID NO: 1, optionally with no disulfide bond or 3 or less disulfide bonds between cysteines in the fragment;

2) a fragment comprising 30th-38th amino acids in the amino acid sequence of SEQ ID NO: 1, optionally with no disulfide bond or 1 or more disulfide bonds between cysteines in the fragment;

3) a fragment comprising 32nd-43rd amino acids in the amino acid sequence of SEQ ID NO: 1, optionally with no disulfide bond or 1 or more disulfide bonds between cysteines in the fragment;

4) a fragment comprising 30th-44th amino acids in the amino acid sequence of SEQ ID NO: 1, optionally with no disulfide bond or 1 or more disulfide bonds between cysteines in the fragment;

5) a fragment comprising 18th-54th amino acids in the amino acid sequence of SEQ ID NO: 1, optionally with no disulfide bond or 1 or more disulfide bonds between cysteines in the fragment; and 6) a fragment comprising 10th-54th amino acids in the amino acid sequence of SEQ ID NO: 1, optionally with no disulfide bond or 1 or more disulfide bonds between cysteines in the fragment.

More preferably, the peptide fragment may be at least one selected from the followings:

1) a fragment consisting of 9, 12 or 15 amino acids comprising the RGD motif of SEQ ID NO: 1, optionally with no disulfide bond or 3 or less disulfide bonds between cysteines in the fragment;

2) a fragment consisting of 30th-38th amino acids in the amino acid sequence of SEQ ID NO: 1;

3) a fragment consisting of 32nd-43rd amino acids in the amino acid sequence of SEQ ID NO: 1, with a disulfide bond between 36th cysteine and 42nd cysteine;

4) a fragment consisting of 30th-44th amino acids in the amino acid sequence of SEQ ID NO: 1, with no disulfide bond between cysteines in the fragment; or 5) a fragment consisting of 30th-44th amino acids in the amino acid sequence of SEQ ID NO: 1, with a disulfide bond between cysteines in the fragment.

The composition according to the present disclosure may be used for a pharmaceutical composition, a cosmetic composition, a health functional food composition, and a quasi-drug composition.

Furthermore, the present disclosure provides a method for administering a peptide consisting of an amino acid sequence of SEQ ID NO: 1 comprising an RGD motif (Arg-Gly-Asp motif) or its fragment to provide at least one of the following effects (hereinafter referred to as 'method'):
  burn treatment;
  glaucoma treatment;
  skin wrinkle reduction; or
  hair loss prevention, scalp health improvement, or hair growth and hair restoration promotion.

Furthermore, the present disclosure provides use of a peptide consisting of an amino acid sequence of SEQ ID NO: 1 comprising an RGD motif (Arg-Gly-Asp motif) or its fragment to provide at least one of the following effects (hereinafter referred to as 'use'):
  burn treatment;
  glaucoma treatment;
  skin wrinkle reduction; or
  hair loss prevention, scalp health improvement, or hair growth and hair restoration promotion.

The 'composition', 'method' and 'use' stated herein is based on the effects of a peptide consisting of an amino acid sequence of SEQ ID NO: 1 comprising an RGD motif (Arg-Gly-Asp motif) or its fragment on the burn treatment; glaucoma treatment; skin wrinkle reduction; or hair loss prevention, scalp health improvement, or hair growth and hair restoration promotion, and unless otherwise limited herein, it is deemed that the description of 'composition' as below is equally applied to 'method' and 'use', and the description of 'method' and 'use' is omitted herein to avoid overlapping description.

Hereinafter, the present disclosure is described in detail.

The inventors found out that when administered, a peptide of a particular sequence and structure comprising an RGD motif (Arg-Gly-Asp motif) promotes the collagen production and is effective in the burn treatment, glaucoma treatment, hair growth promotion and skin wrinkle reduction.

The composition according to the present disclosure comprises a peptide consisting of an amino acid sequence of SEQ ID NO: 1 comprising an RGD motif (Arg-Gly-Asp motif) or its fragment.

The peptide consisting of an amino acid sequence of SEQ ID NO: 1 consists of 58 amino acids comprising an RGD amino acid, optionally with a disulfide bond between cysteines in the corresponding peptide, and thus may refer to a peptide with no disulfide bond or with 1 or more disulfide bond between cysteines in the fragment. Preferably, the peptide consisting of an amino acid sequence of SEQ ID NO: may be a polypeptide consisting of 452nd-509th amino acids of ADAM metallopeptidase domain 15 (ADAM 15) (GenBank accession no. AAH14566.1). For example, the peptide consisting of an amino acid sequence of SEQ ID NO: 1 may be HU022, and the HU022 has no disulfide bond between cysteines in the peptide.

The fragment of the peptide consisting of an amino acid sequence of SEQ ID NO: 1 may be a fragment consisting of 3 or more amino acids comprising an RGD motif. Preferably, the peptide fragment may consist of 5 to 45 amino acids comprising an RGD motif. More preferably, the peptide fragment may consist of 9, 12 or 15 amino acids comprising an RGD motif. The RGD motif corresponds to 33rd, 34th, and 35th amino acids in the amino acid sequence of SEQ ID NO: 1. It suffices if the peptide fragment comprises the RGD motif, i.e., 33rd, 34th, and 35th amino acids of SEQ ID NO: 1, that is, the present disclosure is not necessarily limited to the peptide fragment comprising both an RGD motif and its consecutive amino acids. The fragment of the peptide consisting of an amino acid sequence of SEQ ID NO: 1 may have a disulfide bond between cysteines in the fragment. The disulfide bond between cysteines in the fragment is distinguished from a disulfide bond between a cysteine inside the fragment and a cysteine outside the fragment. The disulfide bond between cysteines in the fragment may comprise 0 or more disulfide bonds based on the number of cysteines in the fragment, and optionally may comprise no disulfide bond or 1 or more disulfide bonds, and preferably no disulfide bond or 3 or less disulfide bonds.

Preferably, the fragment of the peptide consisting of an amino acid sequence of SEQ ID NO: 1 may be one of the followings:

1) a fragment consisting of 5-45 amino acids comprising the RGD motif of SEQ ID NO: 1, optionally with no disulfide bond or 3 or less disulfide bonds between cysteines in the fragment;

2) a fragment comprising 30th-38th amino acids in the amino acid sequence of SEQ ID NO: 1, optionally with no disulfide bond or 1 or more disulfide bonds between cysteines in the fragment;

3) a fragment comprising 32nd-43rd amino acids in the amino acid sequence of SEQ ID NO: 1, optionally with no disulfide bond or 1 or more disulfide bonds between cysteines in the fragment;

4) a fragment comprising 30th-44th amino acids in the amino acid sequence of SEQ ID NO: 1, optionally with no disulfide bond or 1 or more disulfide bond between cysteines in the fragment;

5) a fragment comprising 18th-54th amino acids in the amino acid sequence of SEQ ID NO: 1, optionally with no disulfide bond or 1 or more disulfide bonds between cysteines in the fragment; and 6) a fragment comprising 10th-54th amino acids in the amino acid sequence of SEQ ID NO: 1, optionally with no disulfide bond or 1 or more disulfide bonds between cysteines in the fragment.

These fragments comprise the specific amino acid sequence of said 2)-6) and consist of 58 or less amino acids, optionally with a disulfide bond between cysteines in the corresponding fragment. Based on the number of cysteines in the corresponding fragment, the fragments may comprise 0 or more disulfide bonds, and preferably 0 or more and 3 or less disulfide bonds.

More preferably, the fragment of the peptide consisting of an amino acid sequence of SEQ ID NO: 1 may be one of the followings:

1) a fragment consisting of 9, 12 or 15 amino acids comprising the RGD motif of SEQ ID NO: 1, optionally with no disulfide bond or 3 or less disulfide bonds between cysteines in the fragment;

2) a fragment consisting of 30th-38th amino acids in the amino acid sequence of SEQ ID NO: 1;

3) a fragment consisting of 32nd-43rd amino acids in the amino acid sequence of SEQ ID NO: 1, with a disulfide bond between 36th cysteine and 42nd cysteine;

4) a fragment consisting of 30th-44th amino acids in the amino acid sequence of SEQ ID NO: 1, with no disulfide bond between cysteines in the fragment; or 5) a fragment consisting of 30th-44th amino acids in the amino acid sequence of SEQ ID NO: 1, with a disulfide bond between cysteines in the fragment.

According to a specific embodiment of the present disclosure, the 2) fragment may be HU027, which corresponds to SEQ ID NO: 5.

According to a specific embodiment of the present disclosure, the 3) fragment may be HU026, which corresponds to SEQ ID NO: 4.

According to a specific embodiment of the present disclosure, the 4) fragment may be HU025, which corresponds to SEQ ID NO: 3.

According to a specific embodiment of the present disclosure, the 5) fragment may be HU024, which corresponds to SEQ ID NO: 2.

The definition of the "peptide or its fragment" according to the present disclosure encompasses their pharmaceutically acceptable derivatives, and the pharmaceutically acceptable derivatives will be recognized as having or providing the same biological function and/or activity as the peptide or fragment according to the present disclosure, and may comprise a pharmaceutically acceptable salt of the peptide or fragment according to the present disclosure so long as the object of the present disclosure is not breached.

The term "pharmaceutically acceptable salt" as used herein refer to any salt possessing a desired biological and/or physiological activity of the compound, and exhibiting a minimum of unwanted toxicological effects. For the salt, an acid addition salt formed by pharmaceutically acceptable free acid is useful. The acid addition salt is produced by a common method, for example, by dissolving a compound in an excess of acid aqueous solution, and precipitating the salt using a water-miscible organic solvent, for example, methanol, ethanol, acetone or acetonitrile. The compound and the same molar amount of acid or alcohol (e.g., glycol monomethyl ether) in water may be heated, and subsequently the mixture may be evaporated and dried, or the precipitated salt may be filtered by suction. In this instance, the free acid includes inorganic acid and organic acid, and the inorganic acid includes, but is not limited to, hydrochloric acid, hydrobromic acid, phosphoric acid, nitric acid, sulfuric acid and tartaric acid, and the organic acid includes, but is not limited to, methanesulfonic acid, p-toluenesulfonic acid, acetic acid, trifluoroactic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, and hydriodic acid. Furthermore, the pharmaceutically acceptable metal salt may be produced using base. The alkaline metal or alkaline earth metal salt is obtained by, for example, dissolving a compound in an excess of alkaline metal hydroxide or alkaline earth metal hydroxide solution, filtering an undissolved compound salt, and evaporating and drying the residue. In this instance, for the metal salt, particularly, sodium, potassium or calcium salt is suitable for pharmaceutical use, but is not limited thereto. Furthermore, other suitable salt is silver salt, and the silver salt may be obtained by causing a reaction between alkaline metal or alkaline earth metal salt and appropriate silver salt (e.g., silver nitrate). Unless otherwise indicated, the peptide according to the present disclosure or its fragment comprises most of salts of acid or base properties that can exist in the peptide or fragment according to the present disclosure. For example, the pharmaceutically acceptable salt includes sodium, calcium and potassium salts of hydroxyl group, and other pharmaceutically acceptable salt of amino group includes hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts, and can be produced by salt production methods known in the art.

The peptide or its fragment according to the present disclosure may be produced by a variety of methods known in the art, and preferably may be produced by protein synthesis methods (Merrifield, R. B., J. Am. chem. Soc. 85:2149, 1963)

The peptide or its fragment according to the present disclosure has at least one of the following effects:
burn treatment;
glaucoma treatment;
skin wrinkle reduction; or
hair loss prevention, scalp health improvement, or hair growth and restoration promotion.

Furthermore, the peptide or its fragment according to the present disclosure may be provided in the form of a pharmaceutical composition or a cosmetic composition, and the pharmaceutical composition and the cosmetic composition are hereinafter collectively referred to as the "composition according to the present disclosure".

The term "promotion", "reduction" or "treatment" as used herein refers to all activities to improve symptoms or change to better condition by administration of the composition according to the present disclosure. Furthermore, the term "prevention" as used herein refers to all activities to inhibit symptoms or delaying the onset of diseases by administration of the composition according to the present disclosure.

The preferred peptides or their fragment according to the present disclosure for each of the effects are as follows:

Burn Treatment.

The term "burn" as used herein refers to damage that occurs when got burned by gas, liquid, solid or flame of high temperature, and burns may have various symptoms and complications according to the burned width and depth, the contact time with the temperature of objects causing burns, and skin conditions. According to severity of burns, epidermis, dermis and/or hypodermis may be damaged, and skin appendages such as follicles, sweat glands, and glandulae sebaceae may be damaged, and even the fatty layer, ligaments, fasciae, muscles, and bone tissues under the skin layer may be damaged. Furthermore, burns may be accompanied by eschar, redness, pain, swelling, blister, and burning sensation.

The composition for treating burns according to the present disclosure comprises a peptide consisting of an amino acid sequence of SEQ ID NO: 1 comprising an RGD motif (Arg-Gly-Asp motif) or its fragment. Most preferably, the composition may comprise a peptide consisting of an amino acid sequence of SEQ ID NO: 1 with no disulfide bond.

Glaucoma Treatment

The term "glaucoma" as used herein collectively means diseases that have a form of optic nerve atrophy and happen in optic nerve including retinal plexus cells. Glaucoma syndrome includes increased intraocular pressure, vision change, swollen cornea, dazzling, tearing, eyelid spasm, mydriasis, headache, nausea, red eye, low vision, and severe eye pain.

The composition for treating glaucoma according to the present disclosure comprises a peptide consisting of an amino acid sequence of SEQ ID NO: 1 comprising an RGD motif (Arg-Gly-Asp motif) or its fragment.

Preferably, the composition for treating glaucoma according to the present disclosure may comprise a fragment of the peptide consisting of an amino acid sequence of SEQ ID NO: 1 comprising an RGD motif (Arg-Gly-Asp motif).

The fragment of the peptide consisting of an amino acid sequence of SEQ ID NO: 1 comprising an RGD motif (Arg-Gly-Asp motif) is preferably as follows:

1) a fragment consisting of 5-45 amino acids comprising the RGD motif of SEQ ID NO: 1, optionally with no disulfide bond or 3 or less disulfide bonds between cysteines in the fragment;

2) a fragment comprising 30th-38th amino acids in the amino acid sequence of SEQ ID NO: 1, optionally with no disulfide bond or 1 or more disulfide bonds between cysteines in the fragment;

3) a fragment comprising 32nd-43rd amino acids in the amino acid sequence of SEQ ID NO: 1, optionally with no disulfide bond or 1 or more disulfide bonds between cysteines in the fragment;

4) a fragment comprising 30th-44th amino acids in the amino acid sequence of SEQ ID NO: 1, optionally with no disulfide bond or 1 or more disulfide bonds between cysteines in the fragment;

5) a fragment comprising 18th-54th amino acids in the amino acid sequence of SEQ ID NO: 1, optionally with no disulfide bond or 1 or more disulfide bonds between cysteines in the fragment; and 6) a fragment comprising 10th-54th amino acids in the amino acid sequence of SEQ ID NO: 1, optionally with no disulfide bond or 1 or more disulfide bonds between cysteines in the fragment.

More preferably, the fragment of the peptide consisting of an amino acid sequence of SEQ ID NO: 1 may be one of the followings:

1) a fragment consisting of 9, 12 or 15 amino acids comprising the RGD motif of SEQ ID NO: 1, optionally with no disulfide bond or 3 or less disulfide bonds between cysteines in the fragment; or 4) a fragment consisting of 30th-44th amino acids in the amino acid sequence of SEQ ID NO: 1, with no disulfide bond in the fragment.

According to a specific embodiment of the present disclosure, the 4) fragment may be HU025, which corresponds to SEQ ID NO: 3.

Skin Wrinkle Reduction

The term "skin wrinkle" as used herein refers to skin fold arising from aging due to skin degeneration, elasticity reduction and so on.

The composition for reducing skin wrinkles according to the present disclosure comprises a peptide consisting of an amino acid sequence of SEQ ID NO: 1 comprising an RGD motif (Arg-Gly-Asp motif) or its fragment.

Preferably, the composition for reducing skin wrinkles according to the present disclosure may comprise a peptide consisting of an amino acid sequence of SEQ ID NO: 1 with no disulfide bond between cysteines in the peptide.

Alternatively, preferably, the composition for reducing skin wrinkles according to the present disclosure may comprise a peptide fragment consisting of an amino acid sequence of SEQ ID NO: 1 comprising an RGD motif (Arg-Gly-Asp motif).

The fragment of the peptide consisting of an amino acid sequence of SEQ ID NO: 1 comprising an RGD motif (Arg-Gly-Asp motif) is preferably as follows:

1) a fragment consisting of 5-45 amino acids comprising the RGD motif of SEQ ID NO: 1, optionally with no disulfide bond or 3 or less disulfide bonds between cysteines in the fragment;

2) a fragment comprising 30th-38th amino acids in the amino acid sequence of SEQ ID NO: 1, optionally with no disulfide bond or 1 or more disulfide bonds between cysteines in the fragment;

3) a fragment comprising 32nd-43rd amino acids in the amino acid sequence of SEQ ID NO: 1, optionally with no disulfide bond or 1 or more disulfide bonds between cysteines in the fragment;

4) a fragment comprising 30th-44th amino acids in the amino acid sequence of SEQ ID NO: 1, optionally with no disulfide bond or 1 or more disulfide bonds between cysteines in the fragment;

5) a fragment comprising 18th-54th amino acids in the amino acid sequence of SEQ ID NO: 1, optionally with no disulfide bond or 1 or more disulfide bonds between cysteines in the fragment; and 6) a fragment comprising 10th-54th amino acids in the amino acid sequence of SEQ ID NO: 1, optionally with no disulfide bond or 1 or more disulfide bonds between cysteines in the fragment.

More preferably, the fragment of the peptide consisting of an amino acid sequence of SEQ ID NO: 1 may be one of the followings:

1) a fragment consisting of 9, 12 or 15 amino acids comprising the RGD motif of SEQ ID NO: 1, optionally with no disulfide bond or 3 or less disulfide bonds between cysteines in the fragment; or 5) a fragment consisting of 30th-44th amino acids in the amino acid sequence of SEQ ID NO: 1, with a disulfide bond between cysteines in the fragment.

According to a specific embodiment of the present disclosure, the 5) fragment may be HU024, which corresponds to SEQ ID NO: 2.

Hair Loss Prevention, Scalp Health Improvement, or Hair Growth and Hair Restoration Promotion The term "alopecia or hair loss" as used herein refers to weakening hair root, hair thinning, and ultimately loss of hair in areas where hair should be normally present. It is known that hair loss is caused by inherited factors, over-secretion of sexual hormone testosterone, reduced blood flow to follicles, over-secretion of sebum, stress, irregular food timings, air pollution, and excessive exposure to UV, and in most cases, many causes act in combination.

Furthermore, the term "scalp" as used herein is composed of five layers—skin, connective tissue, aponeurosis, loose connective tissue and pericranium, and hair is included in the main structure of scalp.

The composition for hair loss prevention, scalp health improvement, or hair growth and restoration promotion according to the present disclosure comprises a peptide consisting of an amino acid sequence of SEQ ID NO: 1 comprising an RGD motif (Arg-Gly-Asp motif) or its fragment.

Preferably, the composition for treating glaucoma according to the present disclosure may comprise a fragment of the peptide consisting of an amino acid sequence of SEQ ID NO: 1 comprising an RGD motif (Arg-Gly-Asp motif).

The fragment of the peptide consisting of an amino acid sequence of SEQ ID NO: 1 comprising an RGD motif (Arg-Gly-Asp motif) is preferably as follows:

1) a fragment consisting of 5-45 amino acids comprising the RGD motif of SEQ ID NO: 1, optionally with no disulfide bond or 3 or less disulfide bonds between cysteines in the fragment;

2) a fragment comprising 30th-38th amino acids in the amino acid sequence of SEQ ID NO: 1, optionally with no disulfide bond or 1 or more disulfide bonds between cysteines in the fragment;

3) a fragment comprising 32nd-43rd amino acids in the amino acid sequence of SEQ ID NO: 1, optionally with no disulfide bond or 1 or more disulfide bonds between cysteines in the fragment;

4) a fragment comprising 30th-44th amino acids in the amino acid sequence of SEQ ID NO: 1, optionally with no disulfide bond or 1 or more disulfide bonds between cysteines in the fragment;

5) a fragment comprising 18th-54th amino acids in the amino acid sequence of SEQ ID NO: 1, optionally with no disulfide bond or 1 or more disulfide bonds between cysteines in the fragment; and 6) a fragment comprising 10th-54th amino acids in the amino acid sequence of SEQ ID NO: 1, optionally with no disulfide bond or 1 or more disulfide bonds between cysteines in the fragment.

More preferably, the fragment of the peptide consisting of an amino acid sequence of SEQ ID NO: 1 may be one of the followings:

1) a fragment consisting of 9, 12 or 15 amino acids comprising the RGD motif of SEQ ID NO: 1, optionally with no disulfide bond or 3 or less disulfide bonds between cysteines in the fragment;

2) a fragment consisting of 30th-38th amino acids in the amino acid sequence of SEQ ID NO: 1;

3) a fragment consisting of 32nd-43rd amino acids in the amino acid sequence of SEQ ID NO: 1, with a disulfide bond between 36th cysteine and 42nd cysteine;

4) a fragment consisting of 30th-44th amino acids in the amino acid sequence of SEQ ID NO: 1, with no disulfide bond between cysteines in the fragment; or 5) a fragment consisting of 30th-44th amino acids in the amino acid sequence of SEQ ID NO: 1, with a disulfide bond between cysteines in the fragment.

According to a specific embodiment of the present disclosure, the 2) fragment may be HU027, which corresponds to SEQ ID NO: 5.

According to a specific embodiment of the present disclosure, the 3) fragment may be HU026, which corresponds to SEQ ID NO: 4.

According to a specific embodiment of the present disclosure, the 4) fragment may be HU025, which corresponds to SEQ ID NO: 3.

According to a specific embodiment of the present disclosure, the 5) fragment may be HU024, which corresponds to SEQ ID NO: 2.

The composition according to the present disclosure may be prepared in the form of a pharmaceutical composition or a cosmetic composition. The pharmaceutical composition or cosmetic composition may comprise pharmaceutically (or cosmetically) acceptable excipients, disintegrating agents, binding agents, lubricating agents, wetting agents, emulsifying agents, or suspending agents. The composition according to the present disclosure may be used singly or in combination with any convenient vehicle and excipient, and its dosage form may be for single or multiple dose administration.

The composition according to the present disclosure may be administered by a non-oral route when administered.

The composition according to the present disclosure may be solid formulation, semi-solid formulation or liquid formulation. The solid formulation includes, but is not limited to, powder, granule, tablet, capsule, and suppository. The solid formulation comprises, but is not limited to, excipients, flavoring agents, binding agents, preservative agents, disintegrating agents, lubricating agents, and fillers. The semi-solid formulation includes, but is not limited to, cream, lotion, emulsion and liniment, and may be prepared with an addition of suitable coloring agents, flavoring agents, stabilizing agents, thickening agents, and surfactants. The liquid formulation includes, but is not limited to, solutions such as water, alcohol and propylene glycol solution, suspensions and emulsions, and may be prepared with an addition of suitable coloring agents, flavoring agents, stabilizing agents, and thickening agents. For example, the powder may be prepared by simply mixing the active ingredient of the present disclosure with a pharmaceutically acceptable suitable excipient, for example, lactose, starch, and microcrystalline cellulose. The granule may be prepared by mixing the active ingredient of the present disclosure with a pharmaceutically acceptable suitable excipient; and a pharmaceutically acceptable suitable binding agent, for example, polyvinylpyrrolidone and hydroxypropylcellulose, using a wet granulation method using a solvent, for example, water, ethanol, and isopropanol or a dry granulation method using compression. Furthermore, the tablet may be prepared by mixing the granules with a pharmaceutically acceptable suitable lubricating agent, for example, magnesium stearate, and tablet-pressing using a tablet machine. Furthermore, for example, an external preparation to skin may be prepared by common methods for preparing an external preparation to skin involving homogenous mixing of a pharmaceutically acceptable suitable substrate, for example, vaseline and stearylalcohol; a pharmaceutically acceptable suitable surfactant, for example, polysorbate and sorbitan sesquioleate; a pharmaceutically acceptable suitable moisturizing agent, for example, glycerin; a pharmaceutically acceptable suitable solvent; and a flavoring agent, a coloring agent, a stabilizing agent and a thickening agent.

In the composition according to the present disclosure, the peptide according to the present disclosure or its fragment is preferably present in an amount of between 0.01 and 10 wt % per the total weight of the composition. When the content is less than 0.01 wt %, the intended effect (skin wrinkle, burn, glaucoma, and hair loss) cannot be fully exhibited, and when the content is greater than 10 wt %, economic competitive advantage is not profitable in terms of industrial availability when peptide synthesis costs are considered, and immunogenicity leads to initial activity, but efficacy may reduce due to antibodies produced due to repeated administration.

The cosmetic composition according to the present disclosure may be manufactured and used in formulations for base makeup or makeup products, for example, toners, essences, oils, creams, powders, packs, foundations, makeup bases, and sticks. The cosmetic composition may be applied in various phases, for example, liquid phase, cream phase, paste phase and solid phase, and may be manufactured by common cosmetic manufacturing methods. For example, the composition of the present disclosure may be produced as a form of hydrating toners using carbomer, butylene glycol, glycerin, PEG, ethanol, polyoxyethylene hydrogeneated castor oil, triethanolamine and purified water, or may be produced in lotion type, for example, using cetearylalcohol, glyceryl stearate/PEG-100 stearate, polysorbate 60, sorbitan sesquioleate, cetyl octanoate, squalane, apricot kernel oil, butyleneglycol, carbomer, xanthan gum, preservative, purified water and arginine, but the present disclosure is not limited to the exemplary formulations.

The pharmaceutical composition according to the present disclosure may be variously formulated and used as ointments, creams, gels, films, tablets, capsules, granules, suspensions or syrups by common methods known in the technical field to which the present disclosure belongs.

The pharmaceutically effective amount and effective dosage of the pharmaceutical composition according to the present disclosure may vary depending on formulation methods, administration methods, dosing intervals and/or administration routes of the pharmaceutical composition. Furthermore, it may vary depending on many factors including the type and extent of reaction to achieve by administration of the pharmaceutical composition, the type, age, weight, general health conditions, symptoms or severity of diseases, gender, diet, excretion of target individuals, and ingredients of other medical composition used together synchronously or asynchronously for the corresponding individual, and analogous factors well known in the medical field. Those having ordinary skill in the corresponding technical field can easily determine and prescribe the effective dosage for the intended treatment. The pharmaceutical composition according to the present disclosure may be administered in a single or multiple divided doses per day. Accordingly, the dosage does not limit the scope of the present disclosure in any aspect. The desirable dosage of the pharmaceutical composition according to the present disclosure may be from 0.01 mg/kg to 10 mg/kg per day.

In addition to the peptide or its fragment according to the present disclosure, preferably, the composition according to the present disclosure may contain other ingredients to provide synergic effect with the main effect without causing any damage to the intended main effect.

For example, when the composition of the present disclosure is used for hair loss prevention, in order to impart additional functions, adjuvants may be added, for example, antidandruff agents, hair root fortifying agents, hair repair agents, scalp protecting agents and refreshing agents, taking the properties of hair into account. The adjuvants, for example, antidandruff agents, hair root fortifying agents, hair repair agents, scalp protecting agents and refreshing agents, generally added to the composition for hair growth and hair restoration, include, but are not limited to, those commonly used in the art.

Advantageous Effects

Using the peptide or its fragment according to the present disclosure, it is possible to effectively treat burns and glaucoma, obtain an excellent effect in reducing skin wrinkles, and it is effective in the promotion of hair restoration and hair growth as well as the prevention of hair loss, so it can be used for a cosmetic composition and a pharmaceutical composition.

G5: Test article (30 μg/head/day) (SEQ ID NO:1), n=10
G6: Positive control (10 μg/head/day), n=9-10)

Figure 8:
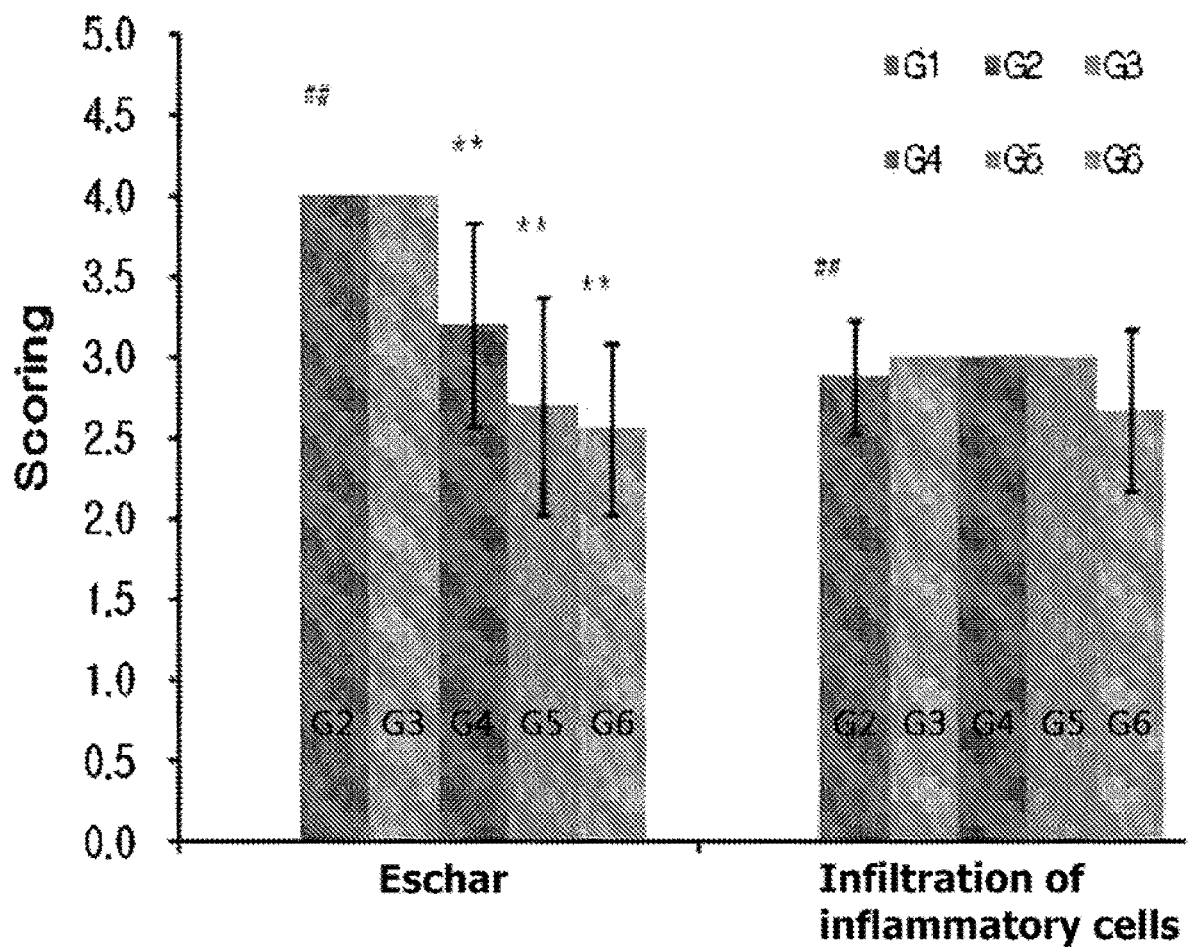

FIG. 8 shows changes in eschar formation and inflammatory cell infiltration of G1-G6.
(G1: Normal control, n=5
G2: Vehicle control, n=9-10
G3: Test article (3.3 μg/head/day) (SEQ ID NO:1), n=10
G4: Test article (10 μg/head/day) (SEQ ID NO:1), n=10
G5: Test article (30 μg/head/day) (SEQ ID NO:1), n=10
G6: Positive control (10 μg/head/day), n=9-10)

Figure 9:
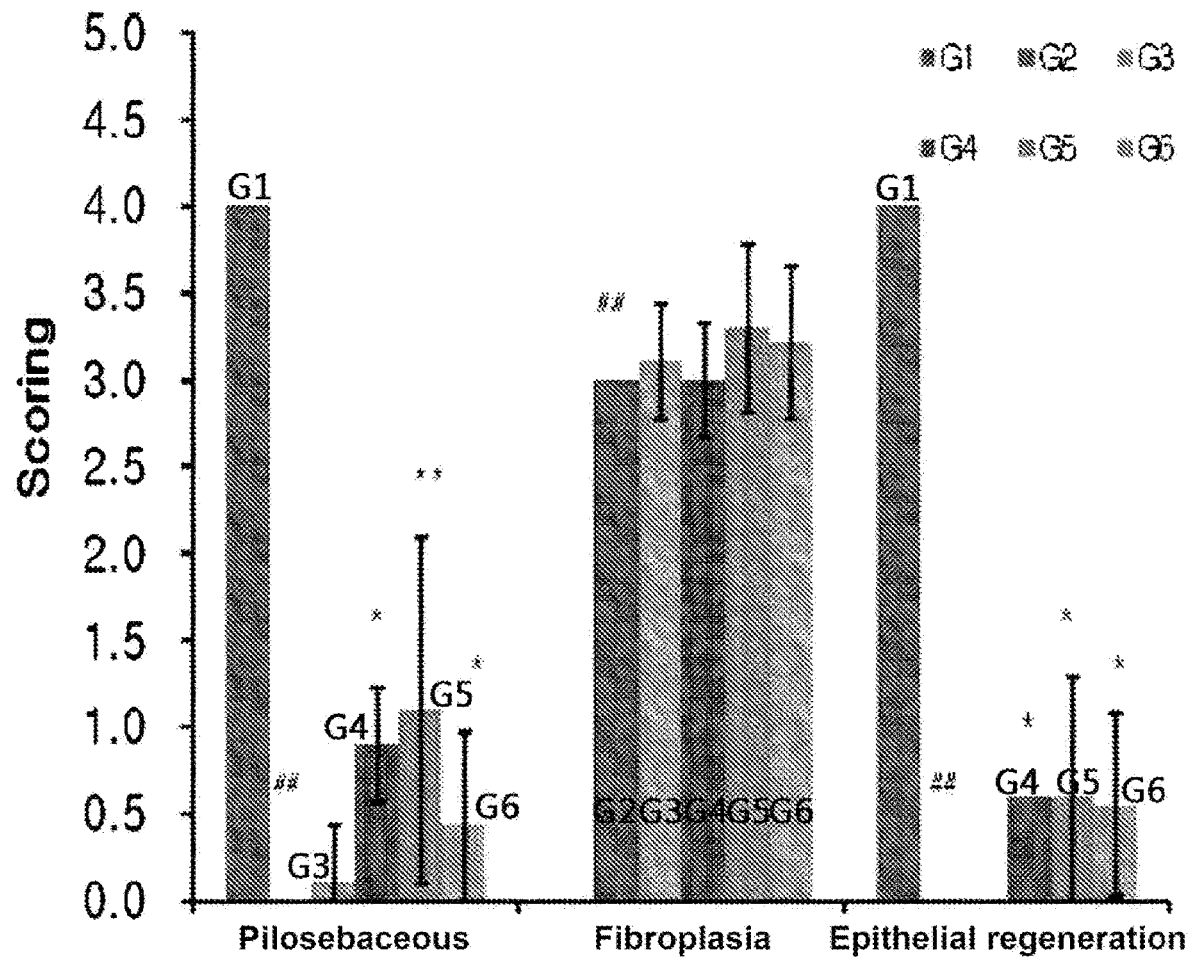

FIG. 9 shows changes in skin appendage regeneration, connective tissue growth, epidermal cell regeneration of G1-G6.
(G1: Normal control, n=5
G2: Vehicle control, n=9-10
G3: Test article (3.3 μg/head/day) (SEQ ID NO:1), n=10
G4: Test article (10 μg/head/day) (SEQ ID NO:1), n=10
G5: Test article (30 μg/head/day) (SEQ ID NO:1), n=10
G6: Positive control (10 μg/head/day), n=9-10)

Figure 10:
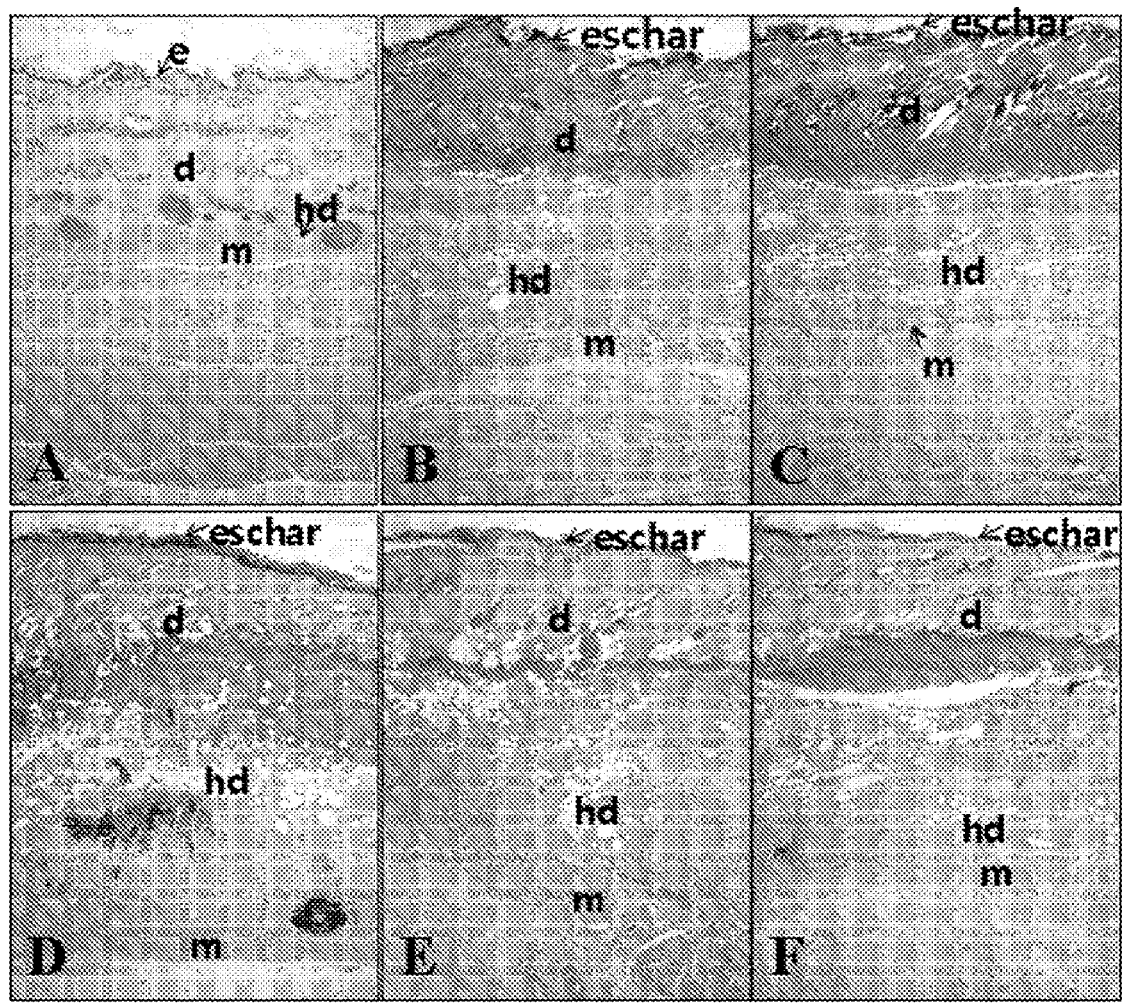

FIG. 10 shows the extent of eschar formation and inflammatory cell infiltration of G1-G6.
(e: epidermis, d: dermis, hd: hypodermis)
(A: Normal control,
B: Vehicle control,
C: Test article (3.3 μg/head/day) (SEQ ID NO:1),
D: Test article (10 μg/head/day) (SEQ ID NO:1),
E: Test article (30 μg/head/day) (SEQ ID NO:1),
F: Positive control (10 μg/head/day))

Figure 11:
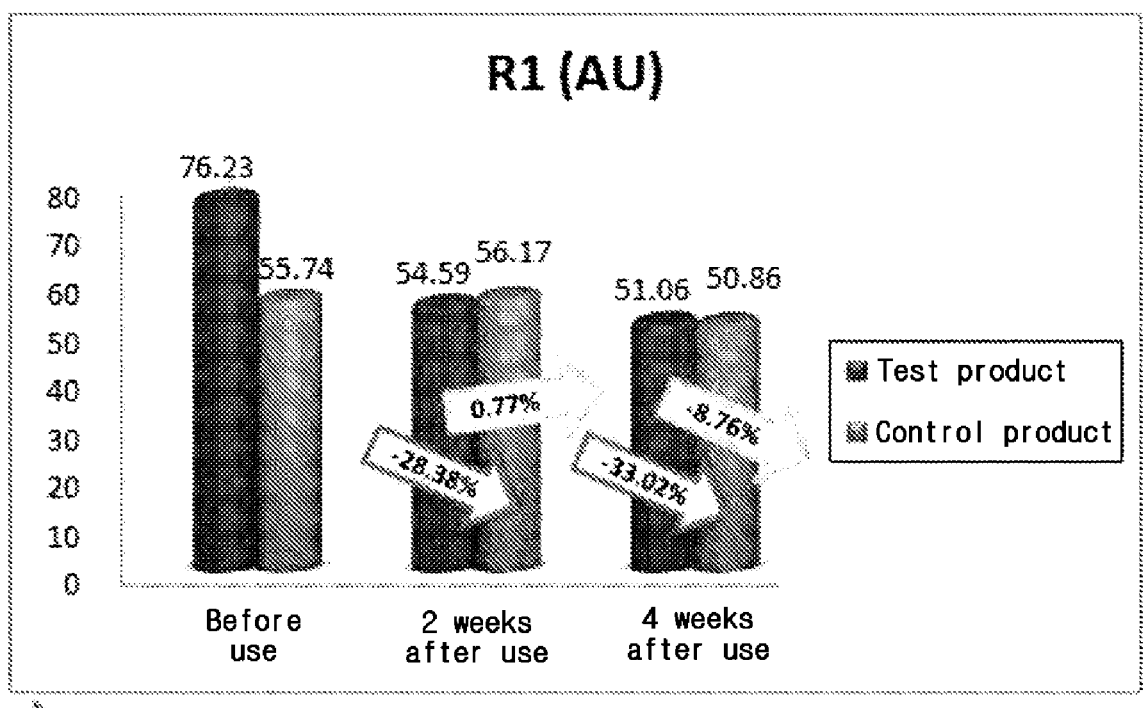

FIG. 11 shows R1 numerical value changes after use of test product (HU022 (SEQ ID NO:1)) and control product.

Figure 12:
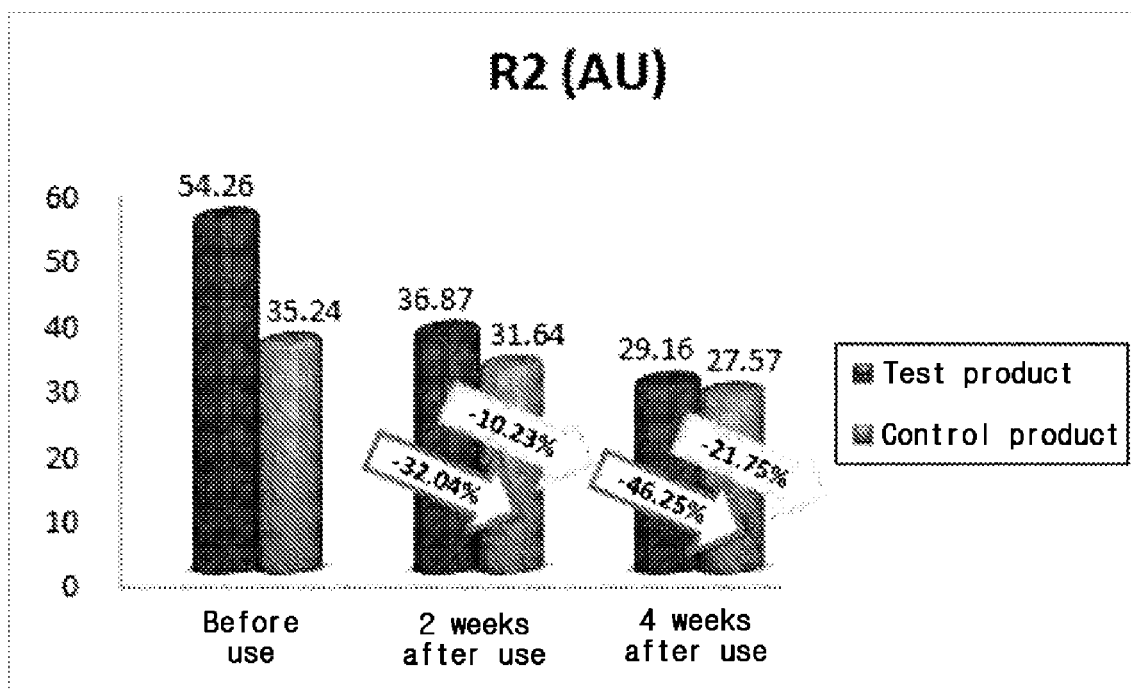

FIG. 12 shows R2 numerical value changes after use of test product (HU022 (SEQ ID NO:1)) and control product.

Figure 13:
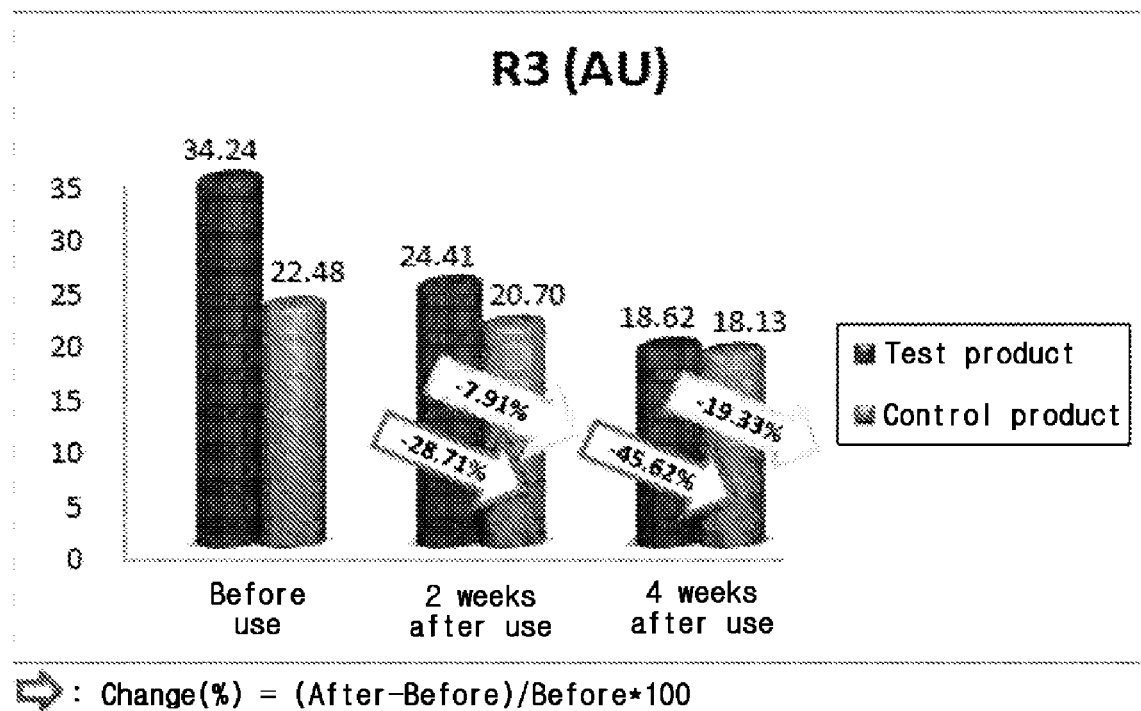

FIG. 13 shows R3 numerical value changes after use of test product (HU022 (SEQ ID NO:1)) and control product.

Figure 14:
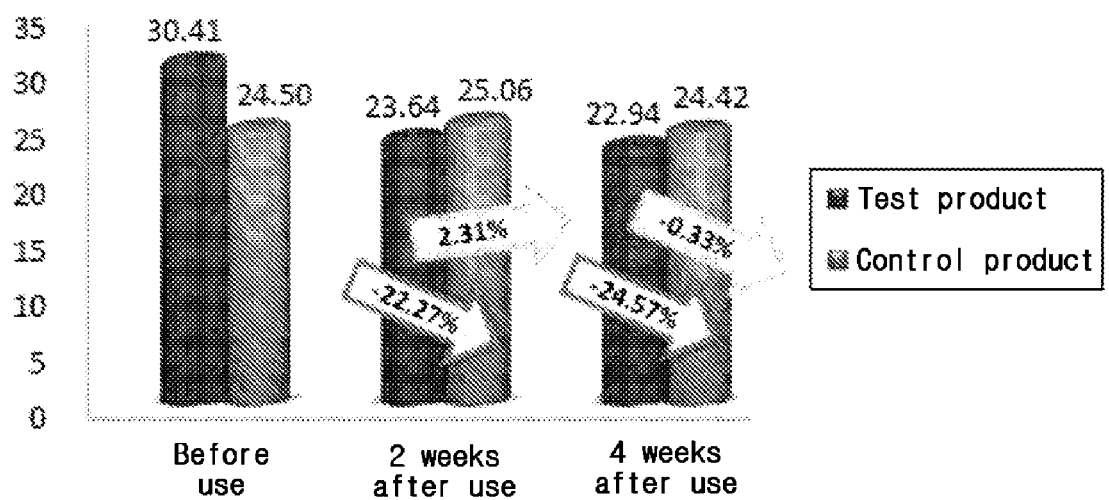

FIG. 14 shows R4 numerical value changes after use of test product (HU022 (SEQ ID NO:1)) and control product.

Figure 15:
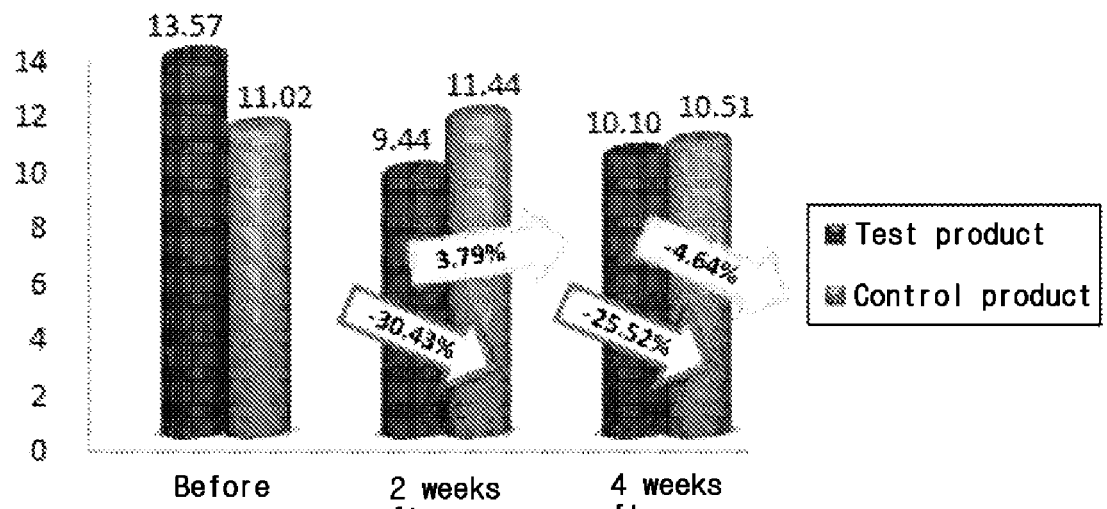

FIG. 15 shows R5 numerical value changes after use of test product (HU022 (SEQ ID NO:1)) and control product.

Figure 16:
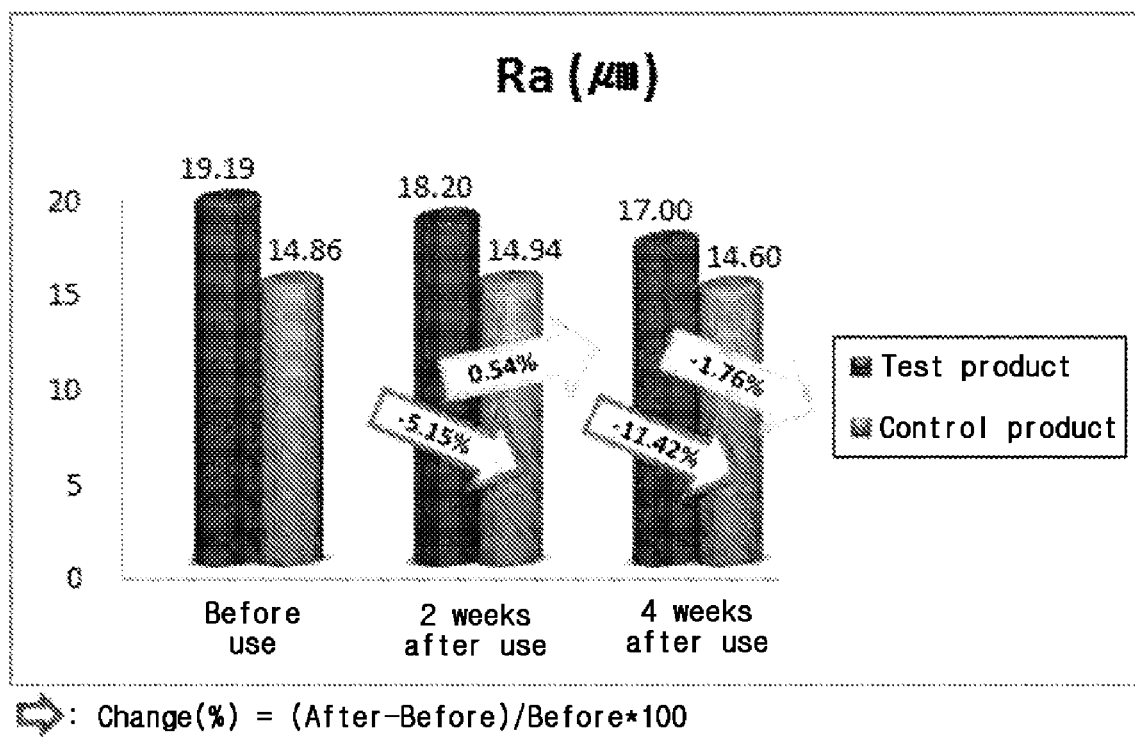

FIG. 16 shows Ra numerical value changes after use of test product (HU022 (SEQ ID NO:1)) and control product.

Figure 17:
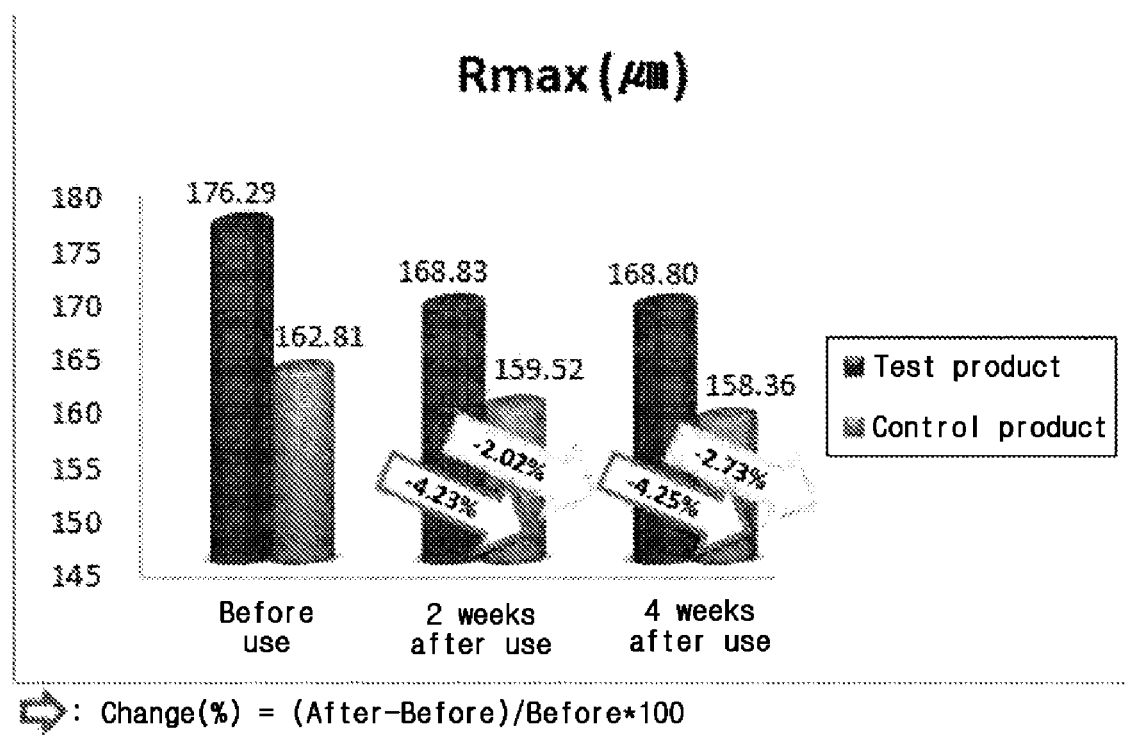

FIG. 17 shows Rmax numerical value changes after use of test product (HU022 (SEQ ID NO:1)) and control product.

Figure 18:
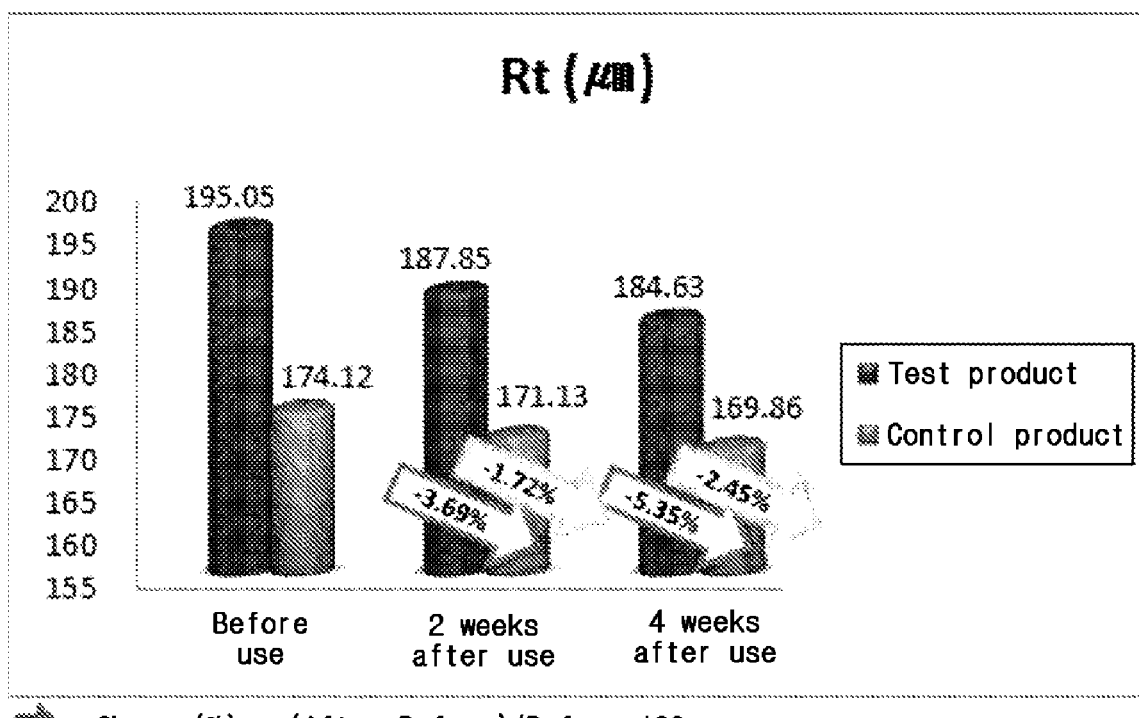

FIG. 18 shows Rt numerical value changes after use of test product (HU022 (SEQ ID NO:1)) and control product.

Figure 19:
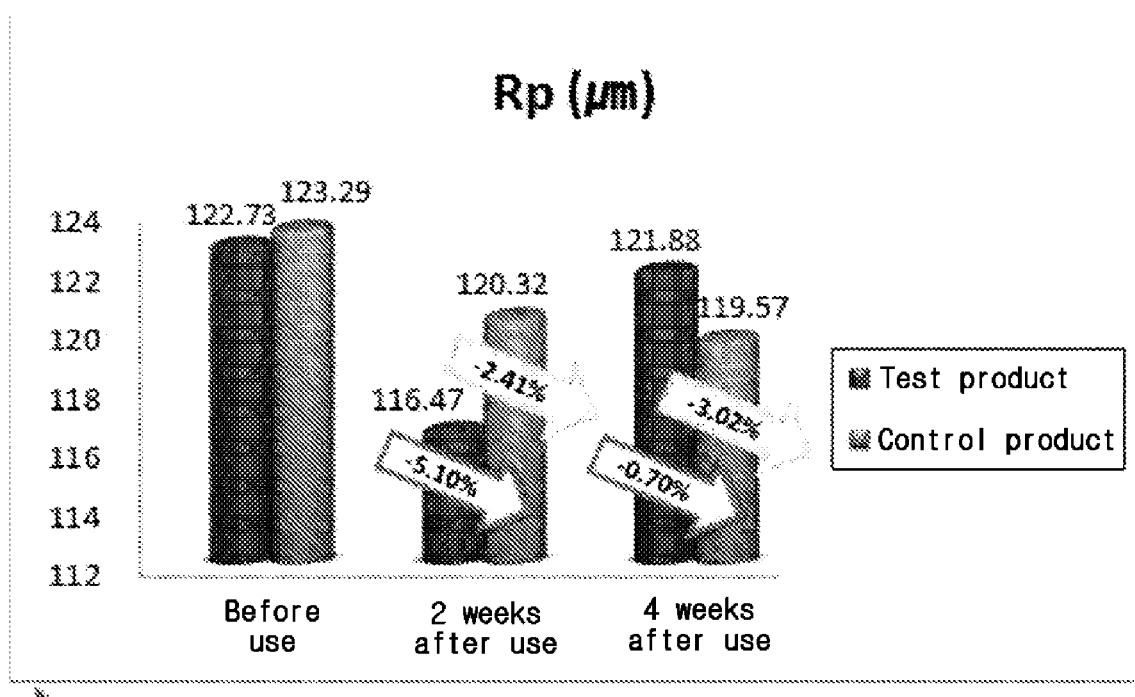

FIG. 19 shows Rp numerical value changes after use of test product (HU022 (SEQ ID NO:1)) and control product.

Figure 20:
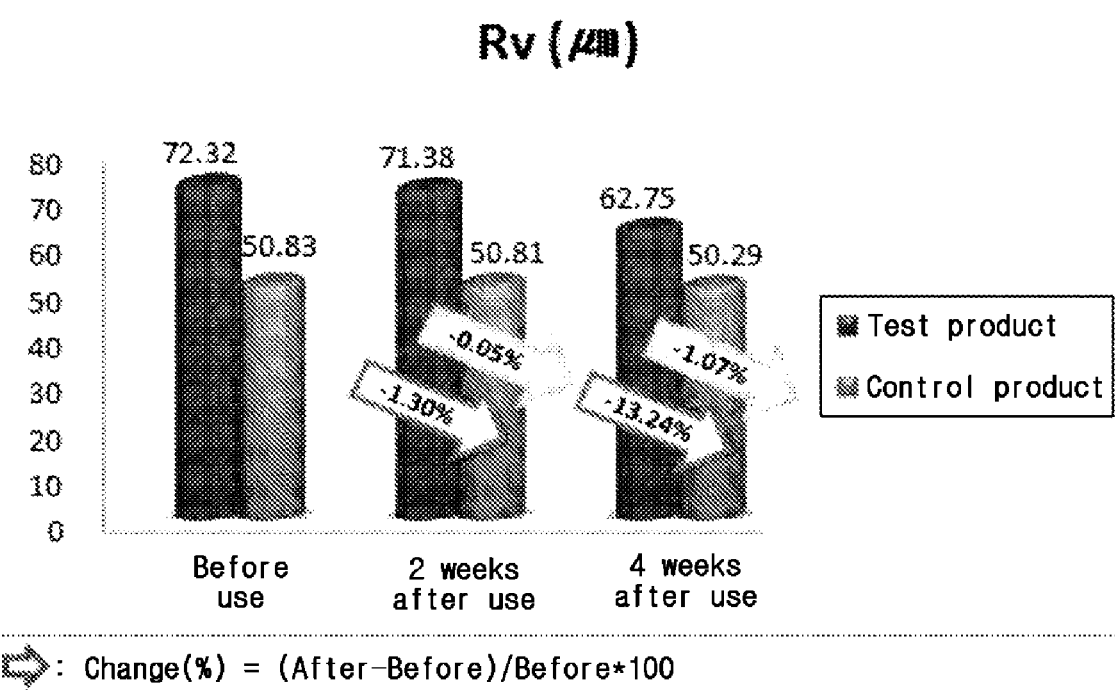

FIG. 20 shows Rv numerical value changes after use of test product (HU022 (SEQ ID NO:1)) and control product.

Figure 21:
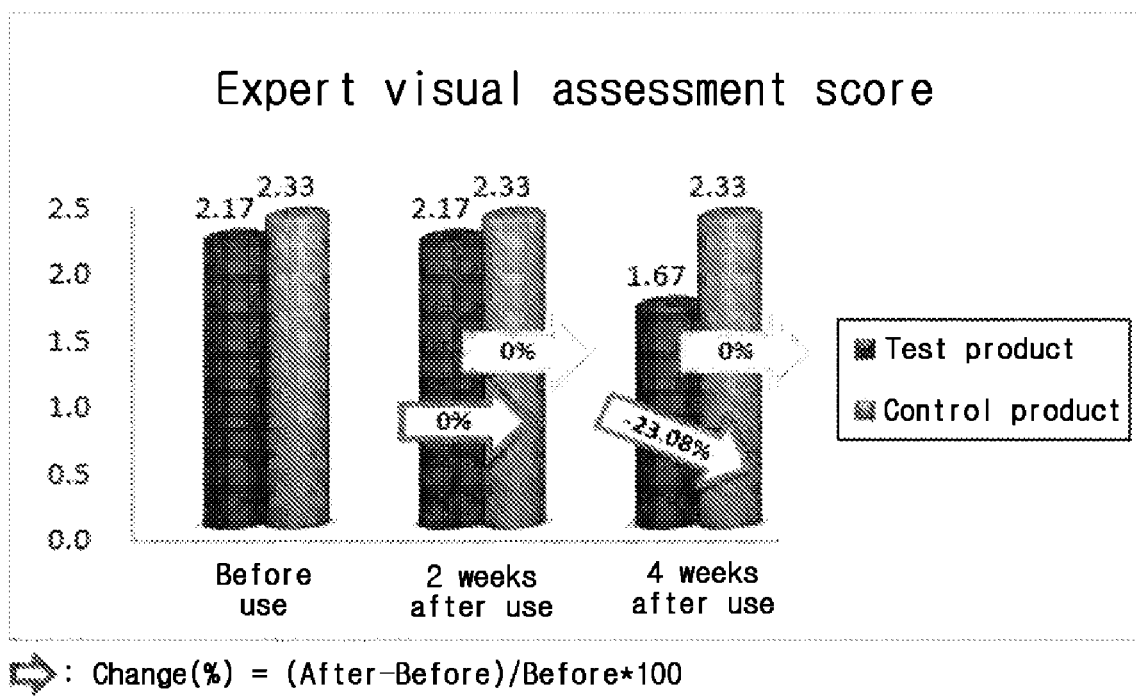

FIG. 21 shows changes in expert visual assessment scores after use of test product (HU022 (SEQ ID NO:1)) and control product.

Figure 22:
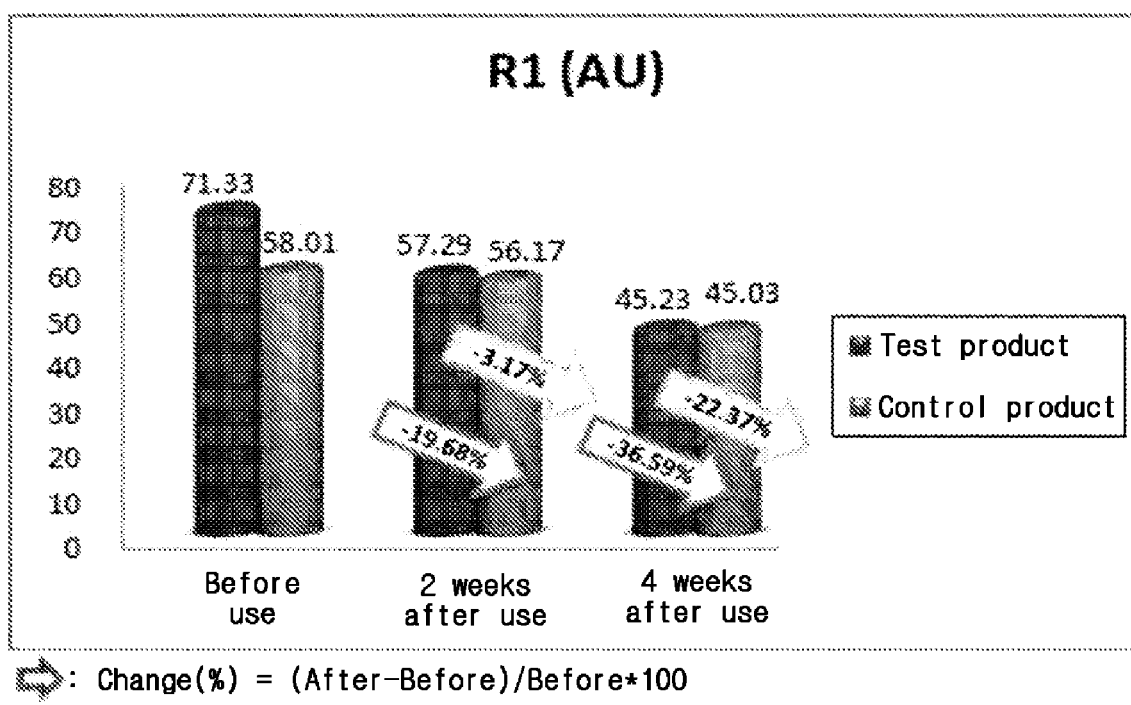

FIG. 22 shows R1 numerical value changes after use of test product (HU024 (SEQ ID NO:2)) and control product.

Figure 23:
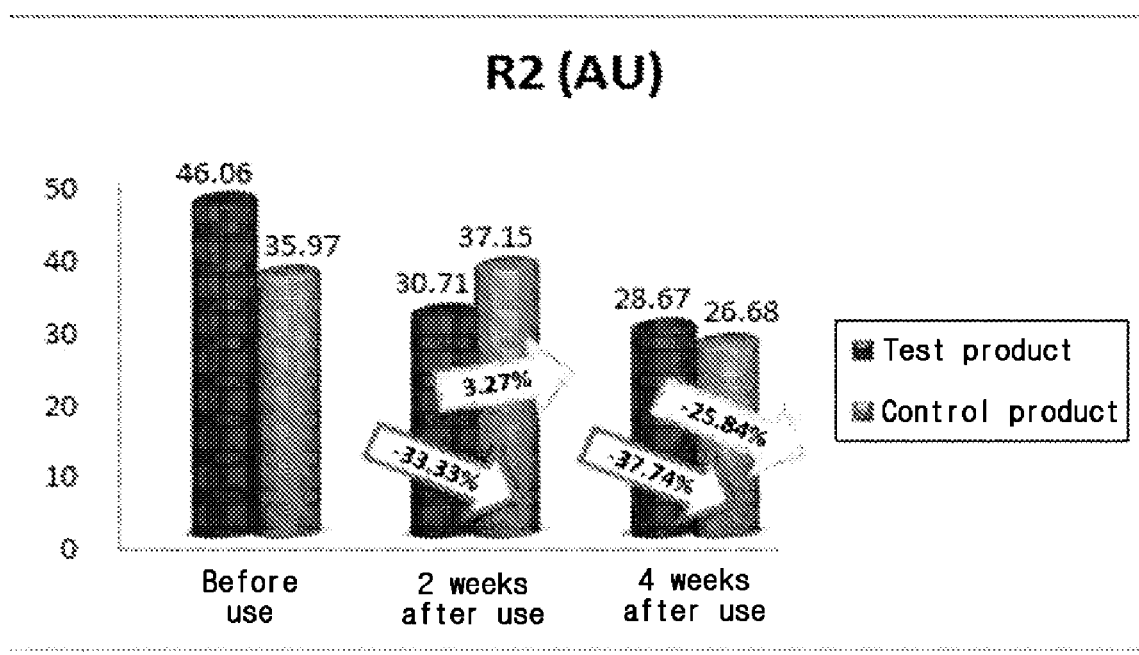

FIG. 23 shows R2 numerical value changes after use of test product (HU024 (SEQ ID NO:2)) and control product.

Figure 24:
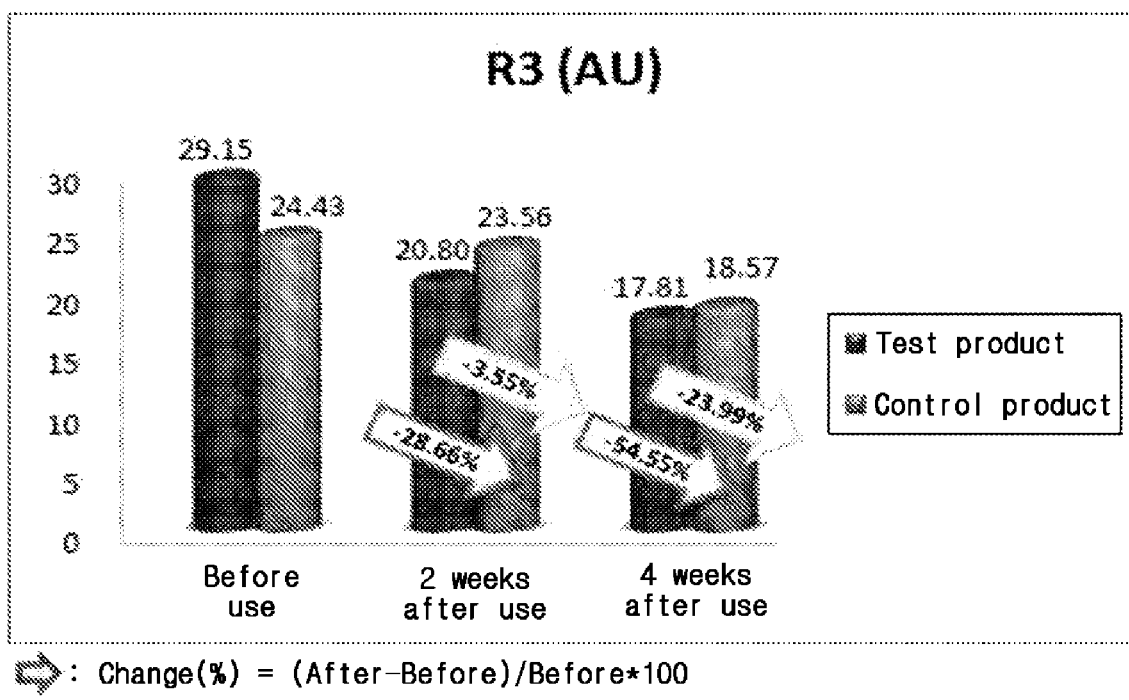

FIG. 24 shows R3 numerical value changes after use of test product (HU024 (SEQ ID NO:2)) and control product.

Figure 25:
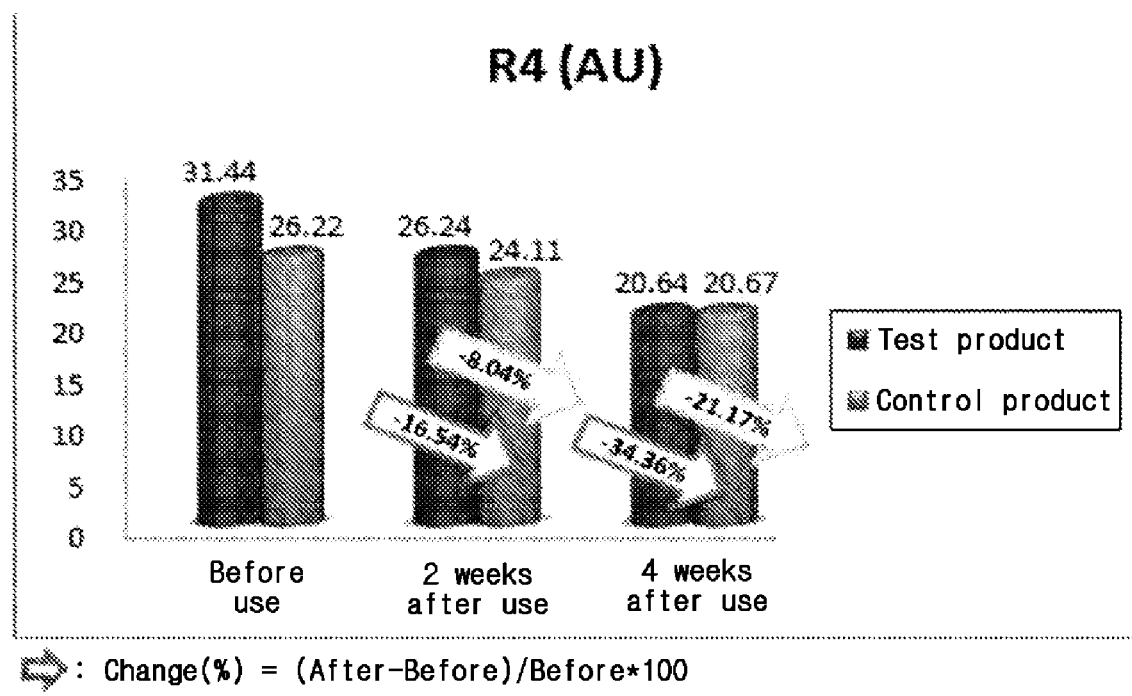

FIG. 25 shows R4 numerical value changes after use of test product (HU024 (SEQ ID NO:2)) and control product.

Figure 26:
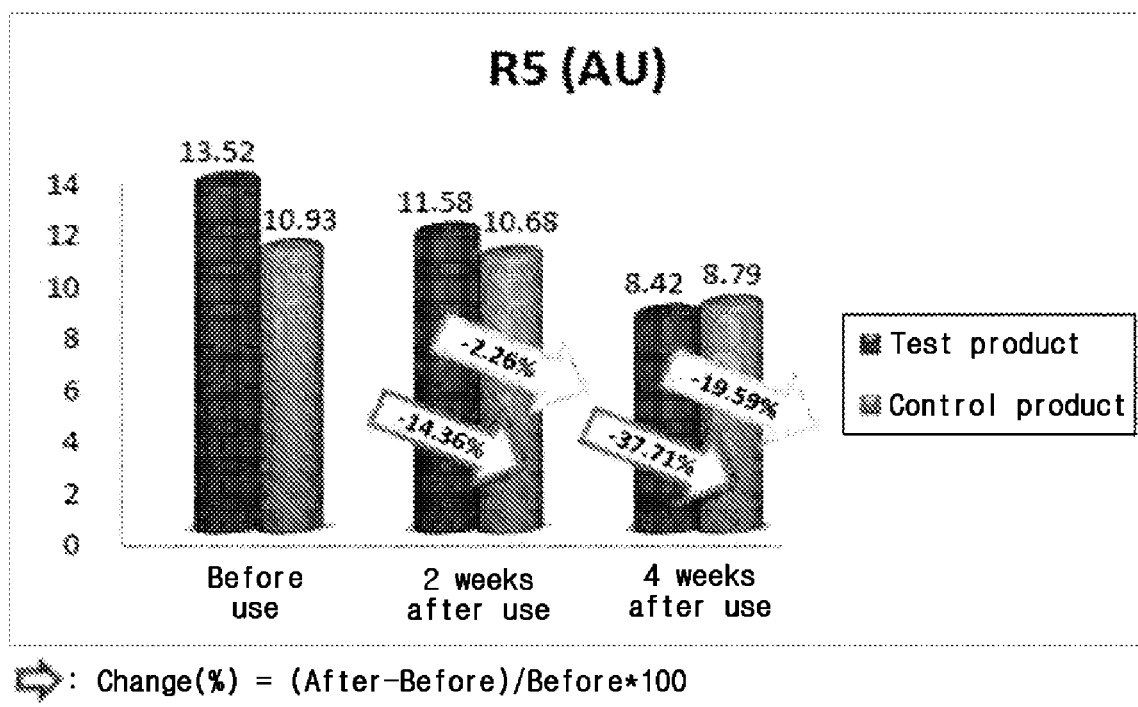

FIG. 26 shows R5 numerical value changes after use of test product (HU024 (SEQ ID NO:2)) and control product.

Figure 27:
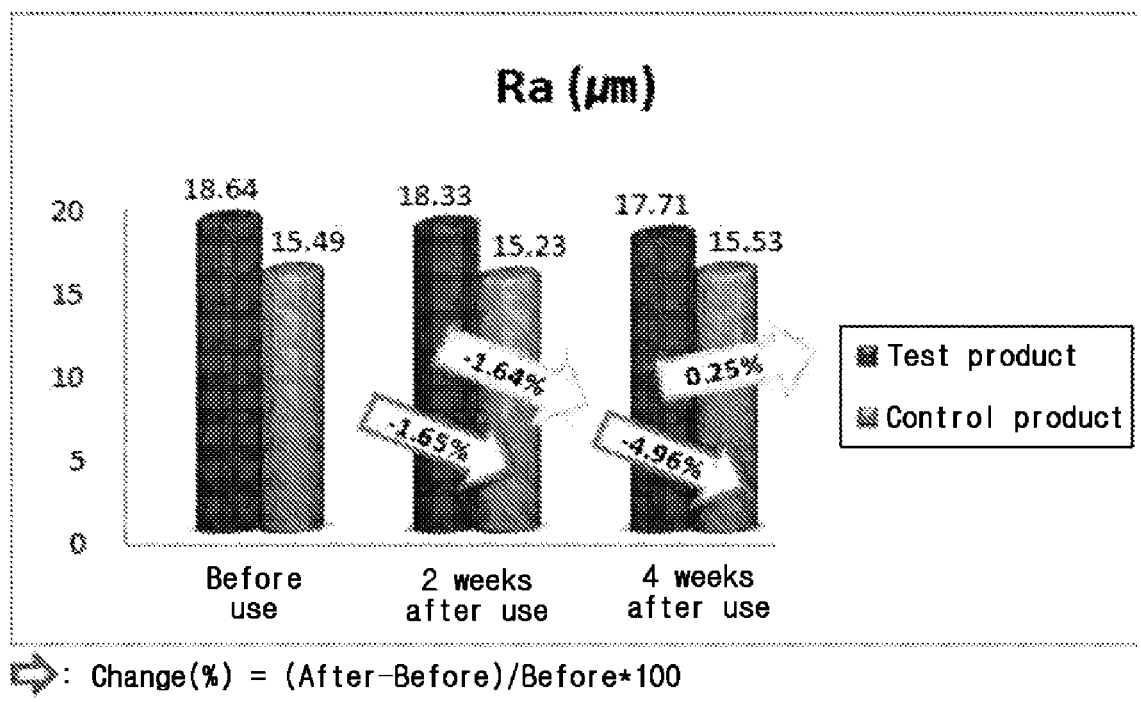

FIG. 27 shows Ra numerical value changes after use of test product (HU024 (SEQ ID NO:2)) and control product.

Figure 28:
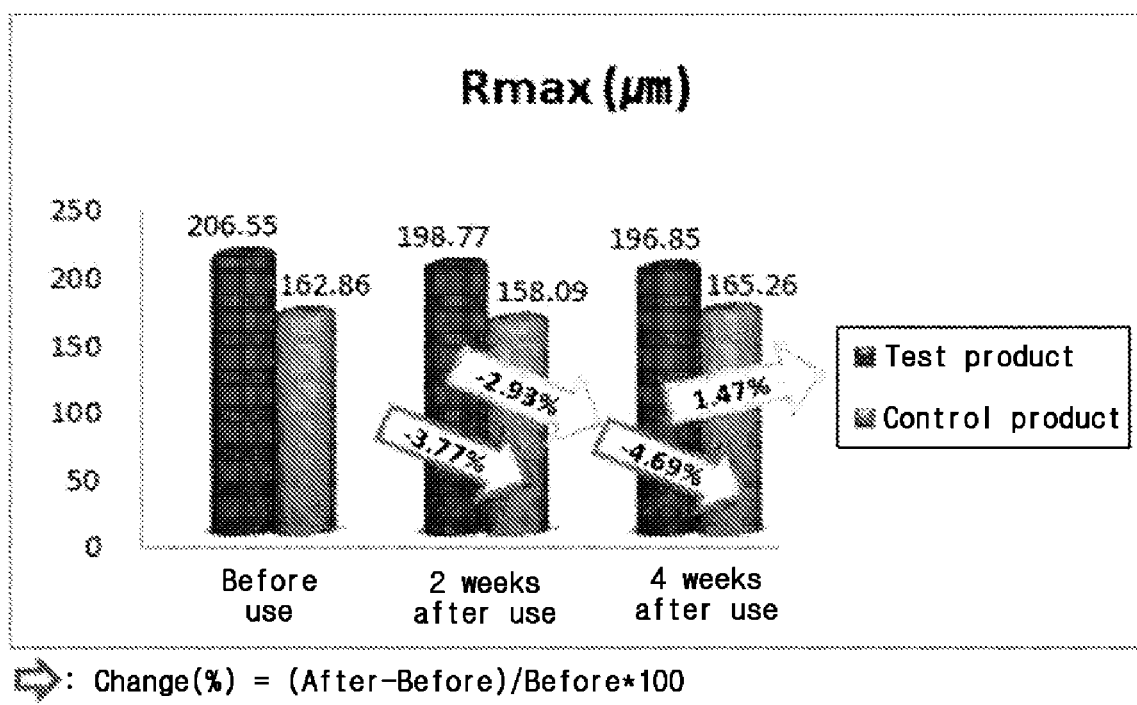

FIG. 28 shows Rmax numerical value changes after use of test product (HU024 (SEQ ID NO:2)) and control product.

Figure 29:
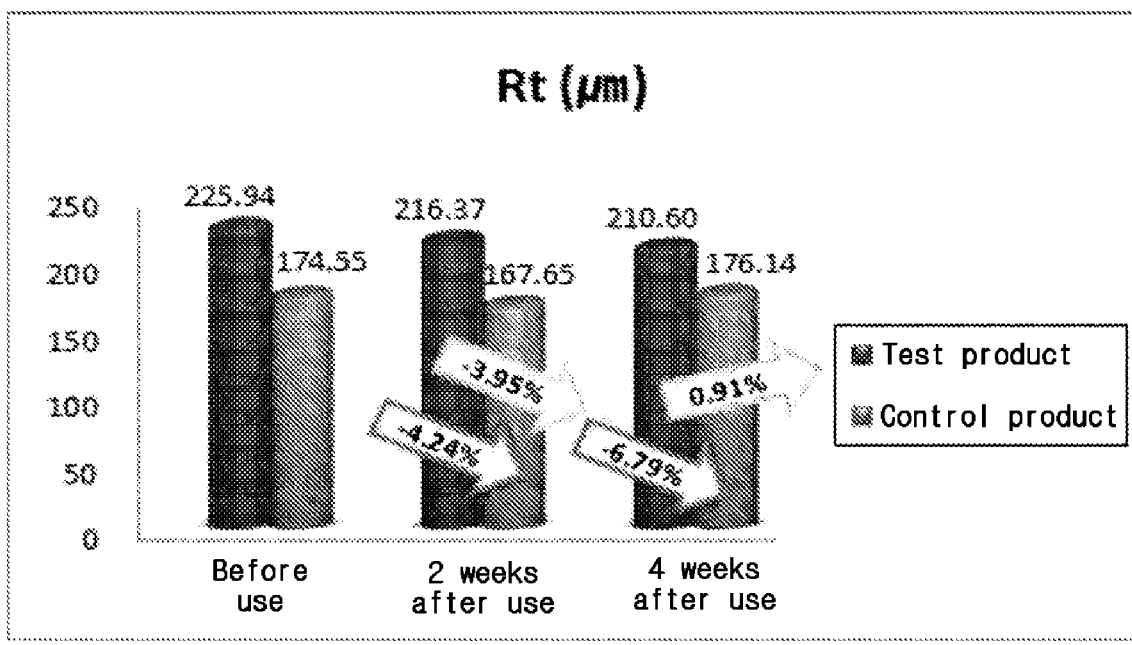

FIG. 29 shows Rt numerical value changes after use of test product (HU024 (SEQ ID NO:2)) and control product.

Figure 30:
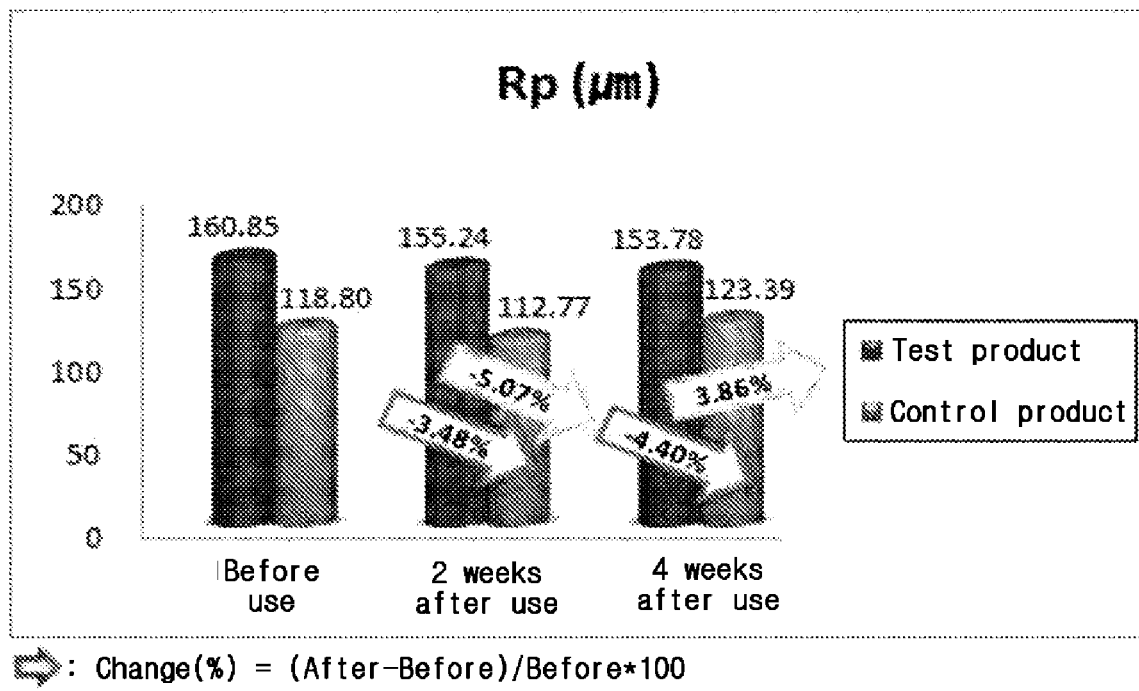

FIG. 30 shows Rp numerical value changes after use of test product (HU024 (SEQ ID NO:2)) and control product.

Figure 31:
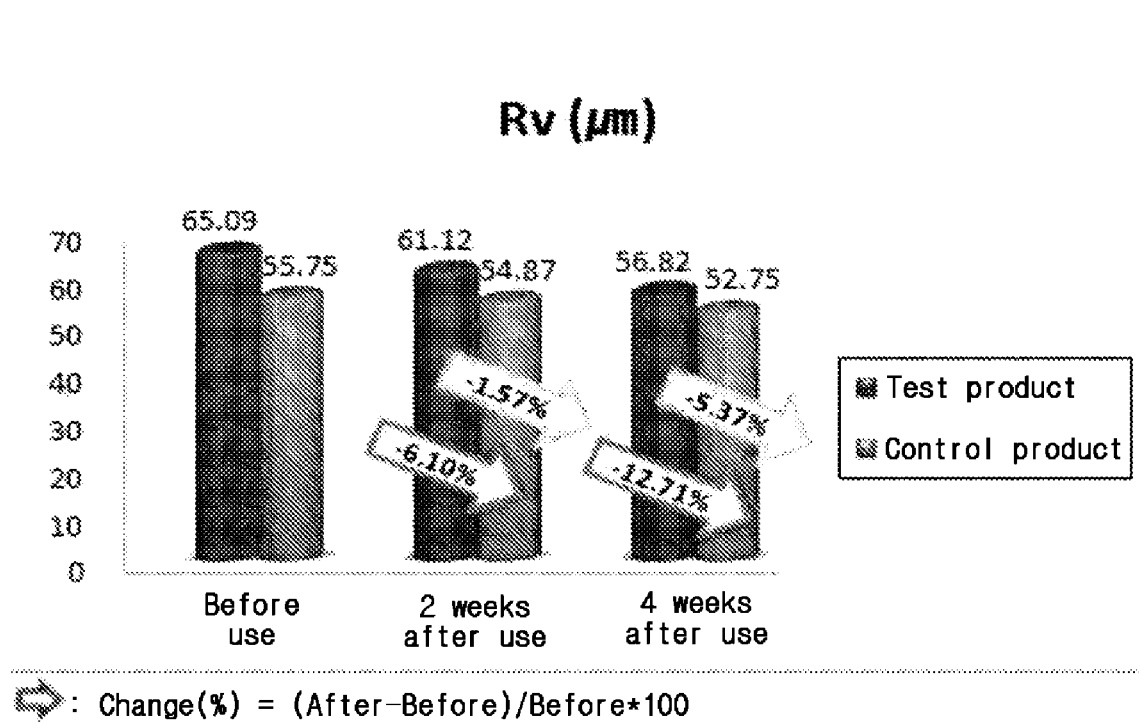

FIG. 31 shows Rv numerical value changes after use of test product (HU024 (SEQ ID NO:2)) and control product.

Figure 32:
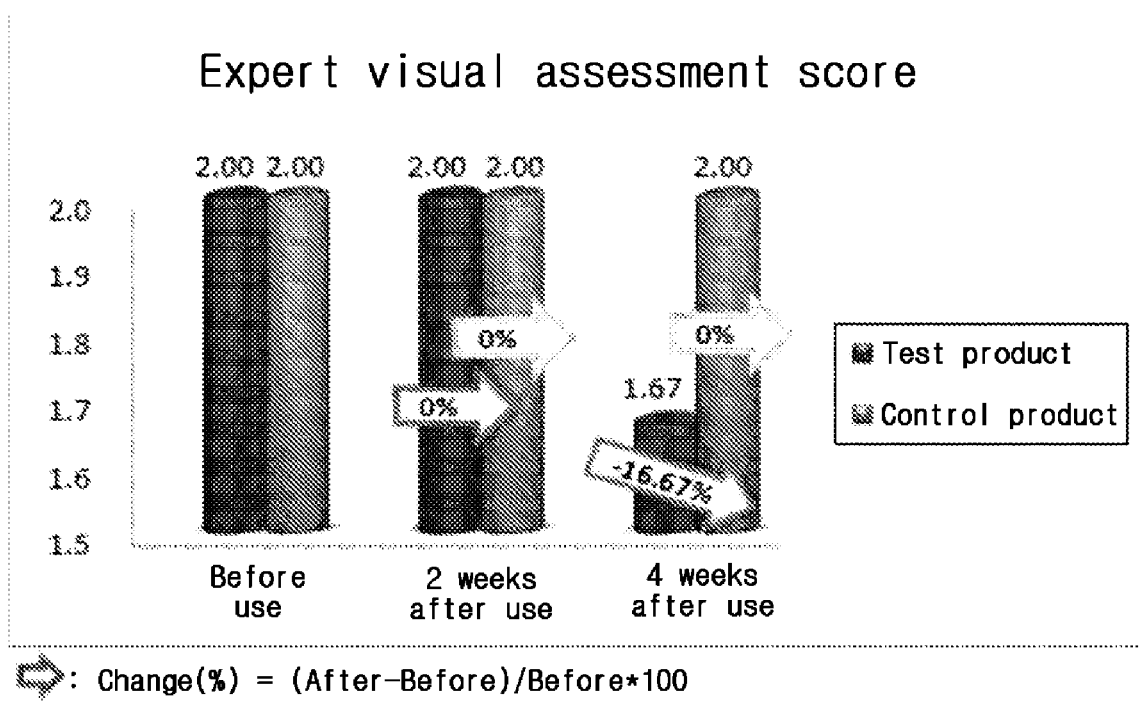

FIG. 32 shows changes in expert visual assessment scores after use of test product (HU024 (SEQ ID NO:2)) and control product.

Figure 33:
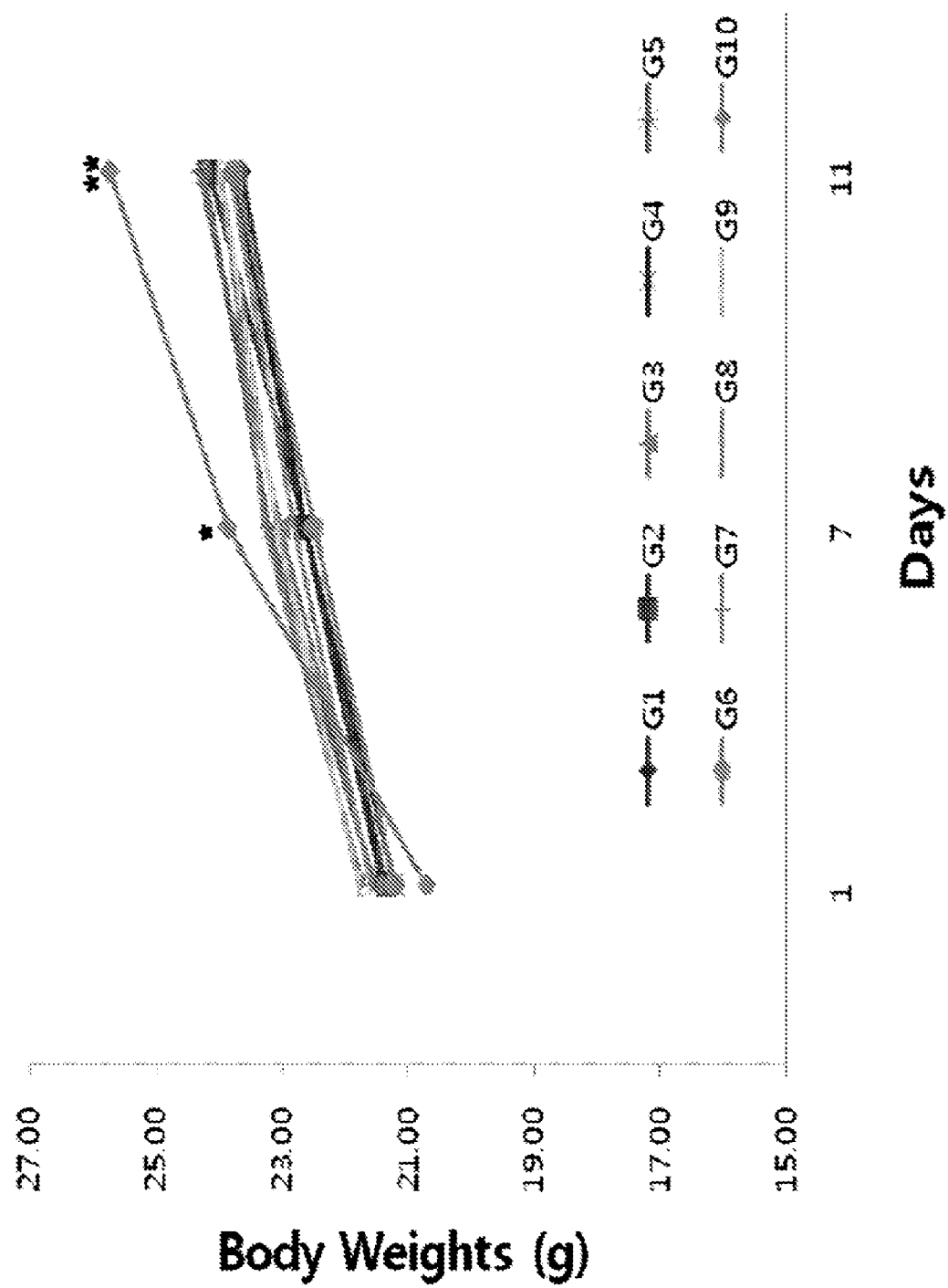

FIG. 33 shows the measurement results of weight changes of G1-G10.
(G1: Vehicle control (Sterile distilled water for Injection), n=10;
G2: Test article I (HU024 (SEQ ID NO:2) 20 ug/head/day), n=10;
G3: Test article I (HU024 (SEQ ID NO:2) 60 ug/head/day), n=10;
G4: Test article II (HU025 (SEQ ID NO:3) 20 ug/head/day), n=10;
G5: Test article II (HU025 (SEQ ID NO:3) 60 ug/head/day), n=10;
G6: Test article III (HU026 (SEQ ID NO:4) 20 ug/head/day), n=10;
G7: Test article III (HU026 (SEQ ID NO:4) 60 ug/head/day), n=10;
G8: Test article IV (HU027 (SEQ ID NO:5) 20 ug/head/day), n=10;
G9: Test article IV (HU027 (SEQ ID NO:5) 60 ug/head/day), n=10;
G10: Reference control (Minoxyl 3%), n=10)

Figure 34:
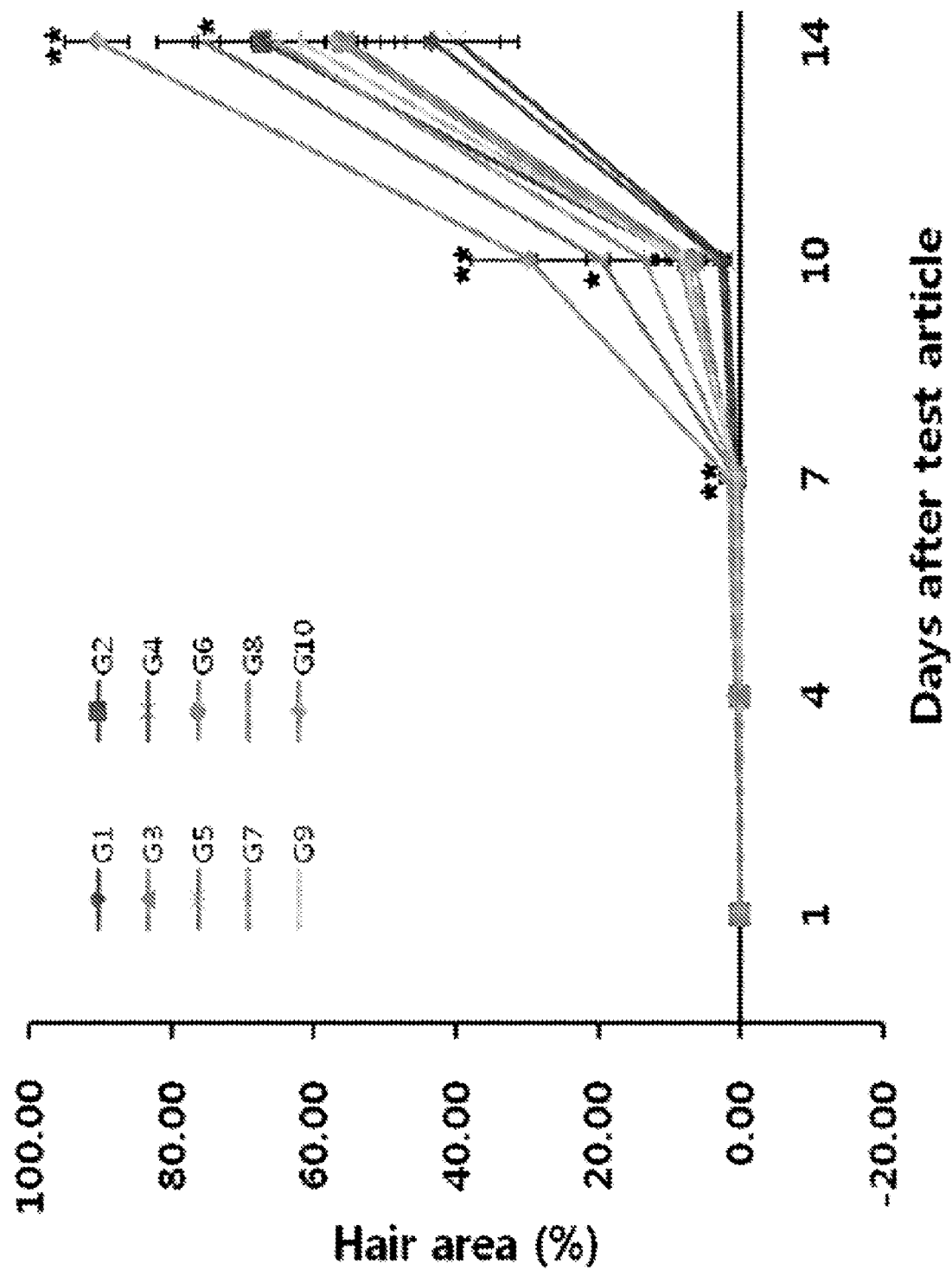

FIG. 34 shows the measurement results of hair area changes of G1-G10.
(G1: Vehicle control (Sterile distilled water for Injection), n=10;
G2: Test article I (HU024 (SEQ ID NO:2) 20 ug/head/day), n=10;
G3: Test article I (HU024 (SEQ ID NO:2) 60 ug/head/day), n=10;
G4: Test article II (HU025 (SEQ ID NO:3) 20 ug/head/day), n=10;
G5: Test article II (HU025 (SEQ ID NO:3) 60 ug/head/day), n=10;
G6: Test article III (HU026 (SEQ ID NO:4) 20 ug/head/day), n=10;
G7: Test article III (HU026 (SEQ ID NO:4) 60 ug/head/day), n=10;
G8: Test article IV (HU027 (SEQ ID NO:5) 20 ug/head/day), n=10;
G9: Test article IV (HU027 (SEQ ID NO:5) 60 ug/head/day), n=10;
G10: Reference control (Minoxyl 3%), n=10)

Figure 35:
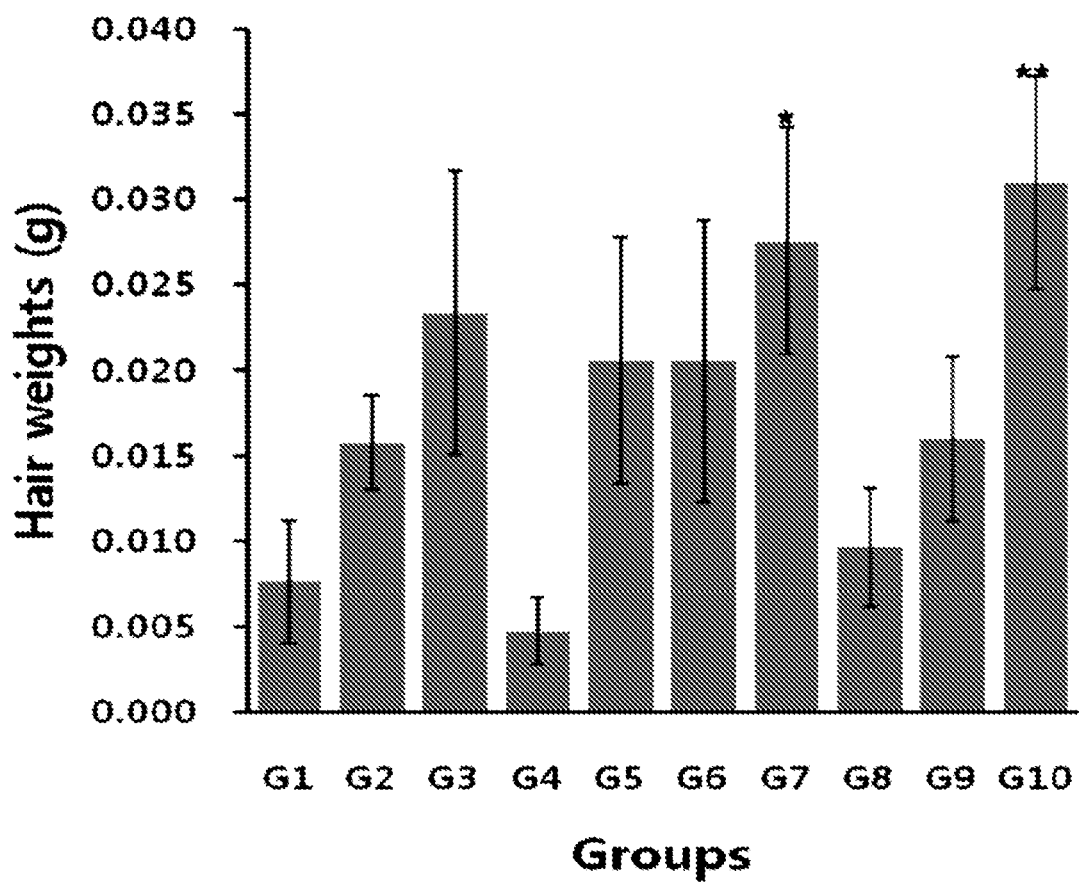

FIG. 35 shows the measurement results of hair weight changes.
(G1: Vehicle control (Sterile distilled water for Injection), n=10;
G2: Test article I (HU024 (SEQ ID NO:2) 20 ug/head/day), n=10;
G3: Test article I (HU024 (SEQ ID NO:2) 60 ug/head/day), n=10;
G4: Test article II (HU025 (SEQ ID NO:3) 20 ug/head/day), n=10;
G5: Test article II (HU025 (SEQ ID NO:3) 60 ug/head/day), n=10;
G6: Test article III (HU026 (SEQ ID NO:4) 20 ug/head/day), n=10;
G7: Test article III (HU026 (SEQ ID NO:4) 60 ug/head/day), n=10;
G8: Test article IV (HU027 (SEQ ID NO:5) 20 ug/head/day), n=10;

G9: Test article IV (HU027 (SEQ ID NO:5) 60 ug/head/day), n=10;

G10: Reference control (Minoxyl 3%), n=10)

Figure 36:
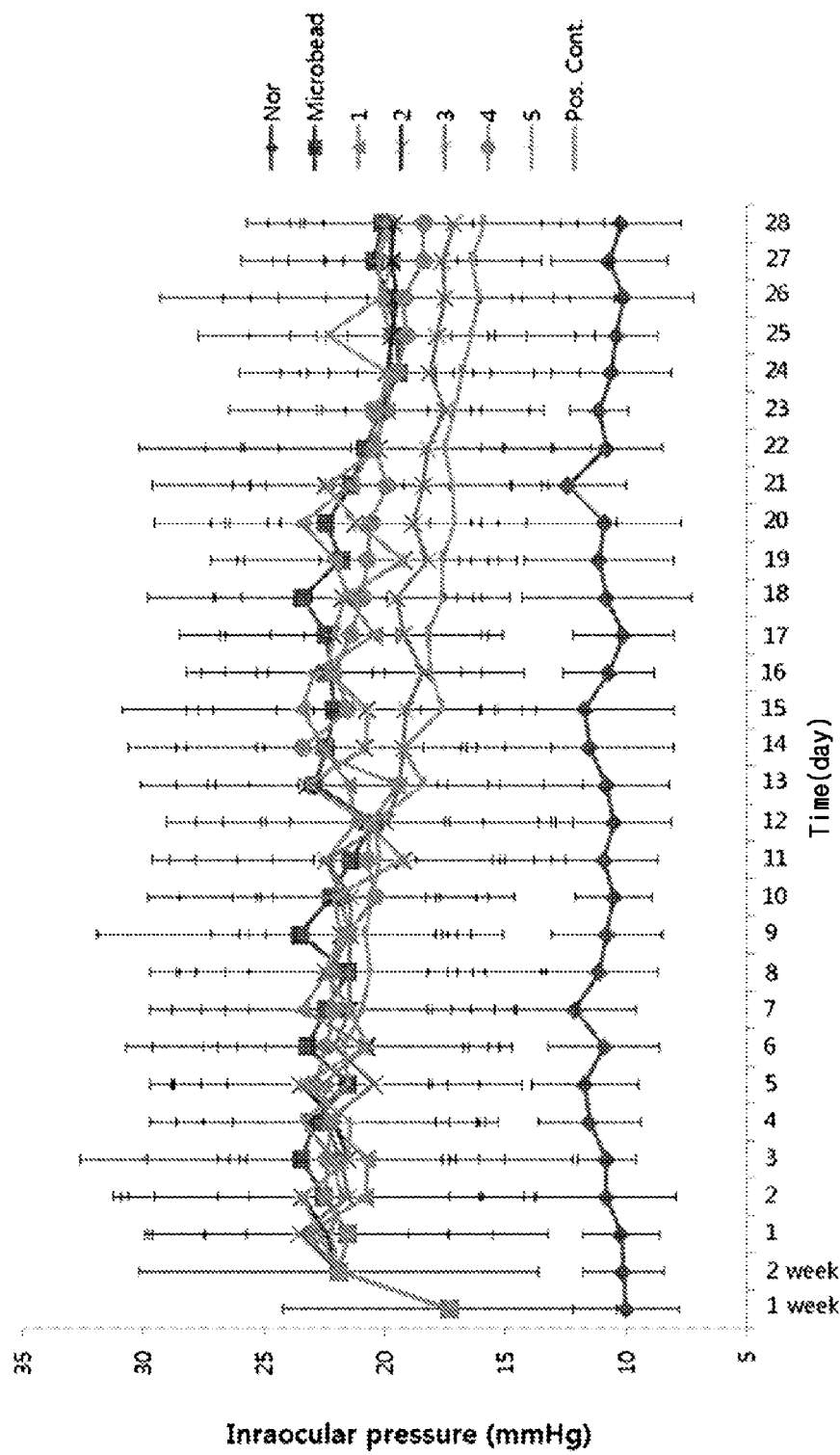

FIG. 36 shows the measurement results of intraocular pressure changes in increased intraocular pressure animal model administered with samples 1-5.

Nor: normal mouse

Microbead: increased intraocular pressure animal model

Sample 1: Tafluprost+HU024 (SEQ ID NO:2) (20 ug/ml)

Sample 2: HU024 (SEQ ID NO:2) (20 ug/ml)

Sample 3: HU025 (SEQ ID NO:3) (20 ug/ml)

Sample 4: HU026 (SEQ ID NO:4) (20 ug/ml)

Sample 5: HU027 (SEQ ID NO:5) (20 ug/ml)

Pos Cont: Tafluprost

Figure 37:
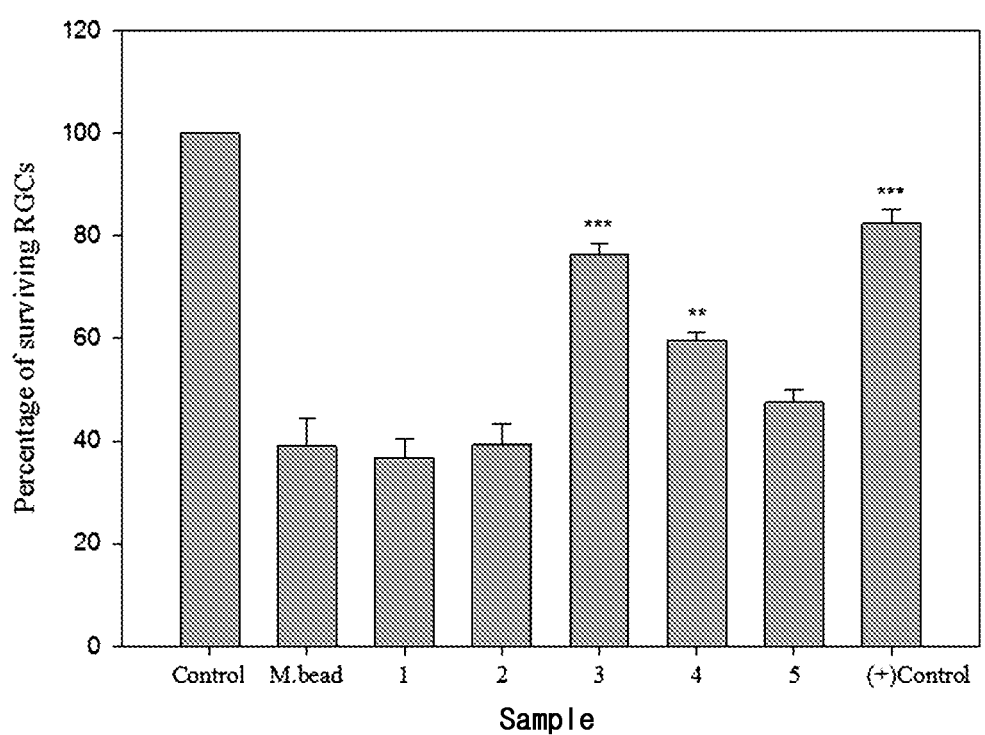

FIG. 37 shows the measurement results of changes of optic nerve cells in increased intraocular pressure animal model administered with samples 1-5.

Control: normal mouse

Microbead: increased intraocular pressure animal model

Sample 1: Tafluprost+HU024 (SEQ ID NO:2) (20 ug/ml)

Sample 2: HU024 (SEQ ID NO:2) (20 ug/ml)

Sample 3: HU025 (SEQ ID NO:3) (20 ug/ml)

Sample 4: HU026 (SEQ ID NO:4) (20 ug/ml)

Sample 5: HU027 (SEQ ID NO:5) (20 ug/ml)

(+)Control: Tafluprost

BEST MODE FOR CARRYING OUT THE INVENTION

Hereinafter, the present disclosure will be described in further detail through examples. These examples are intended to describe the present disclosure in more detail, and it is obvious to persons having ordinary skill in the art that the scope of the present disclosure is not limited to the scope of disclosure of the examples.

Example 1. Synthesis of Peptide

A polypeptide consisting of 452nd-509th amino acids of ADAM metallopeptidase domain 15 (ADAM 15) (GenBank accession no. AAH14566.1) is designated as HU022 (SEQ ID NO: 1), and comprises a portion of disintegrin.

Furthermore, a peptide consisting of a total of 15 amino acids that is designed to surround an RGD motif in the disintegrin region of ADAM15 protein (NCBI Reference Sequence: NM_001261464), comprise cysteines playing a key role in the 3-dimensional (3D) structure with the RGD motif centered. The peptide is designed to have a disulfide bond formed between cysteines, and is designated as HU024 (SEQ ID NO: 2).

Furthermore, a peptide designed to have the same amino acid sequence as HU024 (SEQ ID NO:2), but no disulfide bond, is designated as HU025 (SEQ ID NO: 3).

Furthermore, additionally, a peptide in a smaller size that is designed to surround an RGD motif in the disintegrin region of ADAM15 protein, consisting of 12 amino acids, is designated as HU026 (SEQ ID NO: 4), and consisting of 9 amino acids, is designated as HU027 (SEQ ID NO: 5).

Hereinafter, a method for producing the peptides is described in more detail.

For synthesis of a new peptide comprising an RGD motif according to the present disclosure, a solid phase peptide synthesis method (solid—phase method) was used (Merrifield, R. B., J. Am. Chem. Soc. 85:2149, 1963). Target peptides HU024 (SEQ ID NO:2), HU025 (SEQ ID NO:3), HU026 (SEQ ID NO:4), HU027 (SEQ ID NO:5) were synthesized on Rink amide MBHA resin using Fmoc chemistry, and the amino acid used was those having N-terminal and side chains protected using 9-fluorenylmethoxycarbonyl group. An amount of amino acids used in synthesis was 0.3 mmol that is 3 equivalents of 0.1 mmol resin. In coupling at each step, reaction was performed with an addition of DIC (N,N'-Diisoprpyl Cabodiimide) as a reagent for the activation of C-terminal and CI-HOBt (6-Chloro-1-hydroxybenzotriazole) as a reagent for suppressing the racemization in a sequential order according to each sequence, and the Fmoc group of the peptides was removed by treatment with 50% Piperidine/DMF (50/50,v/v) solution at room temperature for 10-20 minutes. After peptide synthesis was completed, for release from solid phase and deprotection of side chain, treatment with TFA (Trifluoroacetic acid)/water mixed solution (9.5/0.5,v/v) was performed at room temperature for 2 hours. For disulfide bond formation in the peptide, a high dilution air oxidation method was used to form S—S bonds in molecules. To accelerate the reaction, a catalytic amount of DMSO was used.

The synthesized peptide was separated by HPLC using reverse phase C18 column, and 95% or more of purity was confirmed by HPLC for analysis. Also, the molecular weight of each peptide was confirmed by MALDI-TOF (matrix-associated laser desorption ionization) mass analysis method (FIG. 1, FIG. 2, FIG. 3 and FIG. 4).

The amino acid sequences and characteristics of the synthesized polypeptide are listed in Table 1.

TABLE 1

| Name (Sequence number) | Sequences | Characteristics |
|---|---|---|
| HU024 (Sequence number 2) | NH$_2$—RPTRGDCDLPEFCPG—COOH | 15 aa, 1662.8Da, pI 4.56 Disulfide bond: 1 |
| HU025 (Sequence number 3) | NH$_2$–RPTRGDCDLPEFCPG–COOH | 15 aa, 1662.8Da, pI 4.56 Disulfide bond: 0 |
| HU026 (Sequence number 4) | NH$_2$—TRGDCDLPEFCP—COOH | 12 aa, 1352.5Da, pI 4.03 Disulfide bond: 1 |
| HU027 (Sequence number 5) | NH$_2$–RPTRGDCDL–COOH | 9 aa, 1032.1Da, pI 5.95 Disulfide bond: None Free Cystein |

Furthermore, for target peptide HU022 (SEQ ID NO:1), the commercial product (EYEGENE Inc.) was used.

Example 2. Burn Treatment Effect

The experiment was carried out with 55 male SD (Sprague-Dawley) rats that were divided into five groups: 5 rats for normal group (1 group, G1), 9-10 rats for negative control (1 group, G2), 30 rats for experimental group (3 groups, 10 rats in each group, G3, G4, G5), and 9-10 rats for positive control (1 group, G6). In the remaining groups except normal group, burned male SD rats was used for experiment. After SD rats were anesthesized, 2-degree burns, 2 cm in diameter, were induced on the SD rats using an aluminum electric soldering iron.

Test substance HU022 (SEQ ID NO:1) (G3, G4, G5), normal saline solution (G2) and Fiblast (G6) were applied to the skin of the burned male SD rats repeatedly once a day seven times a week for 7 days. Fiblast was applied to control group (G6) in 10 μg/dose/head, and the experimental group was divided into 3 groups and test substance was applied to each group in 3.3 μg/dose/head (G3), 10 μg/dose/head (G4), and 30 μg/dose/head (G5).

After burn was induced, imaging was performed before test substance was applied, and imaging was performed on 1st, 4th, 8th, 11th, and 15th days, and after imaging, test substance was applied and the applied site was covered with gauze and wrapped with tegaderm. Furthermore, images taken for measuring the burn wound area were analyzed using Image analyzer program.

On the 14th day after burn, the burn site on the back was scraped from the dermis and fixed in 10% neutrally buffered formalin solution, and histopathology test was conducted through H&E staining. The skin tissue was observed with optical microscope (Olympus BX41, Olympus, Japan), and histological changes related to burn treatment in epidermis, dermis, hypodermis, and subcutaneous muscles were analyzed for each of the following six items: 1) eschar, (0, none; 1+, mild; 2+, moderate; 3+ severe; 4+, very severe), 2) infiltration of inflammatory cells (0, none; 1+, epidermis infiltration; 2+, dermis infiltration; 3+, hypodermis infiltration, 4+, muscle infiltration), 3) angiogenesis (randomly selecting 3 zones at a magnification of ×400, and counting and averaging the number of all blood vessels observed), 4) skin appendage regeneration (pilosebaceous), (0, none; 1+, the extent of regeneration is low; 2+, regeneration is observed at several zones; 3+, regeneration of appendages is normal in shape, but the number is less than normal; 4+; the same level as normal group), 5) connective tissue growth (fibroplasia) (0, normal group level; 1+, only observed in some areas of the dermis or hypodermis; 2+, observed in the dermis and hypodermis; 3+, observed over a wide area of the dermis and hypodermis; 4+, observed over the entire burn wound area), 6) epidermal regeneration (0, regeneration is not observed; 1+, basal cells are observed as a layer in some areas; 2+, basal cells are observed in row, 3+, basal cells are observed as a layer or multiple layers in most regions of damaged skin and the spinous layer or granular layer is identified, 4+, normal group epidermis structure), and after assessment, averages were calculated for each group.

With the measurement results, parametric comparison determined significance via Student's t-test and One-Way ANOVA, and significance testing relative to negative control was conducted. Furthermore, with the histopathology test results of burns, Kruskal-Wallis' H-test was conducted, and when significance between groups was identified, comparison between groups was performed through Mann-Whitney U-test. The computation program for statistics was SPSS 10.1 K. $P<0.05$ was determined to be statistically significant.

Figure 1:
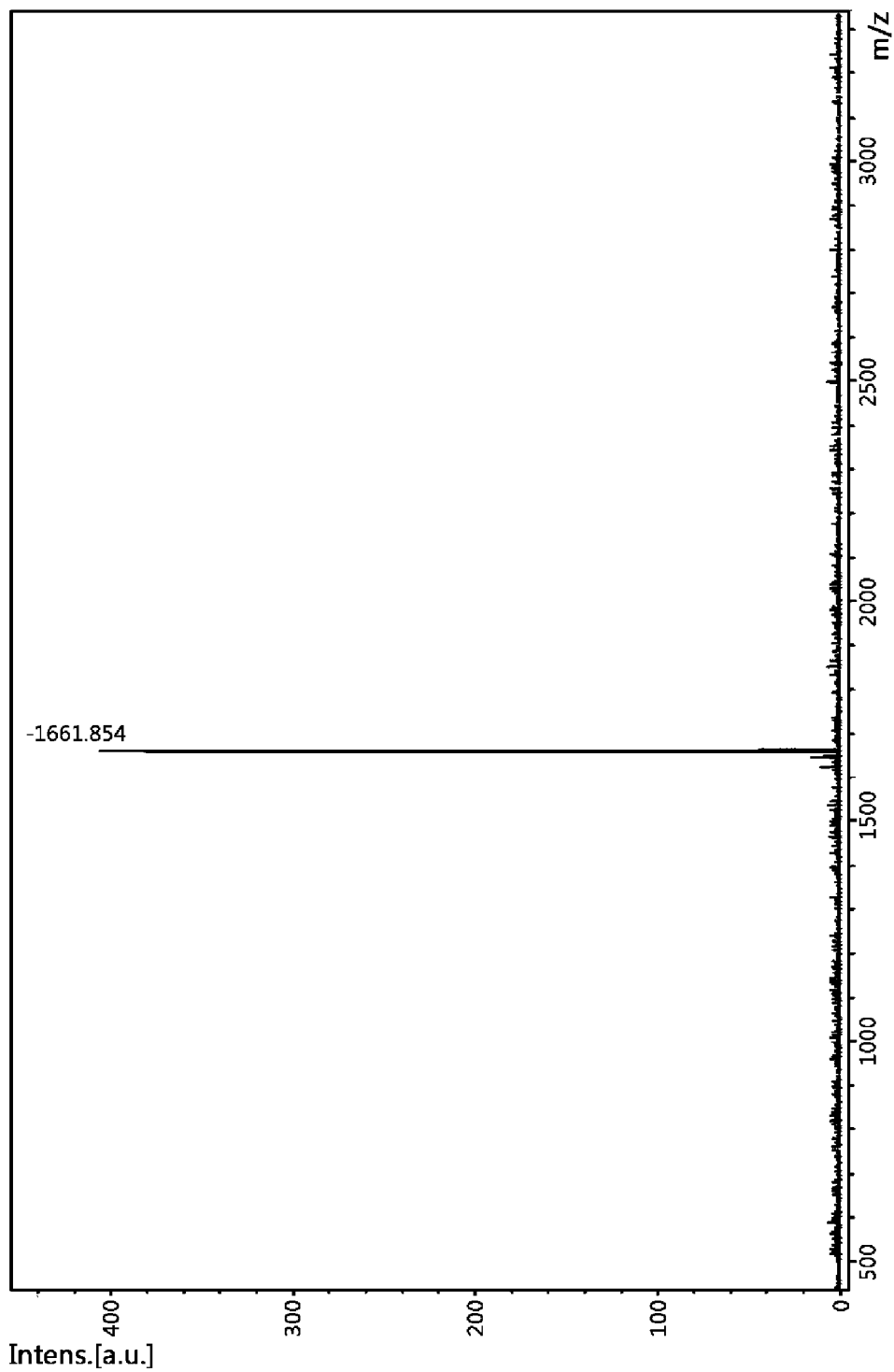
FIG. 1 shows the results of HU024 (SEQ ID NO:2) measured by the MALDI-TOF mass analysis method.
Figure 2:
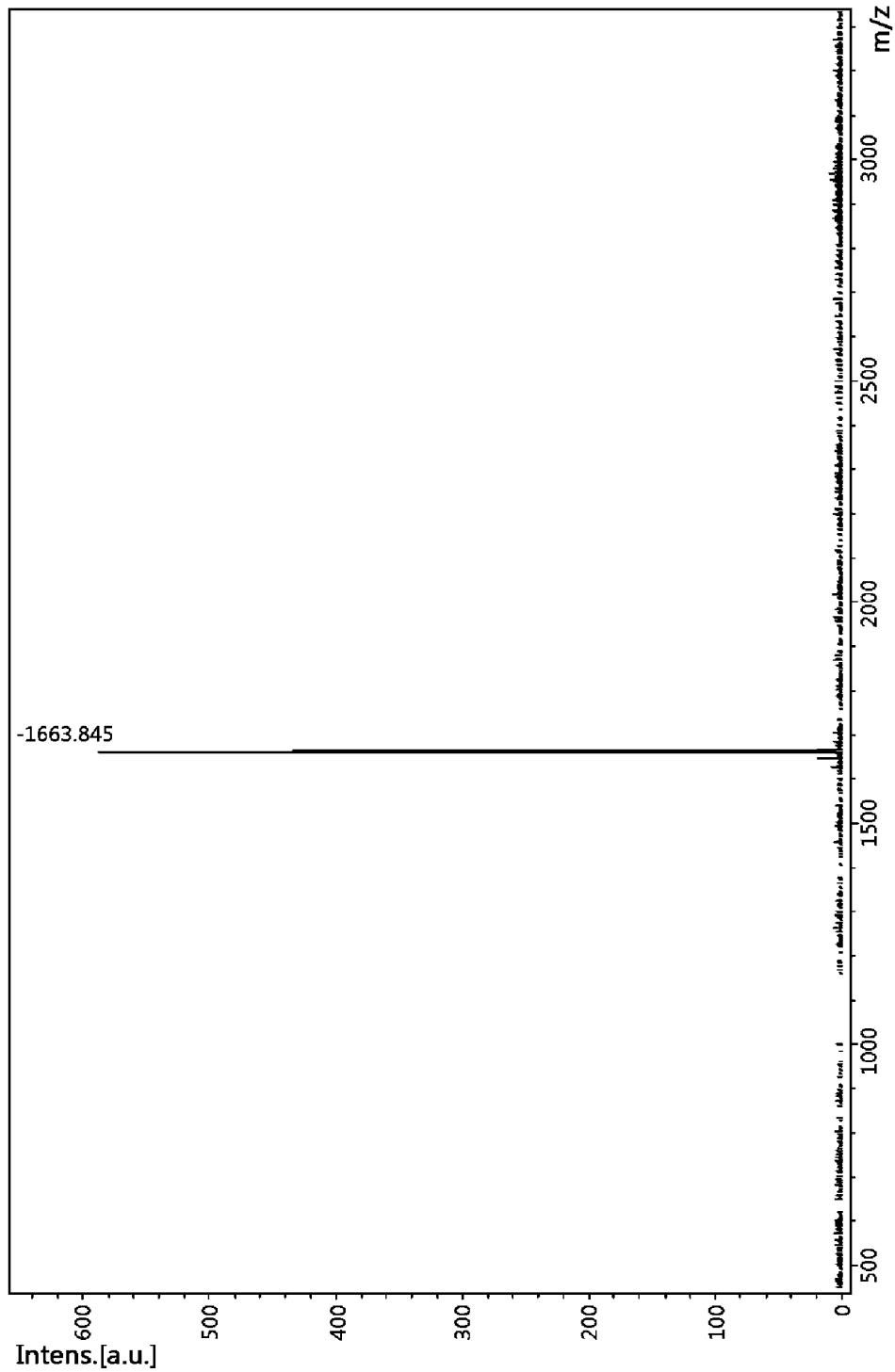
FIG. 2 shows the results of HU025 (SEQ ID NO:3) measured by the MALDI-TOF mass analysis method.
Figure 3:
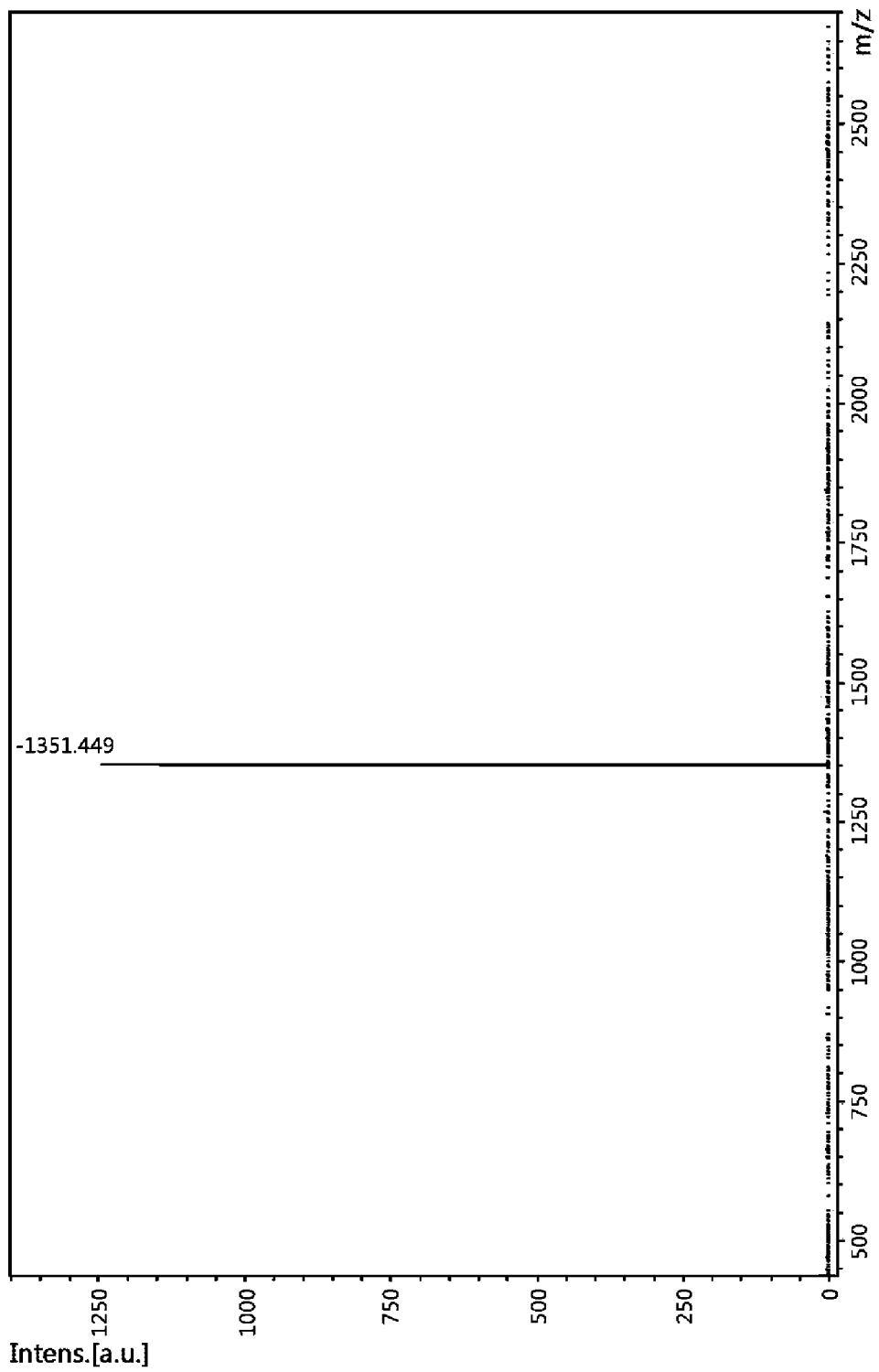
FIG. 3 shows the results of HU026 (SEQ ID NO:4) measured by the MALDI-TOF mass analysis method.
Figure 4:
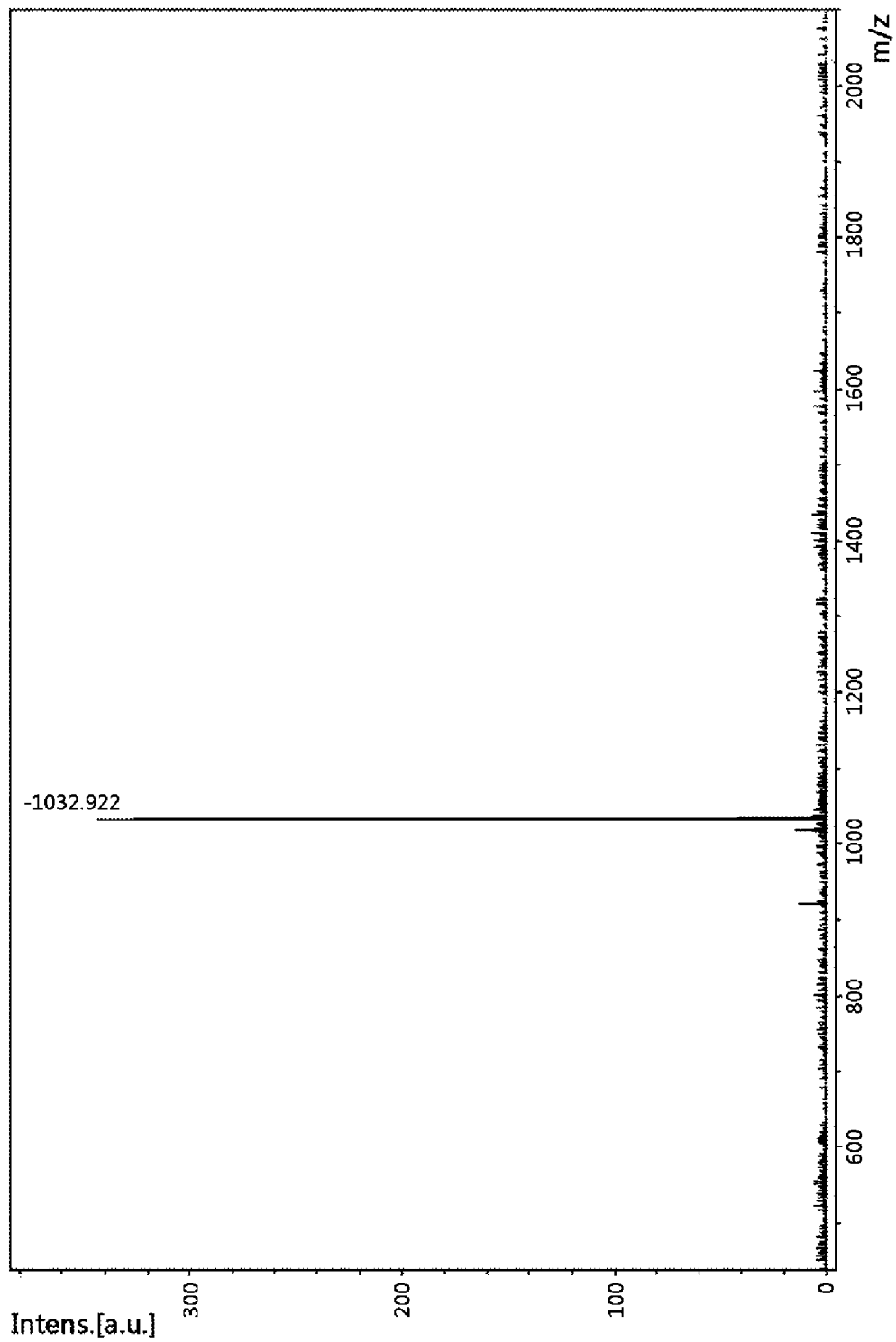
FIG. 4 shows the results of HU027 (SEQ ID NO:5) measured by the MALDI-TOF mass analysis method.
Figure 5:
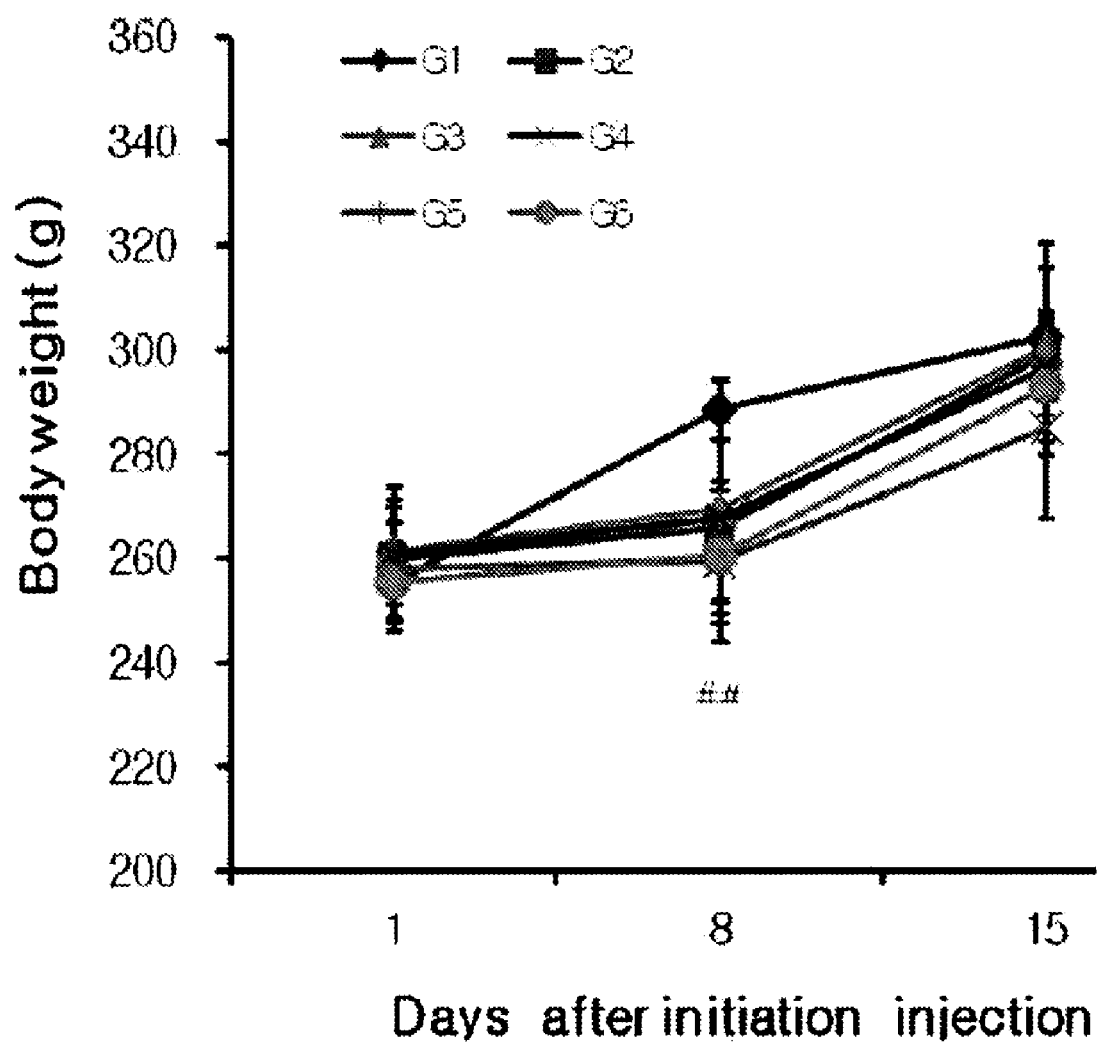
FIG. 5 shows the measurement results of weight changes of G1-G6.
(G1: Normal control, n=5
G2: Vehicle control, n=9-10
G3: Test article (3.3 µg/head/day) (SEQ ID NO:1), n=10
G4: Test article (10 µg/head/day) (SEQ ID NO:1), n=10
G5: Test article (30 µg/head/day) (SEQ ID NO:1), n=10
G6: Positive control (10 µg/head/day), n=9-10)

As a result, any abnormal syndrome was not observed after test substance was applied, and on the 8th day (Day 8), a statistically significant weight reduction ($P<0.01$) was observed in burn group when compared to normal group, but the weight reduction was the result of burn (Table 2, FIG. 5).

TABLE 2

| | BODY WEIGHTS (g) | | MALE |
|---|---|---|---|
| | Day 1 | Day 8 | Day 15 |
| G1 | 255.31 ± 8.84 | 288.69 ± 5.72 | 302.88 ± 4.53 |
| G2 | 260.02 ± 13.82 | 266.12 ± 16.86## | 299.07 ± 16.75 |
| G3 | 261.24 ± 10.05 | 269.41 ± 17.57 | 300.31 ± 20.36 |
| G4 | 260.59 ± 9.27 | 267.86 ± 5.20 | 296.55 ± 8.86 |
| G5 | 257.94 ± 9.23 | 259.49 ± 15.34 | 284.87 ± 17.06 |
| G6 | 255.56 ± 7.60 | 260.49 ± 12.77 | 293.06 ± 13.16 |

Figure 6:
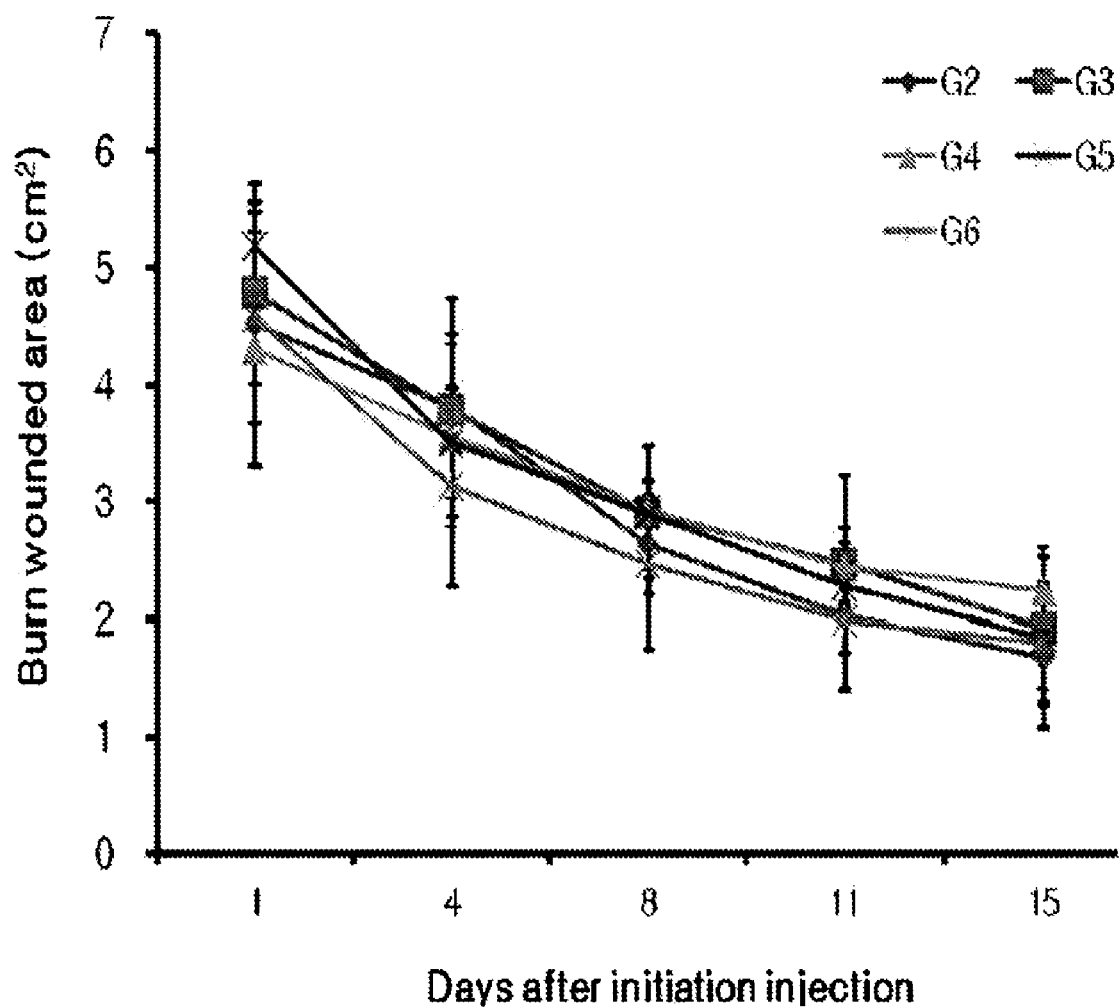
FIG. 6 shows the measurement results of burn wound area changes of G1-G6.
(G2: Vehicle control, n=9-10
G3: Test article (3.3 µg/head/day) (SEQ ID NO:1), n=10
G4: Test article (10 µg/head/day) (SEQ ID NO:1), n=10
G5: Test article (30 µg/head/day) (SEQ ID NO:1), n=10
G6: Positive control (10 µg/head/day), n=9-10)
Figure 7:
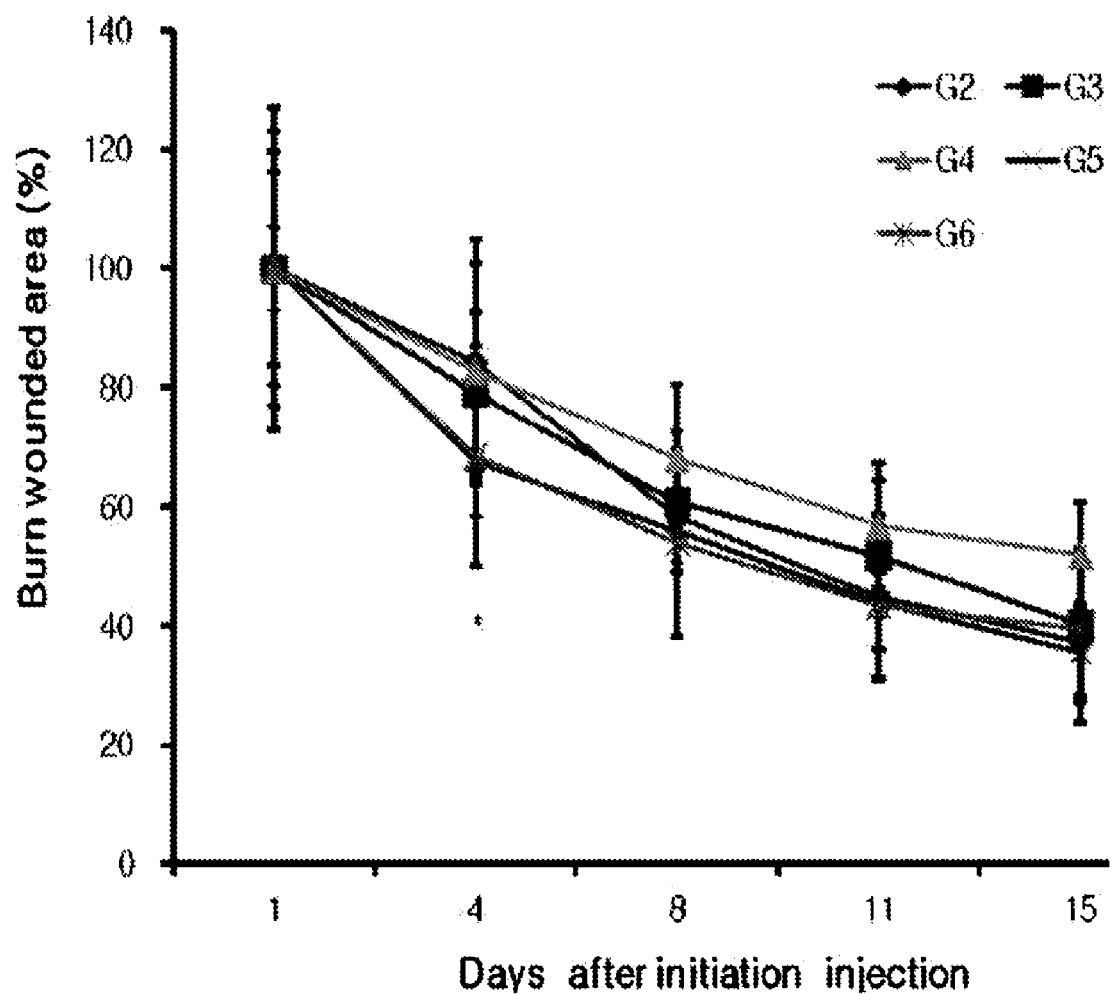
FIG. 7 shows burn wound area reduction (%) of G2-G6.
(G1: Normal control, n=5
G2: Vehicle control, n=9-10
G3: Test article (3.3 µg/head/day) (SEQ ID NO:1), n=10
G4: Test article (10 µg/head/day) (SEQ ID NO:1), n=10

Data are expressed as Mean ± S.D. The results were statistically analyzed student't-test.
significantly different from G1 versus G2, $P < 0.01$ As a result of measuring the burn wound area, in comparing absolute values of areas, a statistically significant change was not observed in all experimental groups as compared to negative control (Table 3, FIG. 6). As a result of measuring the reduction (%) in burn wound area, a statistically significant area reduction was observed in test substance 30 μg/head/day group (G5) on Day 4 when compared to negative control ($P<0.05$), and any difference was not observed in the remaining test substance-administered groups (Table 4, FIG. 7).

TABLE 3

| | BURN WOUNDED AREA ($cm^2$) | | | | MALE |
|---|---|---|---|---|---|
| | Day 1 | Day 4 | Day 8 | Day 11 | Day 15 |
| G1 | — | — | — | — | — |
| G2 | 4.5 ± 1.2 | 3.8 ± 0.9 | 2.6 ± 0.4 | 2.0 ± 0.6 | 1.7 ± 0.6 |
| G3 | 4.8 ± 0.8 | 3.8 ± 0.6 | 2.9 ± 0.6 | 2.5 ± 0.7 | 1.9 ± 0.6 |
| G4 | 4.3 ± 0.9 | 3.6 ± 0.8 | 2.9 ± 0.5 | 2.4 ± 0.3 | 2.2 ± 0.4 |
| G5 | 5.2 ± 0.4 | 3.5 ± 0.5 | 2.9 ± 0.3 | 2.3 ± 0.1 | 1.8 ± 0.4 |
| G6 | 4.6 ± 0.9 | 3.1 ± 0.8 | 2.5 ± 0.7 | 1.9 ± 0.6 | 1.8 ± 0.5 |

Data are expressed as Mean ± S.D. The results were statistically analyzed student't-test.

TABLE 4

| | BURN WOUNDED AREA (%) | | | | MALE |
|---|---|---|---|---|---|
| | Day 1 | Day 4 | Day 8 | Day 11 | Day 15 |
| G1 | — | — | — | — | — |
| G2 | 100.0 ± 26.9 | 84.3 ± 20.7 | 58.3 ± 9.2 | 44.8 ± 13.8 | 37.3 ± 13.5 |
| G3 | 100.0 ± 16.3 | 79.2 ± 13.571 | 60.8 ± 11.9 | 51.6 ± 15.7 | 40.1 ± 12.8 |
| G4 | 100.0 ± 23.0 | 82.7 ± 18.0 | 68.2 ± 12.3 | 56.8 ± 7.7 | 51.9 ± 8.9 |
| G5 | 100.0 ± 7.0 | 67.6 ± 9.3* | 55.9 ± 5.1 | 43.9 ± 2.6 | 35.6 ± 8.4 |
| G6 | 100.0 ± 19.7 | 68.5 ± 18.5 | 53.922 ± 15.7 | 43.5 ± 12.6 | 39.4 ± 11.3 |

Data are expressed as Mean ± S.D. The results were statistically analyzed student't-test
*significantly different from G2, $P < 0.05$ The histopathology test results are as follows (Table 5, FIG. 8, FIG. 9 and FIG. 10):

1) Eschar

In burn wound skin epidermis, fibrin, white blood cell, coagulated exudate and dead tissue are coagulated together to form eschar. The extent of eschar formation was assessed using 5 levels (0-4 points). Normal group G1 was normal skin tissue where eschar is not observed. In negative control (G2) and test substance 3.3 μg/head/day administered group (G3), eschar as thick as mean 4.0±0.0 and 4.0±0.0 points was observed over the entire burned area and assessed as being very severe. In test substance 10 μg/head/day administered group (G4), eschar scored 3.2±0.6 points corresponding to the level of about 80% of the entire burned area, and in test substance 30 μg/head/day administered group (G5) and positive control (G6), eschar scored 2.7±0.7 and 2.6±0.5 points, indicating reduced eschar formation. Furthermore, in test substance 10 μg/head/day administered group (G4), 30 μg/head/day administered group (G5) and positive control (G6), reduced eschar formation and reduced eschar thickness were observed, and the statistical analysis results revealed that there was significance compared to negative control (G2) ($P<0.01$).

2) Infiltration of Inflammatory Cells

After burn was induced, an acute inflammatory reaction happens, and lymphocyte and neutrocyte infiltration is primarily observed. The extent of inflammatory cell infiltration was assessed using 5 levels (0-4 points). The normal group (G1) was normal tissue where inflammatory cell infiltration was not observed. In negative control (G2), all test substance administered groups (G3, G4, G5) and positive control (G6), infiltration of inflammatory cells such as lymphocyte, neutrocyte, and monocyte was observed in epidermis, dermis, and hypodermis layer, and any difference between each group was not observed.

3) Skin Appendage Regeneration (Pilosebaceous)

The extent to which skin appendages located in the dermis layer, such as follicles, sweat glands, and glandulae sebaceae are regenerated after burn is an important standard for determining the extent of skin regeneration with epidermal regeneration. The skin appendages are composed of epidermal cells, and undifferentiated cells located in the appendages are differentiated and move to epidermis, and participate in the regeneration process of epidermis. The extent of regeneration of skin appendages was assessed using 5 levels (0-4 points). In normal group (G1), skin appendages such as follicles and glandulae sebaceae were observed as a normal structure and assessed as 4 points. In negative control (G2), regeneration of skin appendages was not observed at all, or the extent of regeneration was observed as being very low. In test substance 10 ug/head/day administered group (G4) and test substance 30 μg/head/day administered group (G5), test substance concentration-dependent regeneration of skin appendages was found as getting promoted, and the skin appendage regeneration level was found as being statistically significant compared to negative control (G2) ($P<0.05$ or $P<0.01$). In positive control (G6), regeneration promotion of skin appendages was also observed, and was statistically significant ($P<0.01$).

4) Connective Tissue Growth (Fibroplasia)

After burn was induced, fibroblast growth and an increase in collagen produced from its cell in the therapy process is observed. The extent of connective tissue growth was assessed using 5 levels (0-4 points). Following fiber cell growth and collagen production in dermis at high density together with skin regeneration, when regeneration is completed, grown fiber cell and increased collagen slowly reduces and reaches a normal level. The normal group (G1) was normal tissue where fibroblast was not observed. In negative control (G2), all test substance administered groups (G3, G4, G5) and positive control (G6), very active fiber cell growth and collagen increase in dermis and hypodermis was observed, and it was assessed that there was no difference between each group.

5) Epidermal Regeneration

The epidermal cell regeneration is the process of regeneration of the damaged or lost epidermis with basal cell growth and differentiation into skin epidermal cells. For the epidermal regeneration capacity, the extent of epidermis formation and basal cell growth was observed and assessed using 5 levels (0-4 points). In normal group (G1), normal epidermal tissue of the basal layer, spinous layer, granular layer, and cornified layer was observed. In negative control (G2), epidermal regeneration was not observed in most of the animals. In test substance 3.3 μg/head/day administered group (G3), a very low level of basal layer cell regeneration was observed in some regions, and in test substance 10 μg/head/day administered group (G4) and 30 μg/head/day administered group (G5) and positive control (G6), regeneration of a basal layer was observed over the wider area, and it was assessed as having a statistically significant promotion effect of the regeneration of epidermal cells compared to negative control ($P<0.05$).

TABLE 5

| Group | Eschar | Infiltration of Inflammatory cells | Pilosebaceous | Fibroplasia | Epidermal regeneration |
|---|---|---|---|---|---|
| G1 | 0 | 0 | 4.0 ± 0.0 | 0 | 4.0 ± 0.0 |
| G2 | 4.0 ± 0.0## | 2.9 ± 0.4## | 0 ± 0.0## | 3.0 ± 0.0## | 0.0 ± 0.0## |
| G3 | 4.0 ± 0.0 | 3.0 ± 0.0 | 0.1 ± 0.3 | 3.1 ± 0.3 | 0.1 ± 0.0 |
| G4 | 3.2 ± 0.6** | 3.0 ± 0.0 | 0.9 ± 1.1* | 3.0 ± 0.5 | 0.6 ± 0.5* |
| G5 | 2.7 ± 0.7** | 3.0 ± 0.0 | 1.1 ± 1.0** | 3.3 ± 0.5 | 0.6 ± 0.7* |
| G6 | 2.6 ± 0.5** | 2.7 ± 0.5 | 0.4 ± 0.5** | 3.2 ± 0.4 | 0.6 ± 0.5* |

Data are expressed as Mean ± S.D. The results were statistically analyzed by box-plot and Kruscal-wallis methods.
*significantly different from G1 value, $P < 0.05$
**significantly different from G2 value, $P < 0.01$
significantly different from G1 versus G2, $P < 0.01$ Example 3. Wrinkle Reduction Treatment Women aged 30-65 having wrinkles around eyes were tested. For 4 weeks, test product (HU022 (SEQ ID NO:1) or HU024 (SEQ ID NO:2)) and control product (D.i-water) were randomly given to use the products on each of left and right sides of the face twice daily, and at the first visit, the subjects received test product and control product to use for 4 weeks, and at the same time, assessment and investigation before use was completed. They had second and third visits at the interval of 2 weeks after the start of use, and at each visit, were required to respond to various types of assessment and investigation defined in the experiment.

The assessment items, test method and its results are as follows:

(1) Assessment of Wrinkle Reduction Effect of Test Product HU022 (SEQ ID NO:1)

The extent of wrinkles around eyes was measured using equipment. A target site to measure the wrinkle extent was regions around the eyes of the subjects, and the left side and the right side of the face were set as a measurement site. To measure the wrinkle extent, the subjects were allowed to wash the measurement site with water, and take a rest for 30 minutes in the waiting room under constant temperature and constant humidity conditions of indoor temperature 20-25° C. and humidity 40-60% to acclimate the skin surface temperature and humidity to the environment of the measurement space, and were not permitted to drink water during the rest. For objective measurement, measurements were performed by one researcher, and the same site was measured at each time of the first visit before use and the second and third visits in 2 and 4 weeks after use. Transparency profilometry analysis was performed using Visiometer SV600 (Courage-Khazaka electronic GmbH, Germany) on skin replica of the site to which test product and control product were applied before use and 2 and 4 weeks after use, and to identify if there is any difference in each of control group and experimental group after use, a change (%) in R1, R2, R4, R5 measurement values in 2 and 4 weeks after use relative to before use was analyzed.

The wrinkle extent parameters are as follows:

TABLE 6

R1 Skin roughness
 The difference between highest peak and lowest valley of wrinkle profile
R2 Maximum roughness
 The largest of five R1 values obtained for each of five equal subdivisions in wrinkle profile
R3 Average roughness
 Arithmetic average of a difference between maximum and minimum measured in each subdivision after the wrinkle profile is divided into five equal subdivisions along X-axis
 Free of artifacts as opposed to R1 and R2
R4 Smoothness depth
 The integral of the area between highest peak of wrinkle profile and the profile, divided by the length of mean line of the profile
 Average depth of skin wrinkle
R5 Arithmetic average roughness
 The integral of the area between mean line of profile and the profile, divided by the length of mean line of the profile
 Average roughness of skin To identify changes in R3 numerical value after the use of test product (HU022 (SEQ ID NO:1)), R3 numerical values were measured before use, 2 weeks after use, and 4 weeks after use. The R3 numerical value of test product was 34.24±3.51 before use, 24.41±4.16 in 2 weeks after use, and 18.62±2.79 in 4 weeks after use, and the R3 numerical value of control product was 22.48±2.74 before use, 20.70±1.76 in 2 weeks after use, and 18.13±0.91 in 4 weeks after use, and to clearly identify changes in R3 numerical value, a change (%) in R3 was calculated each time zone (Table 7, FIG. 13).

TABLE 7

| | Visit | Test product | (Mean ± SD) Control product |
|---|---|---|---|
| | Before use | 34.24 ± 3.51 | 22.48 ± 2.74 |
| | 2 weeks after use | 24.41 ± 4.16 | 20.70 ± 1.76 |
| | 4 weeks after use | 18.62 ± 2.79 | 18.13 ± 0.91 |
| Change(%) | Before use-2 weeks after use | −23.71 | −7.91 |
| | Before use-4 weeks after use | −45.62 | −19.33 |

*Change(%) = {(After − Before)/Before}*100

To identify changes in R1 numerical value after the use of test product (HU022 (SEQ ID NO:1)), R1 numerical values were measured before use, 2 weeks after use, and 4 weeks after use. The R1 numerical value of test product was 76.23±12.15 before use, 54.59±10.99 in 2 weeks after use, and 51.06±19.28 in 4 weeks after use, and the R1 numerical value of control product was 55.74±12.48 before use, 56.17±11.11 in 2 weeks after use, and 50.86±4.67 in 4 weeks after use (Table 8, FIG. 11).

TABLE 8

| | Visit | Test product | (Mean ± SD) Control product |
|---|---|---|---|
| | Before use | 76.23 ± 12.15 | 55.74 ± 12.48 |
| | 2 weeks after use | 54.59 ± 10.99 | 56.17 ± 11.11 |
| | 4 weeks after use | 51.06 ± 19.28 | 50.86 ± 4.67 |
| Change(%) | Before use-2 weeks after use | −28.38 | 0.77 |
| | Before use-4 weeks after use | −33.02 | −8.76 |

*Change(%) = {(After − Before)/Before}*100

To identify changes in R2 numerical value after use of test product (HU022 (SEQ ID NO:1)), R2 numerical values were measured before use, 2 weeks after use, and 4 weeks after use. The R2 numerical value of test product was 54.26±5.70 before use, 36.87±6.02 in 2 weeks after use, and 29.16±2.74 in 4 weeks after use, and the R2 numerical value of control product was 35.24±5.12 before use, 31.64±4.37 in 2 weeks after use, and 27.57±2.89 in 4 weeks after use (Table 9, FIG. 12).

TABLE 9

| | Visit | Test product | (Mean ± SD) Control product |
|---|---|---|---|
| | Before use | 54.26 ± 5.70 | 35.24 ± 5.12 |
| | 2 weeks after use | 36.87 ± 6.02 | 31.64 ± 4.37 |
| | 4 weeks after use | 29.16 ± 5.12 | 27.57 ± 2.89 |
| Change(%) | Before use-2 weeks after use | −32.04 | −10.23 |
| | Before use-4 weeks after use | −46.25 | −21.75 |

*Change(%) = {(After − Before)/Before}*100

To identify changes in R4 numerical value after use of test product (HU022 (SEQ ID NO:1)), R4 numerical values were measured before use, 2 weeks after use, and 4 weeks after use. The R4 numerical value of test product was 30.41±7.01 before use, 23.64±5.11 in 2 weeks after use, and 22.94±10.03 in 4 weeks after use, and the R4 numerical value of control product was 24.50±5.43 before use, 25.06±5.49 in 2 weeks after use, and 24.42±4.57 in 4 weeks after use (Table 10, FIG. 14).

TABLE 10

|  | Visit | Test product | (Mean ± SD) Control product |
|---|---|---|---|
|  | Before use | 30.41 ± 7.01 | 24.50 ± 5.43 |
|  | 2 weeks after use | 23.64 ± 5.11 | 25.06 ± 5.49 |
|  | 4 weeks after use | 22.94 ± 10.03 | 24.42 ± 4.57 |
| Change(%) | Before use-2 weeks after use | −22.27 | 2.31 |
|  | Before use-4 weeks after use | −24.57 | −0.33 |

*Change(%) = {(After − Before)/Before}*100

To identify changes in R5 numerical value after use of test product (HU022 (SEQ ID NO:1)), R5 numerical values were measured before use, 2 weeks after use, and 4 weeks after use. The R5 numerical value of test product was 13.57±3.65 before use, 9.44±2.44 in 2 weeks after use, and 10.10±5.97 in 4 weeks after use, and the R5 numerical value of control product was 11.02±2.94 before use, 11.44±3.14 in 2 weeks after use, and 10.51±1.90 in 4 weeks after use (Table 11, FIG. 15).

TABLE 11

|  | Visit | Test product | (Mean ± SD) Control product |
|---|---|---|---|
|  | Before use | 13.57 ± 3.65 | 11.02 ± 2.94 |
|  | 2 weeks after use | 9.44 ± 2.44 | 11.44 ± 3.14 |
|  | 4 weeks after use | 10.10 ± 5.97 | 10.51 ± 1.90 |
| Change(%) | Before use-2 weeks after use | −30.43 | 3.79 |
|  | Before use-4 weeks after use | −26.52 | −4.64 |

*Change(%) = {(After − Before)/Before}*100

Furthermore, the wrinkle extent was measured by 3D imaging. A target site to measure the wrinkle extent was regions around the eyes of the subjects, and the right side of the face was set as a measurement site. To measure the wrinkle extent, the subjects were allowed to wash the measurement site with water, and take a rest for 30 minutes in the waiting room under constant temperature constant humidity conditions of indoor temperature 20-25° C. and humidity 40-60% to acclimate the skin surface temperature and humidity to the environment of the measurement space, and were not permitted to drink water during the rest. For objective measurement, measurements were performed by one researcher, and the same site was measured at each time of the first visit before use and the second and third visits in 2 and 4 weeks after use. Before use and in 2 and 4 weeks after use, images of the site to which the test product (HU022 (SEQ ID NO:1)) was applied were formed using 3D skin imaging machine (PRIMOS Premium), and to verify if there is any difference in each of control group and experimental group in 4 weeks after use, wrinkle parameters, Ra, Rmax, Rt, Rp, Rv values, in the stored images of 2 weeks and 4 weeks after use relative to before use were analyzed.

The wrinkle extent parameters are as follows:

TABLE 12

| | |
|---|---|
| Ra | Roughness average of wrinkle profile |
| Rmax | Maximum height of wrinkle profile |
| Rt | Distance between highest peak and lowest valley of wrinkle profile |
| Rp | Maximum profile peak height of wrinkle profile |
| Rv | Maximum profile valley depth of wrinkle profile |

To identify changes in Ra numerical value after use of test product, Ra numerical values were measured before use, 2 weeks after use, and 4 weeks after use. The Ra numerical value of test product was 19.19±4.27 before use, 18.20±3.94 in 2 weeks after use, and 17.00±3.88 in 4 weeks after use, and the Ra numerical value of control product was 14.86±4.48 before use, 14.94±4.73 in 2 weeks after use, and 14.60±4.58 in 4 weeks after use (Table 13, FIG. 16).

TABLE 13

|  | Visit | Test product | (Mean ± SD) Control product |
|---|---|---|---|
|  | Before use | 19.19 ± 4.27 | 14.86 ± 4.48 |
|  | 2 weeks after use | 18.20 ± 3.94 | 14.94 ± 4.73 |
|  | 4 weeks after use | 17.00 ± 3.88 | 14.60 ± 4.58 |
| Change(%) | Before use-2 weeks after use | −5.15 | 0.54 |
|  | Before use-4 weeks after use | −11.42 | −1.76 |

*Change(%) = {(After − Before)/Before}*100

To identify changes in Rmax numerical value after use of test product, Rmax numerical values were measured before use, 2 weeks after use, and 4 weeks after use. The Rmax numerical value of test product was 176.29±27.79 before use, 168.83±29.61 in 2 weeks after use, and 168.80±33.21 in 4 weeks after use, and the Rmax numerical value of control product was 162.81±64.15 before use, 159.52±61.85 in 2 weeks after use, and 158.36±62.80 in 4 weeks after use (Table 14, FIG. 17).

TABLE 14

|  | Visit | Test product | (Mean ± SD) Control product |
|---|---|---|---|
|  | Before use | 176.29 ± 27.79 | 162.81 ± 64.15 |
|  | 2 weeks after use | 168.83 ± 29.61 | 159.52 ± 61.85 |
|  | 4 weeks after use | 168.80 ± 33.21 | 158.36 ± 62.80 |
| Change(%) | Before use-2 weeks after use | −4.23 | −2.02 |
|  | Before use-4 weeks after use | −4.25 | −2.73 |

*Change(%) = {(After − Before)/Before}*100

To identify changes in Rt numerical value after use of test product, Rt numerical values were measured before use, 2 weeks after use, and 4 weeks after use. The Rt numerical value of test product was 195.05±31.31 before use, 187.85±34.10 in 2 weeks after use, and 184.63±36.83 in 4 weeks after use, and the Rt numerical value of control product is 174.12±68.96 before use, 171.13±66.76 in 2 weeks after use, and 169.86±65.80 in 4 weeks after use (Table 15, FIG. 18).

TABLE 15

|  | Visit | Test product | (Mean ± SD) Control product |
|---|---|---|---|
|  | Before use | 195.05 ± 31.31 | 174.12 ± 68.96 |
|  | 2 weeks after use | 187.85 ± 34.10 | 171.13 ± 66.76 |
|  | 4 weeks after use | 184.63 ± 36.83 | 169.86 ± 65.80 |
| Change(%) | Before use-2 weeks after use | −3.69 | −1.72 |
|  | Before use-4 weeks after use | −5.35 | −2.45 |

*Change(%) = {(After − Before)/Before}*100

To identify changes in Rp numerical value after use of test product, Rp numerical values were measured before use, 2 weeks after use, and 4 weeks after use. The Rp numerical value of test product was 122.73±31.55 before use, 116.47±35.75 in 2 weeks after use, and 121.88±38.06 in 4 weeks after use, and the Rp numerical value of control product was 123.29±57.51 before use, 120.32±53.57 in 2 weeks after use, and 119.57±56.77 in 4 weeks after use (Table 16, FIG. 19).

TABLE 16

|  | Visit | Test product | (Mean ± SD) Control product |
|---|---|---|---|
|  | Before use | 122.73 ± 31.55 | 123.29 ± 57.51 |
|  | 2 weeks after use | 116.47 ± 35.75 | 120.32 ± 53.57 |
|  | 4 weeks after use | 121.88 ± 38.06 | 119.57 ± 56.77 |
| Change(%) | Before use-2 weeks after use | −5.10 | −2.41 |
|  | Before use-4 weeks after use | −0.70 | −3.02 |

*Change(%) = {(After − Before)/Before}*100

To identify changes in Rv numerical value after use of test product, Rv numerical values were measured before use, 2 weeks after use, and 4 weeks after use. The Rv numerical value of test product was 72.32±17.16 before use, 71.38±16.44 in 2 weeks after use, and 62.75±11.92 in 4 weeks after use, and the Rv numerical value of control product was 50.83±16.13 before use, 50.81±16.29 in 2 weeks after use, and 50.29±11.75 in 4 weeks after use (Table 17, FIG. 20).

TABLE 17

|  | Visit | Test product | (Mean ± SD) Control product |
|---|---|---|---|
|  | Before use | 72.32 ± 17.16 | 50.83 ± 16.13 |
|  | 2 weeks after use | 71.38 ± 16.44 | 50.81 ± 16.29 |
|  | 4 weeks after use | 62.75 ± 11.92 | 50.29 ± 11.75 |
| Change(%) | Before use-2 weeks after use | −1.30 | −0.05 |
|  | Before use-4 weeks after use | −13.24 | −1.07 |

*Change(%) = {(After − Before)/Before}*100

Furthermore, visual assessment was performed. At each visit before and after use, experts assessed the wrinkle extent by scoring using global photodamage score (Br J Dermatol. 2010; 162(3):497-502). To verify if there is any difference in each of control group and experimental group in 4 weeks after use, a change (%) in visual assessment scores of 2 weeks and 4 weeks after use relative to before use was analyzed. The visual assessment scores are as follows (Table 18):

TABLE 18

| Severity | Wrinkle grading |
|---|---|
| 0 | none |
| 1 | none/mild |
| 2 | mild |
| 3 | mild/moderate |
| 4 | moderate |
| 5 | moderate/severe |
| 6 | severe |
| 7 | very severe |

As a result, the expert visual assessment score of test product was 2.17±0.75 before use, 2.17±0.75 in 2 weeks after use, and 1.67±1.03 in 4 weeks after use, and the expert visual assessment score of control product was 2.33±1.03 before use, 2.33±1.03 in 2 weeks after use, and 2.33±1.03 in 4 weeks after use (Table 19, FIG. 21).

TABLE 19

|  | Visit | Test product | (Mean ± SD) Control product |
|---|---|---|---|
|  | Before use | 2.17 ± 0.75 | 2.33 ± 1.03 |
|  | 2 weeks after use | 2.17 ± 0.75 | 2.33 ± 1.03 |
|  | 4 weeks after use | 1.67 ± 1.03 | 2.33 ± 1.03 |
| Change(%) | Before use-2 weeks after use | 0 | 0 |
|  | Before use-4 weeks after use | −23.08 | 0 |

*Change(%) = {(After − Before)/Before}*100

Furthermore, surveying the subjects about effectiveness was conducted. The subjects were asked to personally make responses about the extent to which the subjects felt that wrinkles reduced after use of test product using 5 levels: better (4), a little bit better (3), no change (2), a little bit worse (1), worse (0). The researcher determined if test product has efficacy by calculating the percentage of the number of subjects for each response.

As a result of survey assessment about wrinkle reduction, at the third visit in 4 weeks after use, the subjects responded whether both test product and control product reduced wrinkles, and particularly, test product was better at reducing wrinkles than control product. As can be seen from this, the subjects having participated in the test found that the wrinkle reduction efficacy of test product was superior (Table 20).

TABLE 20

|  | Number of subjects (percentage, %) | | | | | | Standard |
|---|---|---|---|---|---|---|---|
|  | 4* | 3* | 2* | 1* | 0* | Mean | deviation |
| Test product | 0 | 5 (83.3) | 1 (16.7) | 0 | 0 | 2.83 | 0.41 |
| Control product | 3 (50.0) | 2 (33.3) | 1 (16.7) | 0 | 0 | 3.33 | 0.82 |

*4: very good, 3: good, 2: fair 1: bad, 0: very bad

Furthermore, survey assessment about tactile sensation and preference was performed, and the subjects were asked to respond personally to survey materials about tactile sensation the subjects felt in 4 weeks after use of clinical test product. Investigation was carried out based on the assessment items including the degree of moisture sensation, soft sensation, absorption performance, general tactile sensation, and fragrance, and assessment was carried out on 5 levels of very good, good, fair, bad, and very bad.

As a result of the investigation, it was found that the subjects generally had positive preference for test product. Particularly, the subjects had higher preference for test product than control product in terms of sticky sensation (Table 21).

TABLE 21

| | Preference score (mean ± standard deviation) | | | | | |
|---|---|---|---|---|---|---|
| | Moisture sensation | Soft sensation | Spreading performance | Absorption performance | Sticky sensation | Fragrance |
| Test product | 3.17 ± 0.75 | 3.17 ± 0.75 | 3.33 ± 0.52 | 3.17 ± 0.75 | 3.00 ± 0.63 | 2.50 ± 0.55 |
| Control product | 3.33 ± 0.82 | 3.33 ± 0.82 | 3.00 ± 0.63 | 2.50 ± 0.75 | 2.83 ± 0.76 | 2.50 ± 0.55 |

*4: very good, 3: good, 2: fair 1: bad, 0: very bad

Furthermore, compliance assessment was performed, and at the second and third visits, records of product for test were collected, the number of uses of test product was identified, and the compliance was calculated. At each visit, any subject having the compliance of less than 80% or not having used 6 consecutive times or more was ruled out of the test. As a result, at the end of the test, the total compliance was 100%, the highest compliance was 100.00%, and the lowest compliance was 100.00%. In this test, there was no subject having the compliance of 80% or less, and data of all the subjects was used to analyze the results.

Furthermore, safety assessment was performed, and for safety of clinical test product, in all subjects having used the test product at least once, abnormal responses found at the second week and fourth week after use and abnormal responses reported during the test period were all used as safety assessment data of the product. There was no report about abnormal response, and on the dermatologist's physical examination, any skin abnormal sign, for example, redness, rash, and itching sensation was not observed. Accordingly, it could be seen that test product was a safe product not causing irritation to the skin.

(2) Assessment of Wrinkle Reduction Effect of Test Product HU024 (SEQ ID NO:2)

The assessment items and test method were the same as those used for assessment of test product HU022 (SEQ ID NO:1).

After the extent of wrinkle was measured using equipment, to identify changes in R3 numerical value after use of test product, R3 numerical values were measured before use, 2 weeks after use, and 4 weeks after use. The R3 numerical value of test product was 29.15±5.56 before use, 20.80±3.97 in 2 weeks after use, and 17.81±4.00 in 4 weeks after use, and the R3 numerical value of control product was 24.43±3.12 before use, 23.56±3.53 in 2 weeks after use, and 18.57±1.86 in 4 weeks after use (Table 22, FIG. 24).

TABLE 22

| | Visit | Test product | (Mean ± SD) Control product |
|---|---|---|---|
| | Before use | 29.15 ± 5.56 | 24.43 ± 3.12 |
| | 2 weeks after use | 20.80 ± 3.97 | 23.56 ± 3.53 |
| | 4 weeks after use | 17.81 ± 4.00 | 18.57 ± 1.86 |
| Change(%) | Before use-2 weeks after use | −28.66 | −3.55 |
| | Before use-4 weeks after use | −54.55 | −23.99 |

*Change(%) = {(After − Before)/Before}*100

The R1 numerical value of test product was 71.33±15.8 before use, 57.29±3.21 in 2 weeks after use, and 45.23±13.77 in 4 weeks after use, and the R1 numerical value of control product was 58.01±21.09 before use, 56.17±15.89 in 2 weeks after use, and 45.03±14.74 in 4 weeks after use (Table 23, FIG. 22).

TABLE 23

| | Visit | Test product | (Mean ± SD) Control product |
|---|---|---|---|
| | Before use | 71.33 ± 15.86 | 58.01 ± 21.09 |
| | 2 weeks after use | 57.29 ± 3.21 | 56.17 ± 15.89 |
| | 4 weeks after use | 45.23 ± 13.77 | 45.03 ± 14.74 |
| Change(%) | Before use-2 weeks after use | −19.68 | −3.17 |
| | Before use-4 weeks after use | −36.59 | −22.37 |

*Change(%) = {(After − Before)/Before}*100

The R2 numerical value of test product was 46.06±11.62 before use, 30.71±6.57 in 2 weeks after use, and 28.67±7.47 in 4 weeks after use, and the R2 numerical value of control product was 35.97±5.82 before use, 37.15±4.96 in 2 weeks after use, and 26.68±3.30 in 4 weeks after use (Table 24, FIG. 23).

TABLE 24

| | Visit | Test product | (Mean ± SD) Control product |
|---|---|---|---|
| | Before use | 46.06 ± 11.62 | 35.97 ± 5.82 |
| | 2 weeks after use | 30.71 ± 6.57 | 37.15 ± 4.96 |
| | 4 weeks after use | 28.67 ± 7.47 | 26.68 ± 3.30 |
| Change(%) | Before use-2 weeks after use | −33.33 | 3.27 |
| | Before use-4 weeks after use | −37.74 | −25.84 |

*Change(%) = {(After − Before)/Before}*100

The R4 numerical value test product was 31.44±11.04 before use, 26.24±2.90 in 2 weeks after use, and 20.64±6.07 in 4 weeks after use, and the R4 numerical value of control product was 26.22±11.38 before use, 24.11±8.82 in 2 weeks after use, and 20.67±8.43 in 4 weeks after use (Table 25, FIG. 25).

TABLE 25

| | Visit | Test product | (Mean ± SD) Control product |
|---|---|---|---|
| | Before use | 31.44 ± 11.04 | 26.22 ± 11.38 |
| | 2 weeks after use | 26.24 ± 2.90 | 24.11 ± 8.82 |
| | 4 weeks after use | 20.64 ± 6.07 | 20.67 ± 8.43 |
| Change(%) | Before use-2 weeks after use | −16.54 | −8.04 |
| | Before use-4 weeks after use | −34.36 | −21.17 |

*Change(%) = {(After − Before)/Before}*100

The R5 numerical value of test product was 13.52±5.43 before use, 11.58±0.89 in 2 weeks after use, and 8.42±3.48 in 4 weeks after use, and the R5 numerical value of control product was 10.93±6.72 before use, 10.68±5.56 in 2 weeks after use, and 8.79±4.95 in 4 weeks after use (Table 26, FIG. 26).

TABLE 26

|  | Visit | Test product | (Mean ± SD) Control product |
|---|---|---|---|
|  | Before use | 13.52 ± 5.43 | 10.93 ± 6.72 |
|  | 2 weeks after use | 11.58 ± 0.89 | 10.68 ± 5.56 |
|  | 4 weeks after use | 8.42 ± 3.48 | 8.79 ± 4.95 |
| Change(%) | Before use-2 weeks after use | −14.36 | −2.26 |
|  | Before use-4 weeks after use | −37.71 | −19.59 |

*Change(%) = {(After − Before)/Before}*100

After the wrinkle extent was measured by 3D imaging, to identify changes in Ra numerical value after use of test product, Ra numerical values were measured before use, 2 weeks after use, and 4 weeks after use.

The Ra numerical value of test product was 18.64±3.19 before use, 18.33±2.12 in 2 weeks after use, and 17.71±2.43 in 4 weeks after use, and the Ra numerical value of control product was 15.49±2.77 before use, 15.23±2.51 in 2 weeks after use, and 15.53±2.46 in 4 weeks after use (Table 27, FIG. 27).

TABLE 27

|  | Visit | Test product | (Mean ± SD) Control product |
|---|---|---|---|
|  | Before use | 18.64 ± 3.19 | 15.49 ± 2.77 |
|  | 2 weeks after use | 18.33 ± 2.12 | 15.23 ± 2.51 |
|  | 4 weeks after use | 17.71 ± 2.43 | 15.53 ± 2.46 |
| Change(%) | Before use-2 weeks after use | −0.75 | 1.27 |
|  | Before use-4 weeks after use | −4.10 | 0.75 |

*Change(%) = {(After − Before)/Before}*100

The Rmax numerical value of test product was 206.55±40.54 before use, 198.77±39.74 in 2 weeks after use, and 196.85±39.02 in 4 weeks after use, and the Rmax numerical value of control product was 162.86±35.17 before use, 158.09±40.68 in 2 weeks after use, and 165.26±39.77 in 4 weeks after use (Table 28, FIG. 28).

TABLE 28

|  | Visit | Test product | (Mean ± SD) Control product |
|---|---|---|---|
|  | Before use | 206.55 ± 40.54 | 162.86 ± 35.17 |
|  | 2 weeks after use | 198.77 ± 39.74 | 158.09 ± 40.68 |
|  | 4 weeks after use | 196.85 ± 39.02 | 165.26 ± 39.77 |
| Change(%) | Before use-2 weeks after use | −3.77 | −2.93 |
|  | Before use-4 weeks after use | −4.69 | 1.47 |

*Change(%) = {(After − Before)/Before}*100

The Rt numerical value of test product was 225.94±45.00 before use, 216.37±41.76 in 2 weeks after use, and 210.60±38.61 in 4 weeks after use, and the Rt numerical value of control product was 174.55±34.66 before use, 167.65±41.28 in 2 weeks after use, and 176.14±39.43 in 4 weeks after use (Table 29, FIG. 29).

TABLE 29

|  | Visit | Test product | (Mean ± SD) Control product |
|---|---|---|---|
|  | Before use | 225.94 ± 45.00 | 174.55 ± 34.66 |
|  | 2 weeks after use | 216.37 ± 41.76 | 167.65 ± 41.28 |
|  | 4 weeks after use | 210.60 ± 38.61 | 176.14 ± 39.43 |
| Change(%) | Before use-2 weeks after use | −4.24 | −3.95 |
|  | Before use-4 weeks after use | −6.79 | 0.91 |

*Change(%) = {(After − Before)/Before}*100

The Rp numerical value of test product was 160.85±37.51 before use, 155.24±43.18 in 2 weeks after use, and 153.78±36.12 in 4 weeks after use, and the Rp numerical value of control product was 118.80±39.02 before use, 112.77±44.16 in 2 weeks after use, and 123.39±42.81 in 4 weeks after use (Table 30, FIG. 30).

TABLE 30

|  | Visit | Test product | (Mean ± SD) Control product |
|---|---|---|---|
|  | Before use | 160.85 ± 37.51 | 118.80 ± 39.02 |
|  | 2 weeks after use | 155.24 ± 43.18 | 112.77 ± 44.16 |
|  | 4 weeks after use | 153.78 ± 36.12 | 123.39 ± 42.81 |
| Change(%) | Before use-2 weeks after use | −3.48 | −5.07 |
|  | Before use-4 weeks after use | −4.40 | 3.86 |

*Change(%) = {(After − Before)/Before}*100

The Rv numerical value of test product was 65.09±11.95 before use, 61.12±8.02 in 2 weeks after use, and 56.82±12.01 in 4 weeks after use, and the Rv numerical value of control product was 55.75±17.98 before use, 54.87±21.72 in 2 weeks after use, and 52.75±15.00 in 4 weeks after use (Table 31, FIG. 31).

TABLE 31

|  | Visit | Test product | (Mean ± SD) Control product |
|---|---|---|---|
|  | Before use | 65.09 ± 11.95 | 55.75 ± 17.98 |
|  | 2 weeks after use | 61.12 ± 8.02 | 54.87 ± 21.72 |
|  | 4 weeks after use | 56.82 ± 12.01 | 52.75 ± 15.00 |
| Change(%) | Before use-2 weeks after use | −6.10 | −1.57 |
|  | Before use-4 weeks after use | −12.71 | −5.37 |

*Change(%) = {(After − Before)/Before}*100

To identify changes in visual assessment score, expert visual assessment scores were assessed before use, 2 weeks after use, and 4 weeks after use.

The expert visual assessment score of test product was 2.00±0.63 before use, 2.00±0.63 in 2 weeks after use, and 1.67±0.82 in 4 weeks after use, and the expert visual assessment score of control product was 2.00±0.63 before use, 2.00±0.63 in 2 weeks after use, and 2.00±0.63 in 4 weeks after use (Table 32, FIG. 32).

TABLE 32

|  | Visit | Test product | (Mean ± SD) Control product |
|---|---|---|---|
|  | Before use | 2.00 ± 0.63 | 2.00 ± 0.63 |
|  | 2 weeks after use | 2.00 ± 0.63 | 2.00 ± 0.63 |
|  | 4 weeks after use | 1.67 ± 0.82 | 2.00 ± 0.63 |

TABLE 32-continued

|  | Visit | Test product | (Mean ± SD) Control product |
|---|---|---|---|
| Change(%) | Before use-2 weeks after use | 0 | 0 |
|  | Before use-4 weeks after use | −16.67 | 0 |

*Change(%) = {(After − Before)/Before}*100

As a result of survey assessment about wrinkle reduction, at the third visit in 4 weeks after use, the subjects responded that both test product and control product reduced wrinkles, and particularly, test product was better at reducing wrinkles than control product. As can be seen from this, the subjects having participated in the test found that the wrinkle reduction efficacy of test product was superior.

TABLE 33

|  | Number of subjects (percentage, %) |  |  |  |  | Mean | Standard deviation |
|---|---|---|---|---|---|---|---|
|  | 4* | 3* | 2* | 1* | 0* |  |  |
| Test product | 1 (16.7) | 4 (66.7) | 1 (16.7) | 0 | 0 | 3.00 | 0.63 |
| Control product | 1 (16.7) | 3 (50.0) | 2 (33.3) | 0 | 0 | 2.83 | 0.75 |

*4: very good, 3: good, 2: fair 1: bad, 0: very bad

As a result of investigating the subjects' preference in terms of moisture sensation, soft sensation, spreading performance, absorption performance, sticky sensation and fragrance of test product, it was found that the subjects generally had positive preference for test product. Particularly, the preference for test product was higher than control product in terms of sticky sensation.

TABLE 34

| | Preference score (mean ± standard deviation) | | | | | |
|---|---|---|---|---|---|---|
|  | Moisture sensation | Soft sensation | Spreading performance | Absorption performance | Sticky sensation | Fragrance |
| Test product | 3.17 ± 0.75 | 3.17 ± 0.75 | 3.33 ± 0.52 | 3.17 ± 0.75 | 3.00 ± 0.63 | 2.50 ± 0.55 |
| Control product | 3.17 ± 0.75 | 3.17 ± 0.75 | 3.33 ± 0.82 | 3.17 ± 0.75 | 2.83 ± 0.75 | 2.50 ± 0.55 |

*4: very good, 3: good, 2: fair 1: bad, 0: very bad

Furthermore, there was no report about abnormal response while the subjects were using the test product for 4 weeks, and on the dermatologist's physical examination, any skin abnormal sign, for example, redness, rash and itching sensation was not observed. Accordingly, it could be seen that test product was a safe product not causing irritation to the skin.

Example 4. Hair Growth Test Effect

This test was conducted to assess the influence on hair growth of C57BL/6 mouse when 4 types of test substances, HU024 (SEQ ID NO:2), HU025 (SEQ ID NO:3), HU026 (SEQ ID NO:4), and HU027 (SEQ ID NO:5), were applied to the skin for 14 days.

The group design was set to negative control (sterile water for injection G1), test substance HU024 (SEQ ID NO:2) 20 ug/head/day (G2), test substance HU024 (SEQ ID NO:2) 60 ug/head/day (G3), test substance HU025 (SEQ ID NO:3) 20 ug/head/day (G4), test substance HU025 (SEQ ID NO:3) 60 ug/head/day (G5), test substance HU026 (SEQ ID NO:4) 20 ug/head/day (G6), test substance HU026 (SEQ ID NO:4) 60 ug/head/day (G7), test substance HU027 (SEQ ID NO:5) 20 ug/head/day (G8), test substance HU027 (SEQ ID NO:5) 60 ug/head/day (G9) and positive control minoxyl 3% (G10) administered groups. Each group had 10 animals.

After the animal was put under anesthesia using zoletil (1 mL/kg, i.p), the back of the animal was primarily shaved using a depilator, and Veet depilatory was evenly applied on the back. After about 5 minutes, the applied site was cleaned up using gauze moistened with sterile water for injection. Only animal whose shaved back was scarlet in color was used for group separation. The test substance was applied to the same site daily once per day, 7 times per week for 14 days, and the test substance was evenly applied to the shaved site (on the back) by rubbing with a glass rod about 10 times.

The test item was measurements of dead animal, general syndrome, weight change, hair growing area and hair weight, and comparison with negative control was conducted.

The hair growing area (%) relative to the test substance-applied area was measured and determined, and Image analyzer program (Image Pro Plus ver. 6.3, Cybermetics, USA) was used to measure. It was measured on the 1st, 3rd, 7th, 10th and 14th days after test substance administration. Imaging was performed together with the measurements on the date when the hair area was measured. On the next day after the end of application, the animals were killed by $CO_2$ gas, and hair on the hair growing area was removed by a depilator and hair weight was measured.

TABLE 35

| Score | Extent of hair growth |
|---|---|
| 0 | None |
| 1 | 0~25% hair growth at shaved site |
| 2 | 26~50% hair growth at shaved site |
| 3 | 51~75% hair growth at shaved site |
| 4 | 76~100% hair growth at shaved site |

The measurement results were analyzed using SPSS (ver. 10.1K), Duncan t-test for weight changes was conducted through one-way analysis of variance, hair weight was compared between groups using Student's t-test, and hair growing area was compared between groups through non-parametric multiple comparison procedures Whitney-Mann methods. $P<0.05$ was determined to be statistically significant.

The test results are as follows:

With regard to weight changes, any difference was not observed in test substance administered group compared to negative control. Rather, in comparison with negative control on the 7th and 11st days after administration, a statistically significant weight increase was observed in control substance minoxyl 3% administered group (P<0.05 or P<0.01). The increased weight in control substance minoxyl 3% administered group was thought to be weight increase that is an adverse effect of the active ingredient of minoxyl, minoxidil (Table 36, FIG. 33).

TABLE 36

| | MALE BODY WEIGHTS (g) | | |
|---|---|---|---|
| | Day 1 | Day 7 | Day 11 |
| G1 | 21.41 ± 0.91 | 22.62 ± 1.19 | 23.64 ± 1.29 |
| G2 | 21.34 ± 0.60 | 22.64 ± 0.76 | 24.15 ± 0.86 |
| G3 | 21.54 ± 0.53 | 23.02 ± 0.74 | 24.30 ± 1.08 |
| G4 | 21.20 ± 1.23 | 22.63 ± 1.01 | 23.77 ± 1.17 |
| G5 | 21.53 ± 0.63 | 23.20 ± 0.83 | 24.23 ± 1.02 |
| G6 | 21.20 ± 0.77 | 22.48 ± 1.12 | 23.75 ± 1.27 |
| G7 | 21.58 ± 0.61 | 22.80 ± 1.03 | 23.83 ± 1.30 |
| G8 | 21.71 ± 0.59 | 23.27 ± 0.71 | 23.98 ± 0.79 |
| G9 | 21.77 ± 0.87 | 23.07 ± 1.13 | 23.97 ± 1.14 |
| G10 | 20.70 ± 1.24 | 23.85 ± 0.75* | 25.73 ± 1.13** |

Data are expressed as Mean ± S.D. The results were statistically analyzed by Student's t-test.
*significantly different from G1, P < 0.05
**significantly different from G1, P < 0.01

As a result of measuring the hair growing area, in comparison of test substance administered group and negative control, any difference was not observed until the 7th day after administration. On the 10th and 14th days, a statistically significant increase in hair growing area was observed in test substance HU025 (SEQ ID NO:3) 60 ug/head/day administered group (G5) compared to negative control (P<0.05). The trend toward increased hair growing area by about 20% or more was also observed in the other test substance administered groups except test substance HU025 (SEQ ID NO:3) 20 ug/head/day administered group on the 10th and 14th day when compared to negative control. As compared to negative control, a statistically significant increase in hair growing area was observed in control substance minoxyl 3% administered group on the 4th, 10th and 14th days (P<0.01) (Table 37, FIG. 34).

TABLE 37

| | MALE HAIR AREA (%) | | | | |
|---|---|---|---|---|---|
| | Day 1 | Day 4 | Day 7 | Day 10 | Day 14 |
| G1 | 0.05 ± 0.04 | 0.02 ± 0.02 | 0.92 ± 0.33 | 2.74 ± 1.02 | 43.30 ± 9.48 |
| G2 | 0.02 ± 0.01 | 0.06 ± 0.04 | 0.44 ± 0.19 | 7.55 ± 2.56 | 67.34 ± 9.03 |
| G3 | 0.04 ± 0.04 | 0.00 ± 0.00 | 0.85 ± 0.75 | 6.56 ± 3.04 | 55.69 ± 12.45 |
| G4 | 0.04 ± 0.03 | 0.06 ± 0.05 | 0.47 ± 0.22 | 2.04 ± 0.66 | 39.88 ± 8.74 |
| G5 | 0.04 ± 0.04 | 0.42 ± 0.33 | 0.72 ± 0.51 | 19.61 ± 9.01* | 75.45 ± 6.65* |
| G6 | 0.10 ± 0.05 | 0.13 ± 0.07 | 0.43 ± 0.30 | 7.67 ± 4.54 | 56.64 ± 12.26 |
| G7 | 0.07 ± 0.04 | 0.22 ± 0.13 | 0.69 ± 0.37 | 13.54 ± 4.75 | 65.41 ± 11.62 |
| G8 | 0.13 ± 0.13 | 0.32 ± 0.14 | 0.44 ± 0.17 | 8.81 ± 3.57 | 56.95 ± 9.83 |
| G9 | 0.17 ± 0.11 | 0.33 ± 0.22 | 0.50 ± 0.26 | 8.20 ± 3.43 | 61.95 ± 11.30 |
| G10 | 0.01 ± 0.01 | 0.77 ± 0.26** | 1.78 ± 1.07 | 29.78 ± 8.09** | 90.51 ± 4.50** |

Data are expressed as Mean ± S.E.M. The results were statistically analyzed by Whittney-Mann methods.
*significantly different from G1, P < 0.05
**significantly different from G1, P < 0.01

As a result of measuring hair weight, in comparison with negative control, a statistically significant increase in hair weight was observed in test substance HU026 (SEQ ID NO:4) 60 ug/head/day administered group (P<0.05). Among the other test substance administered groups, in comparison with negative control, a weight increase by about 100% or more was observed in the remaining test substance administered groups except HU025 (SEQ ID NO:3) 20 ug/head/day and HU027 (SEQ ID NO:5) 20 ug/head/day administered group. As compared to negative control, a statistically significant increase hair weight was observed in control substance minoxyl 3% administered group (P<0.01) (Table 38, FIG. 35).

TABLE 38

| | MALE HAIR WEIGHTS (g) |
|---|---|
| G1 | 0.008 ± 0.004 |
| G2 | 0.016 ± 0.003 |
| G3 | 0.023 ± 0.008 |
| G4 | 0.005 ± 0.002 |
| G5 | 0.021 ± 0.007 |
| G6 | 0.021 ± 0.008 |
| G7 | 0.026 ± 0.007* |
| G8 | 0.010 ± 0.003 |
| G9 | 0.016 ± 0.005 |
| G10 | 0.031 ± 0.006** |

Data are expressed as Mean ± S.E.M. The results were statistically analyzed by Student's t-test.
*significantly different from G1, P < 0.05
**significantly different from G1, P < 0.01

Example 5. Glaucoma Test Effect

For control drug, Taflotan eye drops (Santen Pharmaceutical Co., Ltd.) were used, and for test drug, Taflotan eye drops+HU024 (SEQ ID NO:2) (sample 1), HU024 (SEQ ID NO:2) (sample 2), HU025 (SEQ ID NO:3) (sample 3), HU026 (SEQ ID NO:4) (sample 4), and HU027 (SEQ ID NO:5) (sample 5) were used, and testing was performed on glaucoma animal model having microbead-induced elevated intraocular pressure. In experimental animal model, Rompun solution for injection and zoletil were mixed and used to put the experimental animal under anesthesia, topical anesthetic Alcaine was applied to eye, 1×10⁶ microbead/mL 1 μL was injected into anterior chamber using micro glass needle to induce an increase in intraocular pressure for 2 weeks (IOVS 2011 Vol. 52 36-).

The control drug and 5 samples were provided to the experimental animal having the elevated intraocular pressure for 2 weeks, 5 samples were applied to eye once daily, comparative verification of efficacy was performed, and intraocular pressure reduction and optic nerve cell in the retina was observed through administration for 4 weeks.

The intraocular pressure was measured using a contact-type intraocular pressure meter Tono lab's tonometer TV02 model. Furthermore, to analyze optic nerve cell in the retina of glaucoma animal model, the scalp of the anesthetized rats was enucleated and got exposed, then the coordinates of superior culiculus in the brain connected to optic nerve were determined using Bregma and Lamda as reference points and were marked, a hole was created, and 3% Fluorogold was injected. In 5-7 days after fluorescent probe injection, the eye was enucleated and fixed in 4% paraformaldehyde at room temperature for 4 hours. The retina was separated from choroid of the fixed eye and mounted on a slide. In each experimental group slide, optic nerve cell expressing fluorescence was detected using fluorescence microscope, images were taken at a magnification of ×40 and ×200, and data was collected.

As a result of conducting the intraocular pressure test, the intraocular pressure increased to 21.9±8.3 mmHg for 2 weeks. After the elevated intraocular pressure was identified, the results of administering samples 1-5 were shown in FIG. 36. A reduction in intraocular pressure was observed in samples 2 and 3, and significance was not observed in the remaining samples. It is considered that a slight reduction in intraocular pressure on the whole is attributed to the microbead model properties and is not relevant to the intraocular pressure decrease effect of the sample. In positive control, the intraocular pressure reduced as reported, and the intraocular pressure numerical value (15.9±2.9, 20.89%) considerably reduced as compared to negative control (FIG. 36).

As a result of analyzing optic nerve cell, significant optic nerve cell death was observed in negative control as compared to control group, and in samples 3 and 4 administered group and positive control, or Tafluprost applied group, protection from optic nerve cell death was observed. In the case of sample 3, it is thought to be result of the reduced intraocular pressure similar to FIG. 36, and in the case of sample 4, the intraocular pressure did not reduce but the optic nerve cell protection effect was found (FIG. 37).

In conclusion, sample 3, or HU025 (SEQ ID NO:3) had an effect in reducing the intraocular pressure featuring glaucoma. In addition, in many cases of domestic glaucoma patients, vision loss occurs due to optic nerve damage though the intraocular pressure is not high, and it is expected that HU025 (SEQ ID NO:3) sample can be used as drug to treat glaucoma because of having a repair efficacy for damaged optic nerve.

INDUSTRIAL APPLICABILITY

Using the peptide or its fragment according to the present disclosure, it is possible to effectively treat burns and glaucoma, obtain an excellent effect in reducing skin wrinkles, and it is effective in the promotion of hair restoration and hair growth as well as the prevention of hair loss, so it can be used for a cosmetic composition and a pharmaceutical composition.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for protecting optic nerves, the method comprising:
   administering to a subject in need thereof an effective amount of a peptide consisting of an amino acid sequence of SEQ ID NO: 1 comprising an RGD motif (Arg-Gly-Asp motif) or its fragment.

2. The method according to claim 1, wherein the fragment is at least one selected from the group consisting of the following fragments:
   1) a fragment consisting of 5-45 amino acids comprising the RGD motif of SEQ ID NO: 1, optionally with no disulfide bond or 3 or less disulfide bonds between cysteines in the fragment;
   2) a fragment comprising 30th-38th amino acids in the amino acid sequence of SEQ ID NO: 1, optionally with no disulfide bond or 1 or more disulfide bonds between cysteines in the fragment;
   3) a fragment comprising 32nd-43rd amino acids in the amino acid sequence of SEQ ID NO: 1, optionally with no disulfide bond or 1 or more disulfide bonds between cysteines in the fragment;
   4) a fragment comprising 30th-44th amino acids in the amino acid sequence of SEQ ID NO: 1, optionally with no disulfide bond or 1 or more disulfide bonds between cysteines in the fragment;
   5) a fragment comprising 18th-54th amino acids in the amino acid sequence of SEQ ID NO: 1, optionally with no disulfide bond or 1 or more disulfide bonds between cysteines in the fragment; and
   6) a fragment comprising 10th-54th amino acids in the amino acid sequence of SEQ ID NO: 1, optionally with no disulfide bond or 1 or more disulfide bonds between cysteines in the fragment.

3. The method according to claim 1, wherein the fragment is at least one selected from the group consisting of the following fragments:
   1) a fragment consisting of 9, 12 or 15 amino acids comprising the RGD motif of SEQ ID NO: 1, optionally with no disulfide bond or 3 or less disulfide bonds between cysteines in the fragment;
   2) a fragment consisting of 30th-38th amino acids in the amino acid sequence of SEQ ID NO: 1;
   3) a fragment consisting of 32nd-43rd amino acids in the amino acid sequence of SEQ ID NO: 1, with a disulfide bond between 36th cysteine and 42nd cysteine;
   4) a fragment consisting of 30th-44th amino acids in the amino acid sequence of SEQ ID NO: 1, with no disulfide bond between cysteines in the fragment; or
   5) a fragment consisting of 30th-44th amino acids in the amino acid sequence of SEQ ID NO: 1, with a disulfide bond between cysteines in the fragment.

4. The method according to claim 1, wherein the subject has elevated intraocular pressure, and the fragment has the effect of protecting optic nerves by reducing the intraocular pressure of the subject.

5. The method according to claim 1, wherein the subject has damaged optic nerve cells, and the fragment has the effect of protecting optic nerves by repairing the damaged optic nerve cells of the subject.

6. The method according to claim 1, wherein the subject has glaucoma or at risk of glaucoma, and the fragment has the effect of treating or preventing glaucoma by reducing intraocular pressure and/or repairing damaged optic nerve cells of the subject.

7. The method according to claim 1, wherein the fragment is topically administered.

* * * * *

SEQUENCE LISTING

```
<160> NUMBER OF SEQ ID NOS: 6

<210> SEQ ID NO 1
<211> LENGTH: 58
<212> TYPE: PRT
<213> ORGANISM: Homo sapiens

<400> SEQUENCE: 1

Thr Cys Gln Leu Arg Pro Gly Ala Gln Cys Ala Ser Asp Gly Pro Cys
1               5                   10                  15

Cys Gln Asn Cys Gln Leu Arg Pro Ser Gly Trp Gln Cys Arg Pro Thr
            20                  25                  30

Arg Gly Asp Cys Asp Leu Pro Glu Phe Cys Pro Gly Asp Ser Ser Gln
        35                  40                  45

Cys Pro Pro Asp Val Ser Leu Gly Asp Gly
    50                  55

<210> SEQ ID NO 2
<211> LENGTH: 15
<212> TYPE: PRT
<213> ORGANISM: Homo sapiens
<220> FEATURE:
<221> NAME/KEY: DISULFID
<222> LOCATION: (7)..(13)

<400> SEQUENCE: 2

Arg Pro Thr Arg Gly Asp Cys Asp Leu Pro Glu Phe Cys Pro Gly
```

<210> SEQ ID NO 3
<211> LENGTH: 15
<212> TYPE: PRT
<213> ORGANISM: Homo sapiens

<400> SEQUENCE: 3

```
Arg Pro Thr Arg Gly Asp Cys Asp Leu Pro Glu Phe Cys Pro Gly
1               5                   10                  15
```

<210> SEQ ID NO 4
<211> LENGTH: 12
<212> TYPE: PRT
<213> ORGANISM: Homo sapiens
<220> FEATURE:
<221> NAME/KEY: DISULFID
<222> LOCATION: (5)..(11)

<400> SEQUENCE: 4

```
Thr Arg Gly Asp Cys Asp Leu Pro Glu Phe Cys Pro
1               5                   10
```

<210> SEQ ID NO 5
<211> LENGTH: 9
<212> TYPE: PRT
<213> ORGANISM: Homo sapiens

<400> SEQUENCE: 5

```
Arg Pro Thr Arg Gly Asp Cys Asp Leu
1               5
```

<210> SEQ ID NO 6
<211> LENGTH: 814
<212> TYPE: PRT
<213> ORGANISM: Homo sapiens

<400> SEQUENCE: 6

```
Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
                20                  25                  30

Gln Ala Glu Ser Glu Lys Ala Pro Arg Glu Pro Leu Glu Pro Gln Val
            35                  40                  45

Leu Gln Asp Asp Leu Pro Ile Ser Leu Lys Lys Val Leu Gln Thr Ser
        50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95

Leu Val Trp Tyr Gln Pro Asp Gly Thr Arg Val Val Ser Glu Gly His
            100                 105                 110

Thr Leu Glu Asn Cys Cys Tyr Gln Gly Arg Val Arg Gly Tyr Ala Gly
        115                 120                 125

Ser Trp Val Ser Ile Cys Thr Cys Ser Gly Leu Arg Gly Leu Val Val
    130                 135                 140

Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175
```

```
His Thr Cys Ala Leu Ser Trp Arg Glu Ser Val His Thr Gln Thr Pro
            180                 185                 190

Pro Glu His Pro Leu Gly Gln Arg His Ile Arg Arg Arg Arg Asp Val
            195                 200                 205

Val Thr Glu Thr Lys Thr Val Glu Leu Val Ile Val Ala Asp His Ser
210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
            260                 265                 270

Ile Ser Pro Asn Pro Ala Val Thr Leu Glu Asn Phe Leu His Trp Arg
            275                 280                 285

Arg Ala His Leu Leu Pro Arg Leu Pro His Asp Ser Ala Gln Leu Val
            290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
            340                 345                 350

Ser Leu Gly Leu Asp His Asp Leu Pro Gly Asn Ser Cys Pro Cys Pro
            355                 360                 365

Gly Pro Ala Pro Ala Lys Thr Cys Ile Met Glu Ala Ser Thr Asp Phe
370                 375                 380

Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
                405                 410                 415

Leu Pro Pro Met Ala Ala Phe Cys Gly Asn Met Phe Val Glu Pro Gly
            420                 425                 430

Glu Gln Cys Asp Cys Gly Phe Leu Asp Asp Cys Val Asp Pro Cys Cys
            435                 440                 445

Asp Ser Leu Thr Cys Gln Leu Arg Pro Gly Ala Gln Cys Ala Ser Asp
450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
            500                 505                 510

Ala Gly Gly Gln Ala Val Cys Met His Gly Arg Cys Ala Ser Tyr Ala
            515                 520                 525

Gln Gln Cys Gln Ser Leu Trp Gly Pro Gly Ala Gln Pro Ala Ala Pro
            530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
                565                 570                 575

Ile Cys Gly Gln Leu Gln Cys Gln Thr Gly Arg Thr Gln Pro Leu Leu
            580                 585                 590

Gly Ser Ile Arg Asp Leu Leu Trp Glu Thr Ile Asp Val Asn Gly Thr
```

```
                595                 600                 605
Glu Leu Asn Cys Ser Trp Val His Leu Asp Leu Gly Ser Asp Val Ala
        610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
            660                 665                 670

Cys Tyr Cys Glu Glu Gly Trp Ala Pro Pro Asp Cys Thr Thr Gln Leu
        675                 680                 685

Lys Ala Thr Ser Ser Leu Thr Thr Gly Leu Leu Leu Ser Leu Leu Val
        690                 695                 700

Leu Leu Val Leu Val Met Leu Gly Ala Ser Tyr Trp Tyr Arg Ala Arg
705                 710                 715                 720

Leu His Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
            740                 745                 750

Leu Leu Ala Arg Gly Thr Lys Ser Gln Gly Pro Ala Lys Pro Pro Pro
        755                 760                 765

Pro Arg Lys Pro Leu Pro Ala Asp Pro Gln Gly Arg Cys Pro Ser Gly
770                 775                 780

Asp Leu Pro Gly Pro Gly Ala Gly Ile Pro Pro Leu Val Val Pro Ser
785                 790                 795                 800

Arg Pro Ala Pro Pro Pro Thr Val Ser Ser Leu Tyr Leu
                805                 810
```